United States Patent
Oguro et al.

(10) Patent No.: US 10,807,987 B2
(45) Date of Patent: Oct. 20, 2020

(54) HETEROCYCLIC COMPOUND AND USE THEREOF

(71) Applicant: Takeda Pharmaceutical Company Limited, Osaka-shi, Osaka (JP)

(72) Inventors: Yuya Oguro, Fujisawa (JP); Shigemitsu Matsumoto, Fujisawa (JP); Takeshi Wakabayashi, Fujisawa (JP); Norihito Tokunaga, Fujisawa (JP); Taku Kamei, Fujisawa (JP); Mitsuhiro Ito, Fujisawa (JP); Satoshi Mikami, Fujisawa (JP); Masaki Seto, Fujisawa (JP); Shinji Morimoto, Fujisawa (JP); Shinji Nakamura, Fujisawa (JP); Sachie Takashima, Fujisawa (JP); Masataka Murakami, Fujisawa (JP); Masaki Daini, Fujisawa (JP); Makoto Kamata, Fujisawa (JP); Minoru Nakamura, Fujisawa (JP); Yasufumi Wada, Fujisawa (JP); Hiroyuki Kakei, Fujisawa (JP); Kazuaki Takami, Fujisawa (JP); Taisuke Tawaraishi, Fujisawa (JP); Jumpei Aida, Fujisawa (JP); Kouichi Iwanaga, Fujisawa (JP); Satoshi Yamamoto, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/366,710

(22) Filed: Mar. 27, 2019

(65) Prior Publication Data

US 2019/0300536 A1   Oct. 3, 2019

(30) Foreign Application Priority Data

Mar. 28, 2018 (JP) ................ 2018-062939

(51) Int. Cl.
   *C07D 487/04* (2006.01)
   *A61K 9/20* (2006.01)
   *A61K 9/48* (2006.01)
   *C07D 471/04* (2006.01)
   *A61P 25/00* (2006.01)

(52) U.S. Cl.
   CPC .......... *C07D 487/04* (2013.01); *A61K 9/2095* (2013.01); *A61K 9/4833* (2013.01); *A61P 25/00* (2018.01); *C07D 471/04* (2013.01)

(58) Field of Classification Search
   CPC .................................. C07D 487/04
   USPC ...................................... 514/243
   See application file for complete search history.

(56) References Cited

U.S. PATENT DOCUMENTS

| 6,331,640 B1 | 12/2001 | Fotouhi et al. |
|---|---|---|
| 2002/0052512 A1 | 5/2002 | Fotouhi et al. |
| 2004/0006236 A1 | 1/2004 | Fotouhi et al. |
| 2005/0080119 A1 | 4/2005 | Fotouhi et al. |
| 2007/0155671 A1 | 7/2007 | Fotouhi et al. |
| 2008/0234318 A1 | 9/2008 | Gudmundsson et al. |
| 2012/0238569 A1 | 9/2012 | Gillespie et al. |
| 2014/0315945 A1 | 10/2014 | Campbell et al. |
| 2016/0031907 A1 | 2/2016 | Campbell et al. |
| 2016/0244464 A1 | 8/2016 | Campbell et al. |
| 2017/0362223 A1 | 12/2017 | Kimura et al. |

FOREIGN PATENT DOCUMENTS

| WO | WO-00/21920 A1 | 4/2000 |
|---|---|---|
| WO | WO-2007/027999 A2 | 3/2007 |
| WO | WO-2012/123471 A1 | 9/2012 |
| WO | WO-2014/172044 A1 | 10/2014 |
| WO | WO-2016/104434 A1 | 6/2016 |

OTHER PUBLICATIONS

Jin et al., "Developmental Expression, Subcellular Localization, and Tyrosine Phosphorylation of NR2A and NR2B in the Rat Brain," Mol. Cells, 1997, 7(1):64-71.

Monyer et al., "Developmental and Regional Expression in the Rat Brain and Functional Properties of Four NMDA Receptors," Neuron, Mar. 1994, 12:529-540.

Watanabe et al., "Distinct Distributions of Five N-Methyl-D-Aspartate Receptor Channel Subunit mRNAs in the Forebrain," The Journal of Comparative Neurology, 1993, 338:377-390.

*Primary Examiner* — Kahsay Habte
(74) *Attorney, Agent, or Firm* — Foley & Lardner LLP

(57) ABSTRACT

The present invention provides a heterocyclic compound having an antagonistic action on an NMDA receptor containing the NR2B subunit, and expected to be useful as an agent for the prophylaxis or treatment of major depression, bipolar disorder, migraine, pain, behavioral and psychological symptoms of dementia and the like.

The present invention relates to a compound represented by the formula (I):

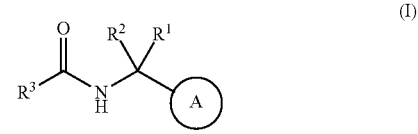

wherein each symbol is as described in the description, or a salt thereof.

8 Claims, No Drawings

HETEROCYCLIC COMPOUND AND USE THEREOF

TECHNICAL FIELD

The present invention relates to a heterocyclic compound having an antagonistic action on an N-methyl-D-aspartic acid (NMDA) receptor containing the NR2B subunit, and expected to be useful as an agent for the prophylaxis or treatment of major depression, bipolar disorder, migraine, pain, behavioral and psychological symptoms of dementia.

BACKGROUND OF THE INVENTION

The major excitatory neurotransmitter in the central nervous system such as the brain, spinal cord and the like is glutamic acid, and its signal transduction is mediated by N-methyl-D-aspartic acid (NMDA) receptor, gamma-amino-3-hydroxy-5-methyloxazole-4-propionic acid (AMPA)/kainic acid (KA) receptor and metabotropic glutamate receptor. Of these, NMDA receptor is highly permeable to cations including calcium ion and mediate excitatory neurotransmission by depolarizing nerve cells. In addition, calcium influx into the cell via NMDA receptor functions as a secondary messenger, and causes plastic changes in the nerve function through actions such as changes in the intracellular phosphorylation signal, regulation of transcription and translation of genes, and the like. Thus, NMDA receptor plays an important role in the functional regulation of central nervous system.

The NMDA receptor is a receptor composed of a tetramer in which 2 to 3 subunits from among NR1, NR2A, NR2B, NR2C, NR2D, NR3A, NR3B subunits are associated, and, to have the function of a receptor responsible for excitatory neurotransmission, the presence of the NR1 subunit is essential. Since the NR1 subunit is contained in all NMDA receptors having the function, it is widely distributed in the central nervous system; however, the distribution and the timing of expression of the NR2 subunit are different for each subunit. For example, NR2A and NR2C subunits are detected from only immediately before birth, whereas NR2B and NR2D subunits are observed from an early stage in embryonic development. For example, while the NR2A subunit is widely distributed in the brain, the NR2B subunit is locally expressed in the forebrain and the NR2C subunit is locally expressed in the cerebellum (non-patent document 1).

An NMDA receptor containing the NR2B subunit, which is the target in the present invention, is highly expressed in the cerebral cortex (particularly layer 2 and 3), hippocampus, amygdala, ventral nucleus of thalamus, and olfactory bulb in the brain of adult rodents. In the spinal cord, the NMDA receptor is confined to the dorsal horn of the spinal cord (particularly the second layer) (non-patent document 2). Moreover, in a single cell, the NMDA receptor containing the NR2B subunit is most highly expressed in postsynaptic density and the expression is also found in the extrasynaptic region (non-patent document 3). This suggests that an NMDA receptor containing the NR2B subunit functions widely in the brain and is effective for the prophylaxis or treatment of central diseases.

Patent Document 1 discloses the following compound having an inhibitory action of enhancer of zeste homolog (EZH), and useful for the prophylaxis or treatment of cancer (cancer including central nervous system) and the like.

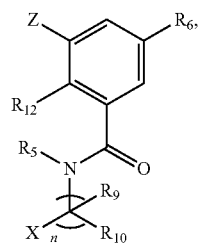

wherein each symbol is as defined in the document.

Patent Document 2 discloses the following compound having a selective CXCR4 antagonistic action and useful for cellular protection from HIV infection.

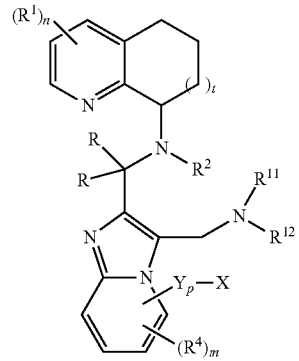

wherein each symbol is as defined in the document.

Patent Document 3 discloses the following compound having a LFA-1 antagonistic action and dual LFA-1/MAC-1 antagonistic action, and useful for the prophylaxis or treatment of inflammatory disease (asthma, COPD, etc.).

wherein each symbol is as defined in the document.

Patent Document 4 discloses the following compound having a blocking activity of an intracellular adhesion molecule (ICAM), and useful for the prophylaxis or treatment of inflammatory disease (rheumatoid arthritis, multiple sclerosis, Crohn's disease, ulcerative colitis, etc.) and the like.

wherein each symbol is as defined in the document.

Patent Document 5 discloses the following compound having an antagonistic action on an N-methyl-D-aspartic acid (NMDA) receptor containing the NR2B subunit, and useful as an agent for the prophylaxis or treatment of major depression, bipolar disorder, migraine, pain, behavioral and psychological symptoms of dementia and the like.

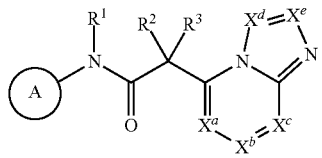

wherein each symbol is as defined in the document.

DOCUMENT LIST

Patent Document

[Patent Document 1] WO 2014/172044
[Patent Document 2] WO 2007/027999
[Patent Document 3] WO 2012/123471
[Patent Document 4] WO 00/21920
[Patent Document 5] WO 2016/104434

Non-Patent Document

[Non-Patent Document 1] Neuron, vol. 12, pp. 529-540, 1994
[Non-Patent Document 2] the Journal of Comparative Neurology (J. Comp. Neurol.), vol. 338, pp. 377-390, 1993
[Non-Patent Document 3] Molecular Cells (Mol. Cells), pp. 64-71, 1997

SUMMARY OF THE INVENTION

Problems to be Solved by the Invention

An object of the present invention is to provide a heterocyclic compound having an antagonistic action on an NMDA receptor containing the NR2B subunit, and expected to be useful as an agent for the prophylaxis or treatment of major depression, bipolar disorder, migraine, pain, behavioral and psychological symptoms of dementia and the like, and a medicament containing the same.

Means of Solving the Problems

The present inventors have conducted intensive studies in an attempt to solve the above-mentioned problem, and found that a compound represented by the following formula (I) has a superior antagonistic action on an NMDA receptor containing the NR2B subunit, which resulted in the completion of the present invention.

Accordingly, the present invention provides the following.

[1] A compound represented by the formula (I):

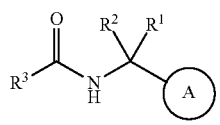

(I)

wherein
the group represented by

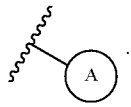

is a group represented by

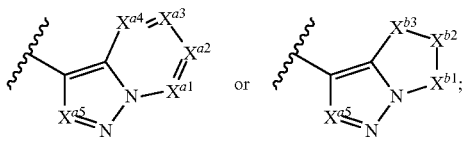

$X^{a1}$, $X^{a2}$, $X^{a3}$, $X^{a4}$ and $X^{a5}$ are each independently $CR^a$ or a nitrogen atom; and
$R^a$ is a hydrogen atom or a substituent, and each $R^a$ in $X^{a1}$, $X^{a2}$, $X^{a3}$, $X^{a4}$ and $X^{a5}$ may be different;
provided that when $X^{a5}$ is $CR^a$, then at least one of $X^{a1}$, $X^{a2}$ and $X^{a3}$ is a nitrogen atom;
$X^{b1}$, $X^{b2}$, $X^{b3}$ and $X^{b4}$ are each independently $CR^b$ or a nitrogen atom, and when $X^{b1}$ or $X^{b3}$ is a nitrogen atom, then the nitrogen atom is optionally substituted; and
$R^b$ is a hydrogen atom or a substituent, and each $R^b$ in $X^{b1}$, $X^{b2}$, $X^{b3}$ and $X^{b4}$ may be different;
provided that at least one of $X^{b1}$, $X^{b2}$, $X^{b3}$ and $X^{b4}$ is a nitrogen atom;
$R^1$ and $R^2$ are each independently a hydrogen atom or a $C_{1-6}$ alkyl group optionally substituted by fluorine atom(s); and
$R^3$ is a group represented by

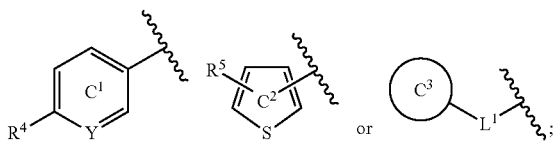

$R^4$ and $R^5$ are each a substituent selected from Substituent Group Z;
Y is a nitrogen atom or $CR^6$;
$R^6$ is a hydrogen atom or a substituent selected from Substituent Group Z;
Ring $C^1$ is a benzene ring or a pyridine ring, each of which is optionally further substituted by one substituent selected from Substituent Group Z;
Ring $C^2$ is a thiophene ring optionally further substituted by one substituent selected from Substituent Group Z;
$L^1$ is an optionally substituted methylene group; and
Ring $C^3$ is a benzene ring, a pyridine ring or a thiophene ring, each of which is optionally further substituted by 1 to 3 substituents selected from Substituent Group Z;
[Substituent Group Z]
(1) an optionally substituted hydrocarbon group,
(2) an optionally substituted heterocyclic group,
(3) an optionally substituted $C_{1-6}$ alkoxy group,
(4) an optionally substituted $C_{3-10}$ cycloalkyloxy group,
(5) a halogen atom,
(6) a cyano group,
(7) an optionally substituted amino group,
(8) an optionally substituted $C_{6-14}$ aryloxy group, and (9) an optionally substituted $C_{1-6}$ alkylthio group,
or a salt thereof (hereinafter sometimes to be abbreviated as "compound (I)").

[2] The compound or salt according to the above-mentioned [1], wherein
the group represented by

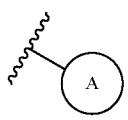

is a group represented by

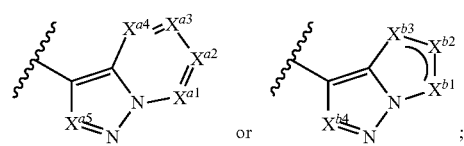

$X^{a1}$ is CH or a nitrogen atom;
$X^{a2}$ is
(1) $CR^a$ wherein $R^a$ is
  (a) a hydrogen atom,
  (b) a halogen atom, or
  (c) a $C_{1-6}$ alkyl group, or
(2) a nitrogen atom;
$X^{a3}$ is
(1) $CR^a$ wherein $R^a$ is
  (a) a hydrogen atom, or
  (b) a $C_{1-6}$ alkyl group, or
(2) a nitrogen atom;
$X^{a4}$ is
(1) $CR^a$ wherein $R^a$ is
  (a) a hydrogen atom, or
  (b) a $C_{1-6}$ alkyl group, or
(2) a nitrogen atom; and
$X^{a5}$ is
(1) $CR^a$ wherein $R^a$ is
  (a) a hydrogen atom,
  (b) a $C_{1-6}$ alkyl group optionally substituted by 1 to 3 substituents selected from a halogen atom and a $C_{1-6}$ alkoxy group,
  (c) a $C_{1-6}$ alkoxy group, or
  (d) a $C_{3-10}$ cycloalkyl group, or
(2) a nitrogen atom;
provided that when $X^{a5}$ is $CR^a$, then at least one of $X^{a1}$, $X^{a2}$ and $X^{a3}$ is a nitrogen atom;
$X^{b1}$ is CH or a nitrogen atom;
$X^{b2}$ is $CR^b$ wherein $R^b$ is
  (a) a hydrogen atom, or
  (b) a $C_{1-6}$ alkyl group;
$X^{b3}$ is a nitrogen atom optionally substituted by a $C_{1-6}$ alkyl group optionally substituted by 1 to 3 halogen atoms; and
$X^{b4}$ is $CR^b$ wherein $R^b$ is
  (a) a hydrogen atom, or
  (b) a $C_{1-6}$ alkyl group;
$R^1$ and $R^2$ are both hydrogen atoms; and $R^3$ is a group represented by

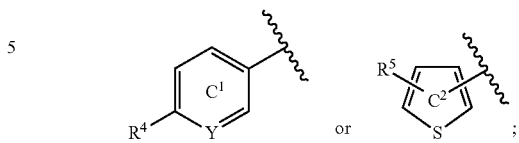

$R^4$ is
(1) a $C_{1-6}$ alkyl group optionally substituted by 1 to 3 halogen atoms,
(2) a $C_{1-6}$ alkoxy group optionally substituted by 1 to 3 halogen atoms,
(3) a $C_{3-10}$ cycloalkyloxy group, or
(4) a halogen atom;
Y is a nitrogen atom or $CR^6$ wherein $R^6$ is a hydrogen atom or a halogen atom; and
Ring $C^1$ is a benzene ring (i.e., Y is $CR^6$) or a pyridine ring (i.e., Y is N), each of which is optionally further substituted by one halogen atom;
$R^5$ is a $C_{1-6}$ alkyl group optionally substituted by 1 to 3 halogen atoms; and
Ring $C^2$ is a thiophene ring substituted by only $R^5$.

[3] The compound or salt according to the above-mentioned [1], wherein
the group represented by

is a group represented by

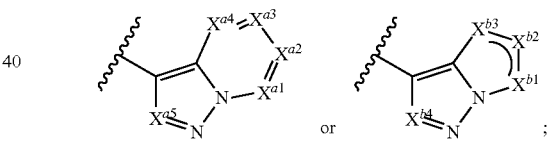

$X^{a1}$ is CH or a nitrogen atom;
$X^{a2}$ is CH;
$X^{a3}$ is CH or a nitrogen atom;
$X^{a4}$ is CH; and
$X^{a5}$ is CH or a nitrogen atom;
provided that when $X^{a5}$ is CH, then at least one of $X^{a1}$ and $X^{a3}$ is a nitrogen atom;
$X^{b1}$ is CH;
$X^{b2}$ is CH;
$X^{b3}$ is a nitrogen atom optionally substituted by a $C_{1-6}$ alkyl group; and
$X^{b4}$ is CH;
$R^1$ and $R^2$ are both hydrogen atoms; and
$R^3$ is a group represented by

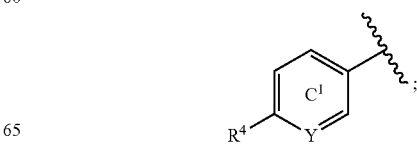

$R^4$ is a $C_{1-6}$ alkoxy group optionally substituted by 1 to 3 halogen atoms;
Y is a nitrogen atom or CH; and
Ring $C^1$ is a benzene ring (i.e., Y is CH) or a pyridine ring (i.e., Y is N), each of which is optionally further substituted by one halogen atom.
[4] The compound or salt according to the above-mentioned [1], wherein
the group represented by is a group represented by $X^{a1}$ is CH or a nitrogen atom;
$X^{a2}$ is CH;
$X^{a3}$ is CH;
$X^{a4}$ is CH; and
$X^{a5}$ is CH or a nitrogen atom;
provided that when $X^{a5}$ is CH, then $X^{a1}$ is a nitrogen atom;
$X^{b1}$ is CH;
$X^{b2}$ is CH;
$X^{b3}$ is a nitrogen atom optionally substituted by a $C_{1-6}$ alkyl group; and
$X^{b4}$ is CH;
$R^1$ and $R^2$ are both hydrogen atoms; and
$R^3$ is a group represented by $R^4$ is a $C_{1-6}$ alkoxy group optionally substituted by 1 to 3 halogen atoms;
Y is a nitrogen atom or CH; and
Ring $C^1$ is a benzene ring (i.e., Y is CH) or a pyridine ring (i.e., Y is N), each of which is optionally further substituted by one halogen atom.
[5] 6-(Difluoromethoxy)-5-fluoro-N-[(pyrazolo[1,5-b]pyridazin-3-yl)methyl]pyridine-3-carboxamide or a salt thereof.
[6] 3-Fluoro-N-[([1,2,3]triazolo[1,5-a]pyridin-3-yl)methyl]-4-(trifluoromethoxy)benzamide or a salt thereof.
[7] 6-(Difluoromethoxy)-5-fluoro-N-[(1-methyl-1H-imidazo[1,2-b]pyrazol-7-yl)methyl]pyridine-3-carboxamide or a salt thereof.
[8] A medicament comprising the compound or salt according to the above-mentioned [1].
[9] The medicament according to the above-mentioned [8], which is an antagonist of an NMDA receptor containing the NR2B subunit.

[10] The medicament according to the above-mentioned [8], which is an agent for the prophylaxis or treatment of major depression, bipolar disorder, migraine, pain, or behavioral and psychological symptoms of dementia.
[11] The compound or salt according to the above-mentioned [1], for use in the prophylaxis or treatment of major depression, bipolar disorder, migraine, pain, or behavioral and psychological symptoms of dementia.
[12] A method of antagonizing an NMDA receptor containing the NR2B subunit in a mammal, which comprises administering an effective amount of the compound or salt according to the above-mentioned [1] to the mammal.
[13] A method for the prophylaxis or treatment of major depression, bipolar disorder, migraine, pain, or behavioral and psychological symptoms of dementia in a mammal, which comprises administering an effective amount of the compound or salt according to the above-mentioned [1] to the mammal.
[14] Use of the compound or salt according to the above-mentioned [1], for the manufacture of an agent for the prophylaxis or treatment of major depression, bipolar disorder, migraine, pain, or behavioral and psychological symptoms of dementia.

Effect of the Invention

The present invention provides a heterocyclic compound having an antagonistic action on an NMDA receptor containing the NR2B subunit and expected to be useful as an agent for the prophylaxis or treatment of major depression, bipolar disorder, migraine, pain, behavioral and psychological symptoms of dementia and the like, and a medicament containing the same.

DETAILED DESCRIPTION OF THE INVENTION

The definition of each substituent used in the present specification is described in detail in the following. Unless otherwise specified, each substituent has the following definition.
In the present specification, examples of the "halogen atom" include fluorine, chlorine, bromine and iodine.
In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.
In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.
In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.
In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),

(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, 3-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl) amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

The definition of each symbol in the formula (I) is explained in detail in the following.

The group represented by

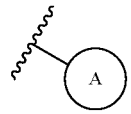

is a group represented by

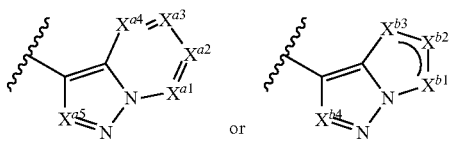

$X^{a1}$, $X^{a2}$, $X^{a3}$, $X^{a4}$ and $X^{a5}$ are each independently $CR^a$ or a nitrogen atom, and $R^a$ is a hydrogen atom or a substituent, and each $R^a$ in $X^{a1}$, $X^{a2}$, $X^{a3}$, $X^{a4}$ and $X^{a5}$ may be different, provided that when $X^{a5}$ is $CR^a$, then at least one of $X^{a1}$, $X^{a2}$ and $X^{a3}$ is a nitrogen atom.

$X^{b1}$, $X^{b2}$, $X^{b3}$ and $X^{b4}$ are each independently $CR^b$ or a nitrogen atom, and when $X^{b1}$ or $X^{b3}$ is a nitrogen atom, then the nitrogen atom is optionally substituted, and $R^b$ is a hydrogen atom or a substituent, and each $R^b$ in $X^{b1}$, $X^{b2}$, $X^{b3}$ and $X^{b4}$ may be different, provided that at least one of $X^{b1}$, $X^{b2}$, $X^{b3}$ and $X^{b4}$ is a nitrogen atom.

$R^a$ is preferably
(a) a hydrogen atom,
(b) a halogen atom (e.g., a fluorine atom),
(c) an optionally substituted $C_{1-6}$ alkyl group (e.g., methyl, ethyl),
(d) an optionally substituted $C_{1-6}$ alkoxy group (e.g., ethoxy), or
(e) an optionally substituted $C_{6-10}$ cycloalkyl group (e.g., cyclopropyl).

$R^a$ is more preferably
(a) a hydrogen atom,
(b) a halogen atom (e.g., a fluorine atom),
(c) a $C_{1-6}$ alkyl group (e.g., methyl, ethyl) optionally substituted by 1 to 3 (preferably 1 to 2) substituents selected from a halogen atom (e.g., a fluorine atom) and a $C_{1-6}$ alkoxy group (e.g., methoxy),
(d) a $C_{1-6}$ alkoxy group (e.g., ethoxy), or
(e) a $C_{3-10}$ cycloalkyl group (e.g., cyclopropyl).

$X^{a1}$ is preferably CH or a nitrogen atom.

$X^{a2}$ is preferably
(1) $CR^a$ wherein $R^a$ is
  (a) a hydrogen atom,
  (b) a halogen atom (e.g., a fluorine atom), or
  (c) an optionally substituted $C_{1-6}$ alkyl group (e.g., methyl), or
(2) a nitrogen atom.

$X^{a2}$ is more preferably
(1) $CR^a$ wherein $R^a$ is
  (a) a hydrogen atom,
  (b) a halogen atom (e.g., a fluorine atom), or
  (c) a $C_{1-6}$ alkyl group (e.g., methyl), or
(2) a nitrogen atom.

$X^{a2}$ is further more preferably CH.

$X^{a3}$ is preferably
(1) $CR^a$ wherein $R^a$ is
  (a) a hydrogen atom, or
  (b) an optionally substituted $C_{1-6}$ alkyl group (e.g., methyl), or
(2) a nitrogen atom.

$X^{a3}$ is more preferably
(1) $CR^a$ wherein $R^a$ is
  (a) a hydrogen atom, or
  (b) a $C_{1-6}$ alkyl group (e.g., methyl), or
(2) a nitrogen atom.

$X^{a3}$ is further more preferably CH or a nitrogen atom.
$X^{a3}$ is particularly preferably CH.

$X^{a4}$ is preferably
(1) $CR^a$ wherein $R^a$ is
  (a) a hydrogen atom, or
  (b) an optionally substituted $C_{1-6}$ alkyl group (e.g., methyl), or
(2) a nitrogen atom.

$X^{a4}$ is more preferably
(1) $CR^a$ wherein $R^a$ is
  (a) a hydrogen atom, or
  (b) a $C_{1-6}$ alkyl group (e.g., methyl), or
(2) a nitrogen atom.

$X^{a4}$ is further more preferably CH.

$X^{a5}$ is preferably
(1) $CR^a$ wherein $R^a$ is
  (a) a hydrogen atom,
  (b) an optionally substituted $C_{1-6}$ alkyl group (e.g., methyl, ethyl),
  (c) an optionally substituted $C_{1-6}$ alkoxy group (e.g., ethoxy), or
  (d) an optionally substituted $C_{3-10}$ cycloalkyl group (e.g., cyclopropyl), or
(2) a nitrogen atom.

$X^{a5}$ is more preferably
(1) $CR^a$ wherein $R^a$ is
  (a) a hydrogen atom,
  (b) a $C_{1-6}$ alkyl group (e.g., methyl, ethyl) optionally substituted by 1 to 3 (preferably 1 to 2) substituents selected from a halogen atom (e.g., a fluorine atom) and a $C_{1-6}$ alkoxy group (e.g., methoxy),
  (c) a $C_{1-6}$ alkoxy group (e.g., ethoxy), or
  (d) a $C_{3-10}$ cycloalkyl group (e.g., cyclopropyl), or
(2) a nitrogen atom.

$X^{a5}$ is further more preferably CH or a nitrogen atom.

Specific examples of the group represented by

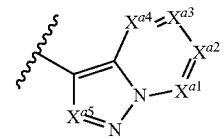

include groups represented by

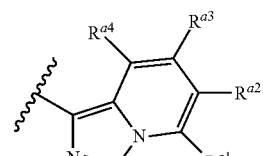 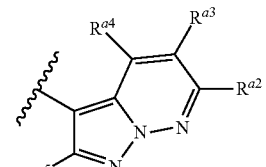

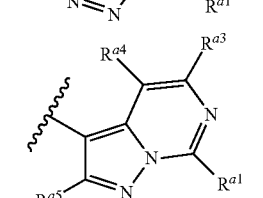 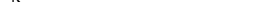

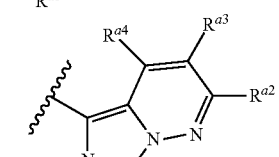 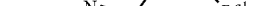

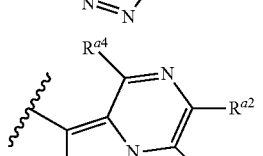 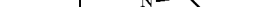

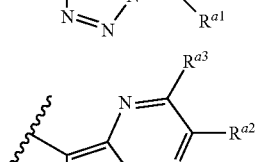 

-continued

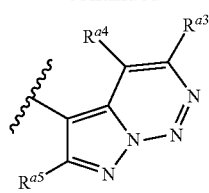

wherein $R^{a1}$, $R^{a2}$, $R^{a3}$, $R^{a4}$ and $R^{a5}$ are each independently a hydrogen atom or a substituent.

The group represented by

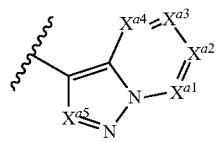

is preferably a group represented by formula (a)-(g):

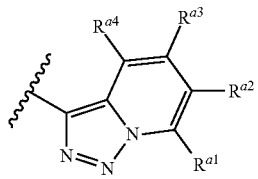 (a)

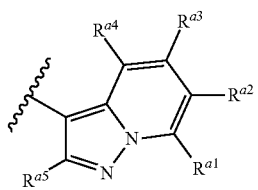 (b)

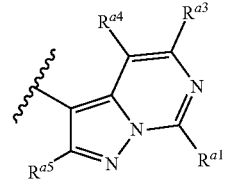 (c)

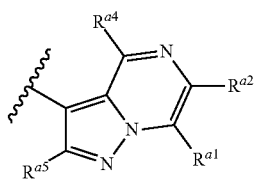 (d)

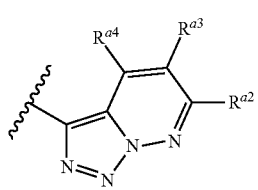 (e)

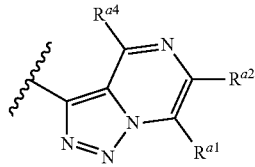 (f)

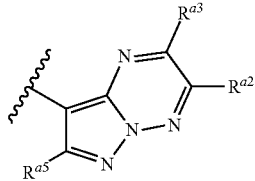 (g)

wherein $R^{a1}$, $R^{a2}$, $R^{a3}$, $R^{a4}$ and $R^{a5}$ are as defined above.

In formula (a),
$R^{a1}$ is preferably a hydrogen atom,
$R^{a2}$ is preferably a hydrogen atom or a halogen atom (e.g., a fluorine atom), more preferably a hydrogen atom,
$R^{a3}$ is preferably a hydrogen atom, and
$R^{a4}$ is preferably a hydrogen atom or a $C_{1-6}$ alkyl group (e.g., methyl), more preferably a hydrogen atom.

In formula (b),
$R^{a2}$ is preferably a hydrogen atom or a $C_{1-6}$ alkyl group (e.g., methyl), more preferably a hydrogen atom,
$R^{a3}$ is preferably a hydrogen atom or a $C_{1-6}$ alkyl group (e.g., methyl), more preferably a hydrogen atom,
$R^{a4}$ is preferably a hydrogen atom or a $C_{1-6}$ alkyl group (e.g., methyl), more preferably a hydrogen atom, and
$R^{a5}$ is preferably
(a) a hydrogen atom,
(b) a $C_{1-6}$ alkyl group (e.g., methyl, ethyl) optionally substituted by 1 to 3 (preferably 1 to 2) substituents selected from a halogen atom (e.g., a fluorine atom) and a $C_{1-6}$ alkoxy group (e.g., methoxy),
(c) a $C_{1-6}$ alkoxy group (e.g., ethoxy), or
(d) a $C_{3-10}$ cycloalkyl group (e.g., cyclopropyl), more preferably a hydrogen atom.

In formula (c),
$R^{a1}$ is preferably a hydrogen atom,
$R^{a3}$ is preferably a hydrogen atom,
$R^{a4}$ is preferably a hydrogen atom, and
$R^{a5}$ is preferably a hydrogen atom or a $C_{1-6}$ alkyl group (e.g., methyl).

In formula (d),
$R^{a1}$ is preferably a hydrogen atom,
$R^{a2}$ is preferably a hydrogen atom,
$R^{a4}$ is preferably a hydrogen atom, and
$R^{a5}$ is preferably a hydrogen atom.

In formula (e),
$R^{a2}$ is preferably a hydrogen atom,
$R^{a3}$ is preferably a hydrogen atom or a $C_{1-6}$ alkyl group (e.g., methyl), more preferably a hydrogen atom, and
$R^{a4}$ is preferably a hydrogen atom or a $C_{1-6}$ alkyl group (e.g., methyl), more preferably a hydrogen atom.

In formula (f),
$R^{a1}$ is preferably a hydrogen atom,
$R^{a2}$ is preferably a hydrogen atom, and
$R^{a4}$ is preferably a hydrogen atom.

In formula (g),
$R^{a2}$ is preferably a hydrogen atom,
$R^{a3}$ is preferably a hydrogen atom, and
$R^{a5}$ is preferably a hydrogen atom.

The group represented by

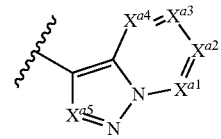

more preferably a group represented by formula (a), (b), (d) or (e):

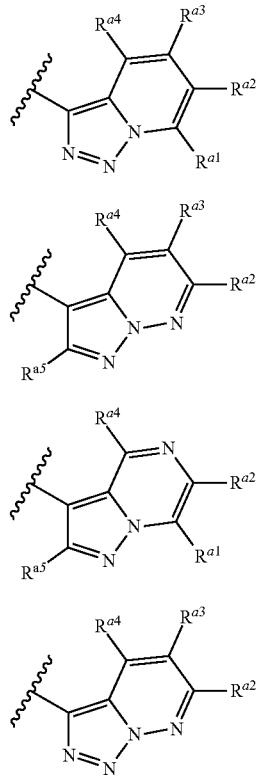

wherein $R^{a1}$, $R^{a2}$, $R^{a3}$, $R^{a4}$ and $R^{a5}$ are as defined above.
In formula (a),
$R^{a1}$ is preferably a hydrogen atom,
$R^{a2}$ is preferably a hydrogen atom,
$R^{a3}$ is preferably a hydrogen atom, and
$R^{a4}$ is preferably a hydrogen atom.
In formula (b),
$R^{a2}$ is preferably a hydrogen atom,
$R^{a3}$ is preferably a hydrogen atom,
$R^{a4}$ is preferably a hydrogen atom, and
$R^{a5}$ is preferably a hydrogen atom.
In formula (d),
$R^{a1}$ is preferably a hydrogen atom,
$R^{a2}$ is preferably a hydrogen atom,
$R^{a4}$ is preferably a hydrogen atom, and
$R^{a5}$ is preferably a hydrogen atom.
In formula (e),
$R^{a2}$ is preferably a hydrogen atom,
$R^{a3}$ is preferably a hydrogen atom, and
$R^{a4}$ is preferably a hydrogen atom.

The group represented by

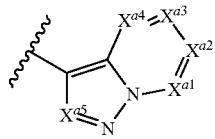

is further more preferably a group represented by formula (a) or (b):

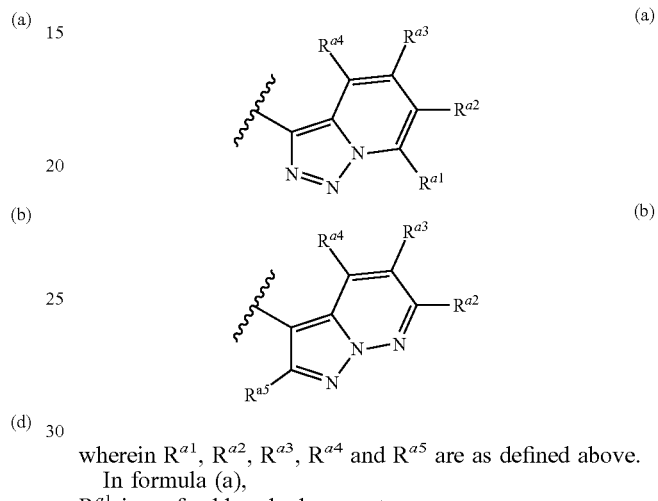

wherein $R^{a1}$, $R^{a2}$, $R^{a3}$, $R^{a4}$ and $R^{a5}$ are as defined above.
In formula (a),
$R^{a1}$ is preferably a hydrogen atom,
$R^{a2}$ is preferably a hydrogen atom,
$R^{a3}$ is preferably a hydrogen atom, and
$R^{a4}$ is preferably a hydrogen atom.
In formula (b),
$R^{a2}$ is preferably a hydrogen atom,
$R^{a3}$ is preferably a hydrogen atom,
$R^{a4}$ is preferably a hydrogen atom, and
$R^{a5}$ is preferably a hydrogen atom.

The group represented by

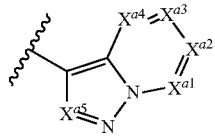

is particularly preferably a group represented by formula (a):

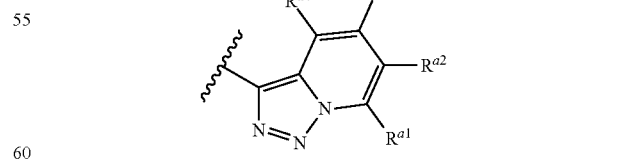

wherein $R^{a1}$, $R^{a2}$, $R^{a3}$ and $R^{a4}$ are as defined above.
In formula (a),
$R^{a1}$ is preferably a hydrogen atom,
$R^{a2}$ is preferably a hydrogen atom,
$R^{a3}$ is preferably a hydrogen atom, and
$R^{a4}$ is preferably a hydrogen atom.

Or, the group represented by

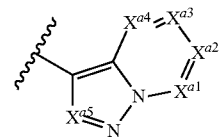

is particularly preferably a group represented by formula (b):

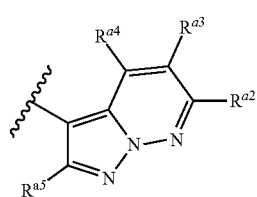

wherein $R^{a2}$, $R^{a3}$, $R^{a4}$ and $R^{a5}$ are as defined above.

In formula (b),
$R^{a2}$ is preferably a hydrogen atom,
$R^{a3}$ is preferably a hydrogen atom,
$R^{a4}$ is preferably a hydrogen atom, and
$R^{a5}$ is preferably a hydrogen atom.
$R^b$ is preferably a hydrogen atom.

When $X^{b1}$ or $X^{b3}$ is a nitrogen atom, then the nitrogen atom is preferably optionally substituted by a $C_{1-6}$ alkyl group (e.g., methyl).

$X^{b1}$ is preferably CH.
$X^{b2}$ is preferably CH.
$X^{b3}$ is preferably a nitrogen atom optionally substituted by an optionally substituted $C_{1-6}$ alkyl group (e.g., methyl).
$X^{b3}$ is more preferably a nitrogen atom optionally substituted by a $C_{1-6}$ alkyl group (e.g., methyl).
$X^{b4}$ is preferably CH.

As another embodiment, $R^b$ is preferably
(1) a hydrogen atom, or
(2) an optionally substituted $C_{1-6}$ alkyl group (e.g., methyl).
In this embodiment, $R^b$ is more preferably
(1) a hydrogen atom, or
(2) a $C_{1-6}$ alkyl group (e.g., methyl).
In this embodiment, $R^b$ is particularly preferably a hydrogen atom.

In this embodiment, when $X^{b1}$ or $X^{b3}$ is a nitrogen atom, then the nitrogen atom is preferably optionally substituted by an optionally substituted $C_{1-6}$ alkyl group (e.g., methyl, ethyl), more preferably optionally substituted by a $C_{1-6}$ alkyl group (e.g., methyl, ethyl) optionally substituted by 1 to 3 halogen atoms (e.g., a fluorine atom), further more preferably optionally substituted by a $C_{1-6}$ alkyl group (e.g., methyl).

In this embodiment, $X^{b1}$ is preferably CH or a nitrogen atom.
In this embodiment, $X^{b1}$ is particularly preferably CH.
In this embodiment, $X^{b2}$ is preferably $CR^b$ wherein $R^b$ is
(a) a hydrogen atom, or
(b) an optionally substituted $C_{1-6}$ alkyl group (e.g., methyl).
In this embodiment, $X^{b2}$ is more preferably $CR^b$ wherein $R^b$ is
(a) a hydrogen atom, or
(b) a $C_{1-6}$ alkyl group (e.g., methyl).

In this embodiment, $X^{b2}$ is particularly preferably CH.
In this embodiment, $X^{b3}$ is preferably a nitrogen atom optionally substituted by an optionally substituted $C_{1-6}$ alkyl group (e.g., methyl, ethyl).
In this embodiment, $X^{b3}$ is more preferably a nitrogen atom optionally substituted by a $C_{1-6}$ alkyl group (e.g., methyl, ethyl) optionally substituted by 1 to 3 halogen atoms (e.g., a fluorine atom).
In this embodiment, $X^{b3}$ is further more preferably a nitrogen atom optionally substituted by a $C_{1-6}$ alkyl group (e.g., methyl).
In this embodiment, $X^{b4}$ is preferably $CR^b$ wherein $R^b$ is
(a) a hydrogen atom, or
(b) an optionally substituted $C_{1-6}$ alkyl group (e.g., methyl).
In this embodiment, $X^{b4}$ is more preferably $CR^b$ wherein $R^b$ is
(a) a hydrogen atom, or
(b) a $C_{1-6}$ alkyl group (e.g., methyl).
In this embodiment, $X^{b4}$ is particularly preferably CH.

Specific examples of the group represented by

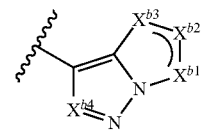

include groups represented by

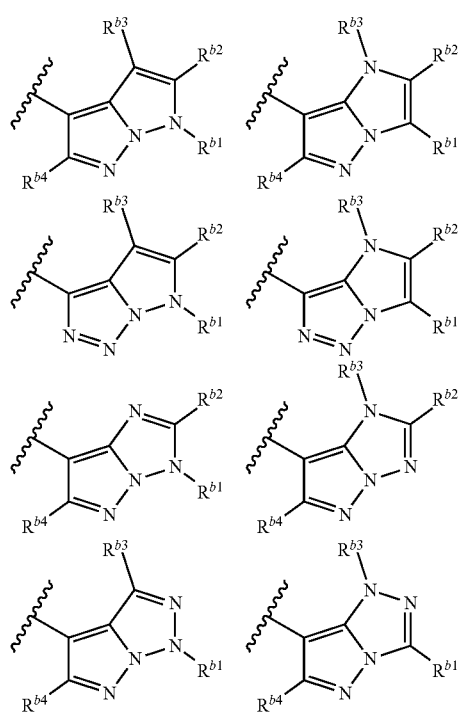

wherein $R^{b1}$, $R^{b2}$, $R^{b3}$ and $R^{b4}$ are each independently a hydrogen atom or a substituent.

The group represented by

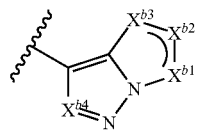

is more preferably a group represented by formula (h) or (i):

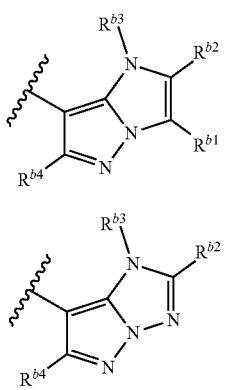

wherein $R^{b1}$, $R^{b2}$, $R^{b3}$ and $R^{b4}$ are as defined above.

In formula (h),
$R^{b1}$ is preferably a hydrogen atom,
$R^{b2}$ is preferably a hydrogen atom or a $C_{1-6}$ alkyl group (e.g., methyl),
$R^{b3}$ is preferably a hydrogen atom or a $C_{1-6}$ alkyl group (e.g., methyl, ethyl) optionally substituted by 1 to 3 halogen atoms (e.g., a fluorine atom), and
$R^{b4}$ is preferably a hydrogen atom or a $C_{1-6}$ alkyl group (e.g., methyl).

In formula (i),
$R^{b2}$ is preferably a hydrogen atom or a $C_{1-6}$ alkyl group (e.g., methyl),
$R^{b3}$ is preferably a hydrogen atom or a $C_{1-6}$ alkyl group (e.g., methyl, ethyl) optionally substituted by 1 to 3 halogen atoms (e.g., a fluorine atom), and
$R^{b4}$ is preferably a hydrogen atom.

The group represented by

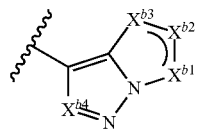

is more preferably a group represented by formula (h):

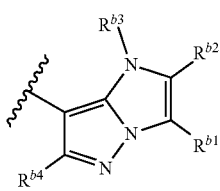

wherein $R^{b1}$, $R^{b2}$, $R^{b3}$ and $R^{b4}$ are as defined above.

In formula (h),
$R^{b1}$ is preferably a hydrogen atom,
$R^{b2}$ is preferably a hydrogen atom,
$R^{b3}$ is preferably a hydrogen atom or a $C_{1-6}$ alkyl group (e.g., methyl), and
$R^{b4}$ is preferably a hydrogen atom.

$R^1$ and $R^2$ are each independently a hydrogen atom or a $C_{1-6}$ alkyl group optionally substituted by fluorine atom(s).
$R^1$ and $R^2$ are preferably both hydrogen atoms.
$R^3$ is a group represented by

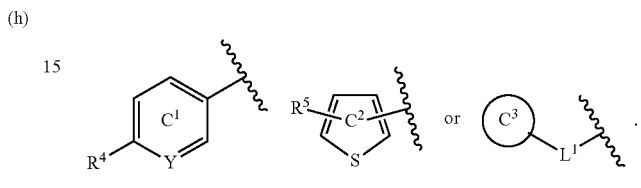

$R^4$ and $R^5$ are each a substituent selected from the below-mentioned Substituent Group Z.

Y is a nitrogen atom or $CR^6$, and $R^6$ is a hydrogen atom or a substituent selected from the below-mentioned Substituent Group Z.

Ring $C_1$ is a benzene ring (i.e., Y is $CR^6$) or a pyridine ring (i.e., Y is N), each of which is optionally further substituted by one substituent selected from the below-mentioned Substituent Group Z.

Ring $C^2$ is a thiophene ring optionally further substituted by one substituent selected from the below-mentioned Substituent Group Z.

$L^1$ is an optionally substituted methylene group.

Ring $C^3$ is a benzene ring, a pyridine ring or a thiophene ring, each of which is optionally further substituted by 1 to 3 substituents selected from the below-mentioned Substituent Group Z.

[Substituent Group Z] is
(1) an optionally substituted hydrocarbon group,
(2) an optionally substituted heterocyclic group,
(3) an optionally substituted $C_{1-6}$ alkoxy group,
(4) an optionally substituted $C_{3-10}$ cycloalkyloxy group,
(5) a halogen atom,
(6) a cyano group,
(7) an optionally substituted amino group,
(8) an optionally substituted $C_{6-14}$ aryloxy group, and
(9) an optionally substituted $C_{1-6}$ alkylthio group.

Examples of the "optionally substituted $C_{1-6}$ alkoxy group" for Substituent Group Z include a $C_{1-6}$ alkoxy group optionally substituted by 1 to 3 substituents selected from Substituent Group A.

Examples of the "optionally substituted $C_{3-10}$ cycloalkyloxy group" for Substituent Group Z include a $C_{3-10}$ cycloalkyloxy group optionally substituted by 1 to 3 substituents selected from Substituent Group A.

Examples of the "optionally substituted $C_{6-14}$ aryloxy group" for Substituent Group Z include a $C_{6-14}$ aryloxy group optionally substituted by 1 to 3 substituents selected from Substituent Group A.

Examples of the "optionally substituted $C_{1-6}$ alkylthio group" for Substituent Group Z include a $C_{1-6}$ alkylthio group optionally substituted by 1 to 3 substituents selected from Substituent Group A.

$R^3$ is preferably a group represented by

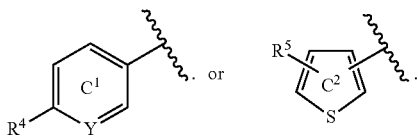

$R^3$ is particularly preferably a group represented by

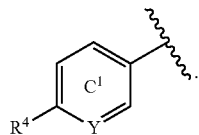

Examples of the "optionally substituted hydrocarbon group" for the "substituent selected from Substituent Group Z" represented by $R^4$ include an optionally substituted $C_{1-6}$ alkyl group (e.g., methyl) and the like.

$R^4$ is preferably
(1) an optionally substituted $C_{1-6}$ alkyl group (e.g., methyl),
(2) an optionally substituted $C_{1-6}$ alkoxy group (e.g., methoxy),
(3) an optionally substituted $C_{3-10}$ cycloalkyloxy group (e.g., cyclopropyloxy), or
(4) a halogen atom (e.g., a chlorine atom).

$R^4$ is more preferably
(1) a $C_{1-6}$ alkyl group (e.g., methyl) optionally substituted by 1 to 3 halogen atoms (e.g., a fluorine atom),
(2) a $C_{1-6}$ alkoxy group (e.g., methoxy) optionally substituted by 1 to 3 halogen atoms (e.g., a fluorine atom),
(3) a $C_{3-10}$ cycloalkyloxy group (e.g., cyclopropyloxy), or
(4) a halogen atom (e.g., a chlorine atom).

$R^4$ is further more preferably a $C_{1-6}$ alkoxy group (e.g., methoxy) optionally substituted by 1 to 3 halogen atoms (e.g., a fluorine atom).

As another embodiment, $R^4$ is preferably
(1) an optionally substituted $C_{1-6}$ alkyl group (e.g., methyl), or
(2) an optionally substituted $C_{1-6}$ alkoxy group (e.g., methoxy).

In this embodiment, $R^4$ is more preferably
(1) a $C_{1-6}$ alkyl group (e.g., methyl) optionally substituted by 1 to 3 halogen atoms (e.g., a fluorine atom), or
(2) a $C_{1-6}$ alkoxy group (e.g., methoxy) optionally substituted by 1 to 3 halogen atoms (e.g., a fluorine atom).

In this embodiment, $R^4$ is further more preferably a $C_{1-6}$ alkoxy group (e.g., methoxy) optionally substituted by 1 to 3 halogen atoms (e.g., a fluorine atom).

Examples of the "optionally substituted hydrocarbon group" for the "substituent selected from Substituent Group Z" represented by $R^5$ include an optionally substituted $C_{1-6}$ alkyl group (e.g., methyl) and the like.

$R^5$ is preferably an optionally substituted $C_{1-6}$ alkyl group (e.g., methyl).

$R^5$ is more preferably a $C_{1-6}$ alkyl group (e.g., methyl) optionally substituted by 1 to 3 halogen atoms (e.g., a fluorine atom).

$R^6$ is preferably a hydrogen atom or a halogen atom (e.g., a fluorine atom).

$R^6$ is more preferably a hydrogen atom.

Y is preferably a nitrogen atom or $CR^6$ wherein $R^6$ is a hydrogen atom or a halogen atom (e.g., a fluorine atom).

Y is more preferably a nitrogen atom or CH.
Y is particularly preferably a nitrogen atom.
Or, Y is particularly preferably CH.

The "benzene ring or pyridine ring" of the "benzene ring or pyridine ring, each of which is optionally further substituted by one substituent selected from Substituent Group Z" represented by Ring $C^1$ is each optionally further substituted by one "substituent selected from Substituent Group Z" at substitutable position, in addition to $R^4$ and $R^6$. Examples of such substituent include a halogen atom (e.g., a fluorine atom, a chlorine atom), an optionally substituted $C_{1-6}$ alkyl group (e.g., methyl), an optionally substituted $C_{1-6}$ alkoxy group (e.g., methoxy) and the like. When the number of the substituents is plural, the respective substituents may be so the same or different.

Ring $C^1$ is preferably a benzene ring (i.e., Y is $CR^6$) or a pyridine ring (i.e., Y is N), each of which is optionally further substituted by one halogen atom (e.g., a fluorine atom, a chlorine atom).

Ring $C^1$ is more preferably a benzene ring (i.e., Y is CH) or a pyridine ring (i.e., Y is N), each of which is optionally further substituted by one halogen atom (e.g., a fluorine atom, a chlorine atom).

Ring $C^1$ is further more preferably a benzene ring (i.e., Y is CH) or a pyridine ring (i.e., Y is N), each of which is optionally further substituted by one halogen atom (e.g., a fluorine atom).

Ring $C^1$ is particularly preferably a pyridine ring (i.e., Y is N) optionally further substituted by one halogen atom (e.g., a fluorine atom).

Or, Ring $C^1$ is particularly preferably a benzene ring (i.e., Y is CH) optionally further substituted by one halogen atom (e.g., a fluorine atom).

The above-mentioned halogen atom as a substituent for Ring $C^1$ is preferably bonded to the carbon atom adjacent to the carbon atom that $R^4$ is bonded to.

The "thiophene ring" of the "thiophene ring optionally further substituted by one substituent selected from Substituent Group Z" represented by Ring $C^2$ is optionally further substituted by one "substituent selected from Substituent Group Z" at substitutable position, in addition to $R^5$. Examples of such substituent include a halogen atom (e.g., a fluorine atom, a chlorine atom), an optionally substituted $C_{1-6}$ alkyl group (e.g., methyl), an optionally substituted $C_{1-6}$ alkoxy group (e.g., methoxy) and the like. When the number of the substituents is plural, the respective substituents may be the same or different.

Ring $C^2$ is preferably a thiophene ring which is not further substituted, namely a thiophene ring substituted by only $R^5$.

Examples of the "optionally substituted methylene group" represented by $L^1$ include a methylene group optionally substituted by 1 to 2 substituents selected from Substituent Group A. When the number of the substituents is plural, the respective substituents may be the same or different.

The "benzene ring, pyridine ring or thiophene ring" of the "benzene ring, pyridine ring or thiophene ring, each of which is optionally further substituted by 1 to 3 substituents selected from Substituent Group Z" represented by Ring $C^3$ is each optionally further substituted by 1 to 3 (preferably 1 or 2) "substituent selected from Substituent Group Z" at substitutable position(s). Examples of such substituent include a halogen atom (e.g., a fluorine atom, a chlorine atom), an optionally substituted $C_{1-6}$ alkyl group (e.g., methyl), an optionally substituted $C_{1-6}$ alkoxy group (e.g., methoxy) and the like. When the number of the substituents is plural, the respective substituents may be the same or different.

Preferable examples of compound (I) include the following compounds.

[Compound Aa-1]

Compound (I) wherein
the group represented by

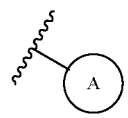

is a group represented by

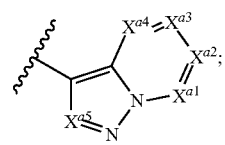

$X^{a1}$ is CH or a nitrogen atom;
$X^{a2}$ is
(1) $CR^a$ wherein $R^a$ is
  (a) a hydrogen atom,
  (b) a halogen atom (e.g., a fluorine atom), or
  (c) an optionally substituted $C_{1-6}$ alkyl group (e.g., methyl), or
(2) a nitrogen atom;
$X^{a3}$ is
(1) $CR^a$ wherein $R^a$ is
  (a) a hydrogen atom, or
  (b) an optionally substituted $C_{1-6}$ alkyl group (e.g., methyl), or
(2) a nitrogen atom;
$X^{a4}$ is
(1) $CR^a$ wherein $R^a$ is
  (a) a hydrogen atom, or
  (b) an optionally substituted $C_{1-6}$ alkyl group (e.g., methyl), or
(2) a nitrogen atom; and
$X^{a5}$ is
(1) $CR^a$ wherein $R^a$ is
  (a) a hydrogen atom,
  (b) an optionally substituted $C_{1-6}$ alkyl group (e.g., methyl, ethyl),
  (c) an optionally substituted $C_{1-6}$ alkoxy group (e.g., ethoxy), or
  (d) an optionally substituted $C_{3-10}$ cycloalkyl group (e.g., cyclopropyl), or
(2) a nitrogen atom;
provided that when $X^{a5}$ is $CR^a$, then at least one of $X^{a1}$, $X^{a2}$ and $X^{a3}$ is a nitrogen atom;
[preferably a group represented by

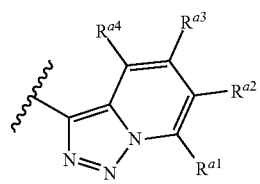 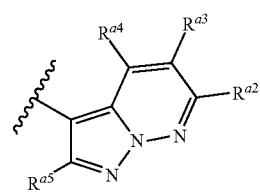

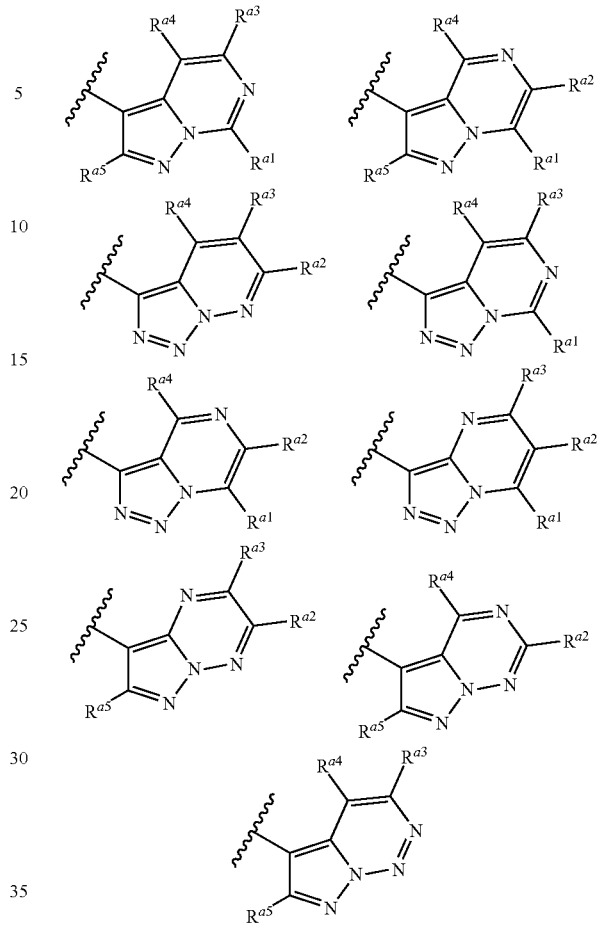

wherein
$R^{a1}$ is a hydrogen atom;
$R^{a2}$ is
(a) a hydrogen atom,
(b) a halogen atom (e.g., a fluorine atom), or
(c) an optionally substituted $C_{1-6}$ alkyl group (e.g., methyl);
$R^{a3}$ is
(a) a hydrogen atom, or
(b) an optionally substituted $C_{1-6}$ alkyl group (e.g., methyl);
$R^{a4}$ is
(a) a hydrogen atom, or
(b) an optionally substituted $C_{1-6}$ alkyl group (e.g., methyl); and
$R^{a5}$ is
(a) a hydrogen atom,
(b) an optionally substituted $C_{1-6}$ alkyl group (e.g., methyl, ethyl),
(c) an optionally substituted $C_{1-6}$ alkoxy group (e.g., ethoxy), or
(d) an optionally substituted $C_{3-10}$ cycloalkyl group (e.g., cyclopropyl)]

$R^1$ and $R^2$ are each independently a hydrogen atom or a $C_{1-6}$ alkyl group optionally substituted by fluorine atom(s); and $R^3$ is a group represented by

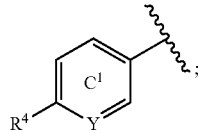

$R^4$ is
(1) an optionally substituted $C_{1-6}$ alkyl group (e.g., methyl),
(2) an optionally substituted $C_{1-6}$ alkoxy group (e.g., methoxy),
(3) an optionally substituted $C_{3-10}$ cycloalkyloxy group (e.g., cyclopropyloxy), or
(4) a halogen atom (e.g., a chlorine atom) (preferably
(1) an optionally substituted $C_{1-6}$ alkyl group (e.g., methyl), or
(2) an optionally substituted $C_{1-6}$ alkoxy group (e.g., methoxy));
Y is a nitrogen atom or $CR^6$ wherein $R^6$ is a hydrogen atom or a halogen atom (e.g., a fluorine atom)); and
Ring $C^1$ is a benzene ring (i.e., Y is $CR^6$) or a pyridine ring (i.e., Y is N), each of which is optionally further substituted by one halogen atom (e.g., a fluorine atom, a chlorine atom).
[Compound Ba-1]
The above-mentioned [Compound Aa-1] wherein the group represented by

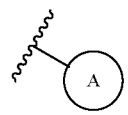

is a group represented by

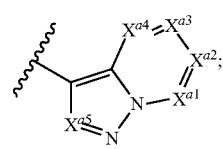

$X^{a1}$ is CH or a nitrogen atom;
$X^{a2}$ is
(1) $CR^a$ wherein $R^a$ is
  (a) a hydrogen atom,
  (b) a halogen atom (e.g., a fluorine atom), or
  (c) a $C_{1-6}$ alkyl group (e.g., methyl), or
(2) a nitrogen atom;
$X^{a3}$ is
(1) $CR^a$ wherein $R^a$ is
  (a) a hydrogen atom, or
  (b) a $C_{1-6}$ alkyl group (e.g., methyl), or
(2) a nitrogen atom;
$X^{a4}$ is
(1) $CR^a$ wherein $R^a$ is
  (a) a hydrogen atom, or
  (b) a $C_{1-6}$ alkyl group (e.g., methyl), or
(2) a nitrogen atom; and
$X^{a5}$ is
(1) $CR^a$ wherein $R^a$ is
  (a) a hydrogen atom,
  (b) a $C_{1-6}$ alkyl group (e.g., methyl, ethyl) optionally substituted by 1 to 3 (preferably 1 to 2) substituents selected from a halogen atom (e.g., a fluorine atom) and a $C_{1-6}$ alkoxy group (e.g., methoxy),
  (c) a $C_{1-6}$ alkoxy group (e.g., ethoxy), or
  (d) a $C_{3-10}$ cycloalkyl group (e.g., cyclopropyl), or
(2) a nitrogen atom;
provided that when $X^{a5}$ is $CR^a$, then at least one of $X^{a1}$, $X^{a2}$ and $X^{a3}$ is a nitrogen atom;
[preferably a group represented by (a)
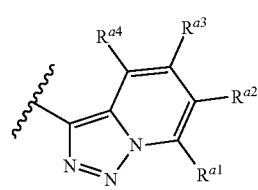

(b)
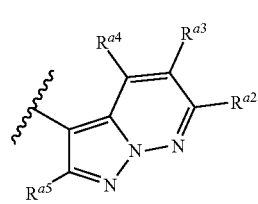

(c)
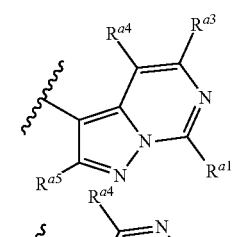

(d)
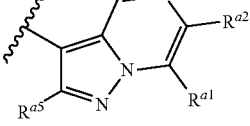

(e)
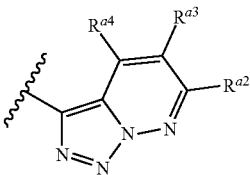

(f)
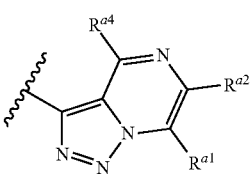

(g)
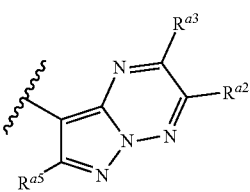

wherein

R$^{a1}$ is a hydrogen atom;

R$^{a2}$ is (a) a hydrogen atom, (b) a halogen atom (e.g., a fluorine atom), or (c) a C$_{1-6}$ alkyl group (e.g., methyl);

R$^{a3}$ is (a) a hydrogen atom, or (b) a C$_{1-6}$ alkyl group (e.g., methyl);

R$^{a4}$ is (a) a hydrogen atom, or (b) a C$_{1-6}$ alkyl group (e.g., methyl); and R$^{a5}$ is (a) a hydrogen atom, (b) a C$_{1-6}$ alkyl group (e.g., methyl, ethyl) optionally substituted by 1 to 3 (preferably 1 to 2) substituents selected from a halogen atom (e.g., a fluorine atom) and a C$_{1-6}$ alkoxy group (e.g., methoxy), (c) a C$_{1-6}$ alkoxy group (e.g., ethoxy), or (d) a C$_{3-10}$ cycloalkyl group (e.g., cyclopropyl)]

R$^1$ and R$^2$ are both hydrogen atoms; and

R$^4$ is (1) a C$_{1-6}$ alkyl group (e.g., methyl) optionally substituted by 1 to 3 halogen atoms (e.g., a fluorine atom), (2) a C$_{1-6}$ alkoxy group (e.g., methoxy) optionally substituted by 1 to 3 halogen atoms (e.g., a fluorine atom), (3) a C$_{3-10}$ cycloalkyloxy group (e.g., cyclopropyloxy), or (4) a halogen atom (e.g., a chlorine atom) (preferably (1) a C$_{1-6}$ alkyl group (e.g., methyl) optionally substituted by 1 to 3 halogen atoms (e.g., a fluorine atom), or (2) a C$_{1-6}$ alkoxy group (e.g., methoxy)optionally substituted by 1 to 3 halogen atoms (e.g., a fluorine atom)).

[Compound Ca-1]

The above-mentioned [Compound Ba-1] wherein the group represented by

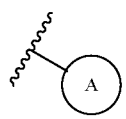

is a group represented by

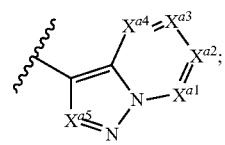

X$^{a1}$ is CH or a nitrogen atom;

X$^{a2}$ is CH;

X$^{a3}$ is CH or a nitrogen atom;

X$^{a4}$ is CH; and

X$^{a5}$ is CH or a nitrogen atom;

provided that when X$^{a5}$ is CH, then at least one of X$^{a1}$ and X$^{a3}$ is a nitrogen atom;

[preferably a group represented by

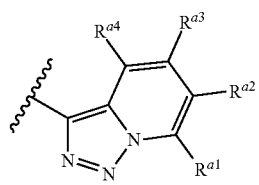

(a)

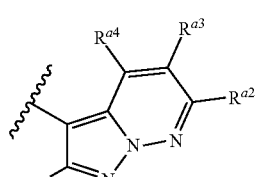

(b)

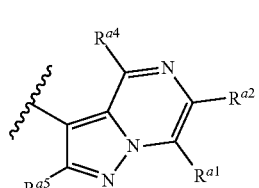

(d)

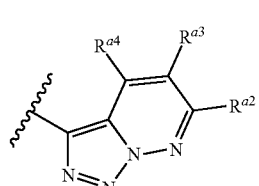

(e)

wherein R$^{a1}$, R$^{a2}$, R$^{a3}$, R$^{a4}$ and R$^{a5}$ are all hydrogen atoms]

R$^4$ is a C$_{1-6}$ alkoxy group (e.g., methoxy) optionally substituted by 1 to 3 halogen atoms (e.g., a fluorine atom); and Y is a nitrogen atom or CR$^6$ wherein R$^6$ is a hydrogen atom.

[Compound Ab-1]

Compound (I) wherein the group represented by

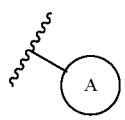

is a group represented by

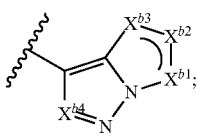

X$^{b1}$ is CH;

X$^{b2}$ is CH;

$X^{b3}$ is a nitrogen atom optionally substituted by an optionally substituted $C_{1-6}$ alkyl groups (e.g., methyl); and
$X^{b4}$ is CH;
[i.e., a group represented by

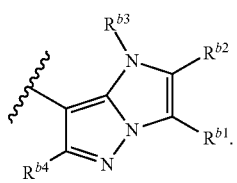

(h)

wherein
$R^{b1}$ is a hydrogen atom;
$R^{b2}$ is a hydrogen atom;
$R^{b3}$ is a hydrogen atom or an optionally substituted $C_{1-6}$ alkyl group (e.g., methyl); and
$R^{b4}$ is a hydrogen atom]
$R^1$ and $R^2$ are each independently a hydrogen atom or a $C_{1-6}$ alkyl group optionally substituted by fluorine atom(s); and
$R^3$ is a group represented by

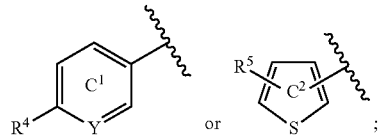

$R^4$ is
(1) an optionally substituted $C_{1-6}$ alkyl group (e.g., methyl),
(2) an optionally substituted $C_{1-6}$ alkoxy group (e.g., methoxy),
(3) an optionally substituted $C_{3-10}$ cycloalkyloxy group (e.g., cyclopropyloxy), or
(4) a halogen atom (e.g., a chlorine atom);
Y is a nitrogen atom or $CR^6$ wherein $R^6$ is a hydrogen atom or a halogen atom (e.g., a fluorine atom)); and
Ring $C^1$ is a benzene ring (i.e., Y is $CR^6$) or a pyridine ring (i.e., Y is N), each of which is optionally further substituted by one halogen atom (e.g., a fluorine atom, a chlorine atom);
$R^5$ is an optionally substituted $C_{1-6}$ alkyl group (e.g., methyl); and
Ring $C^2$ is a thiophene ring substituted by only $R^5$.
[Compound Bb-1]
The above-mentioned [Compound Ab-1] wherein
$X^{b3}$ is a nitrogen atom optionally substituted by a $C_{1-6}$ alkyl group (e.g., methyl);
[i.e., $R^{b3}$ is a hydrogen atom or a $C_{1-6}$ alkyl group (e.g., methyl)]
$R^1$ and $R^2$ are both hydrogen atoms;
$R^4$ is
(1) a $C_{1-6}$ alkyl group (e.g., methyl) optionally substituted by 1 to 3 halogen atoms (e.g., a fluorine atom),
(2) a $C_{1-6}$ alkoxy group (e.g., methoxy) optionally substituted by 1 to 3 halogen atoms (e.g., a fluorine atom),
(3) a $C_{3-10}$ cycloalkyloxy group (e.g., cyclopropyloxy), or
(4) a halogen atom (e.g., a chlorine atom); and
$R^5$ is a $C_{1-6}$ alkyl group (e.g., methyl) optionally substituted by 1 to 3 halogen atoms (e.g., a fluorine atom).

[Compound Cb-1]
The above-mentioned [Compound Bb-1] wherein
$R^3$ is a group represented by

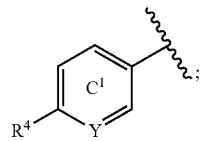

$R^4$ is a $C_{1-6}$ alkoxy group (e.g., methoxy) optionally substituted by 1 to 3 halogen atoms (e.g., a fluorine atom);
Y is a nitrogen atom or $CR^6$ wherein $R^6$ is a hydrogen atom; and
Ring $C^1$ is a pyridine ring (i.e., Y is N) optionally further substituted by one halogen atom (e.g., a fluorine atom).
[Compound A-2]
Compound (I) wherein
the group represented by

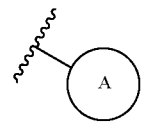

is a group represented by

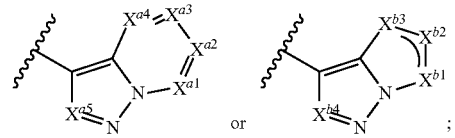

$X^{a1}$ is CH or a nitrogen atom;
$X^{a2}$ is
(1) $CR^a$ wherein $R^a$ is
  (a) a hydrogen atom,
  (b) a halogen atom (e.g., a fluorine atom), or
  (c) an optionally substituted $C_{1-6}$ alkyl group (e.g., methyl), or
(2) a nitrogen atom;
$X^{a3}$ is
(1) $CR^a$ wherein $R^a$ is
  (a) a hydrogen atom, or
  (b) an optionally substituted $C_{1-6}$ alkyl group (e.g., methyl), or
(2) a nitrogen atom;
$X^{a4}$ is
(1) $CR^a$ wherein $R^a$ is
  (a) a hydrogen atom, or
  (b) an optionally substituted $C_{1-6}$ alkyl group (e.g., methyl), or
(2) a nitrogen atom; and
$X^{a5}$ is
(1) $CR^a$ wherein $R^a$ is
  (a) a hydrogen atom,
  (b) an optionally substituted $C_{1-6}$ alkyl group (e.g., methyl, ethyl),
  (c) an optionally substituted $C_{1-6}$ alkoxy group (e.g., ethoxy), or (d) an optionally substituted $C_{3-10}$ cycloalkyl group (e.g., cyclopropyl), or
(2) a nitrogen atom;
provided that when $X^{a5}$ is $CR^a$, then at least one of $X^{a1}$, $X^{a2}$ and $X^{a3}$ is a nitrogen atom;
$X^{b1}$ is CH or a nitrogen atom;
$X^{b2}$ is $CR^b$ wherein $R^b$ is
 (a) a hydrogen atom, or
 (b) an optionally substituted $C_{1-6}$ alkyl group (e.g., methyl);
$X^{b3}$ is a nitrogen atom optionally substituted by an optionally substituted $C_{1-6}$ alkyl group (e.g., methyl, ethyl); and
$X^{b4}$ is $CR^b$ wherein $R^b$ is
 (a) a hydrogen atom, or
 (b) an optionally substituted $C_{1-6}$ alkyl group (e.g., methyl);
$R^1$ and $R^2$ are each independently a hydrogen atom or a $C_{1-6}$ alkyl group optionally substituted by fluorine atom(s); and
$R^3$ is a group represented by,

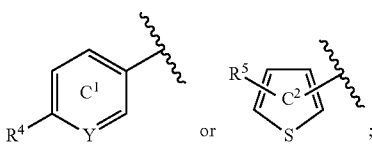

$R^4$ is
(1) an optionally substituted $C_{1-6}$ alkyl group (e.g., methyl),
(2) an optionally substituted $C_{1-6}$ alkoxy group (e.g., methoxy),
(3) an optionally substituted $C_{3-10}$ cycloalkyloxy group (e.g., cyclopropyloxy), or
(4) a halogen atom (e.g., a chlorine atom);
Y is a nitrogen atom or $CR^6$ wherein $R^6$ is a hydrogen atom or a halogen atom (e.g., a fluorine atom)); and
Ring $C^1$ is a benzene ring (i.e., Y is $CR^6$) or a pyridine ring (i.e., Y is N), each of which is optionally further substituted by one halogen atom (e.g., a fluorine atom, a chlorine atom);
$R^5$ is an optionally substituted $C_{1-6}$ alkyl group (e.g., methyl); and
Ring $C^2$ is a thiophene ring substituted by only $R^5$.
[Compound B-2]
 Compound (I) wherein
the group represented by

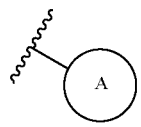

is a group represented by

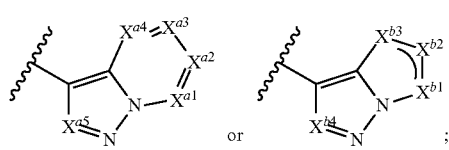

$X^{a1}$ is CH or a nitrogen atom;
$X^{a2}$ is
(1) $CR^a$ wherein $R^a$ is
 (a) a hydrogen atom,
 (b) a halogen atom (e.g., a fluorine atom), or
 (c) a $C_{1-6}$ alkyl group (e.g., methyl), or
(2) a nitrogen atom;
$X^{a3}$ is
(1) $CR^a$ wherein $R^a$ is
 (a) a hydrogen atom, or
 (b) a $C_{1-6}$ alkyl group (e.g., methyl), or
(2) a nitrogen atom;
$X^{a4}$ is
(1) $CR^a$ wherein $R^a$ is
 (a) a hydrogen atom, or
 (b) a $C_{1-6}$ alkyl group (e.g., methyl), or
(2) a nitrogen atom; and
$X^{a5}$ is
(1) $CR^a$ wherein $R^a$ is
 (a) a hydrogen atom,
 (b) a $C_{1-6}$ alkyl group (e.g., methyl, ethyl) optionally substituted by 1 to 3 (preferably 1 to 2) substituents selected from a halogen atom (e.g., a fluorine atom) and a $C_{1-6}$ alkoxy group (e.g., methoxy),
 (c) a $C_{1-6}$ alkoxy group (e.g., ethoxy), or
 (d) a $C_{3-10}$ cycloalkyl group (e.g., cyclopropyl), or
(2) a nitrogen atom;
provided that when $X^{a5}$ is $CR^a$, then at least one of $X^{a1}$, $X^{a2}$ and $X^{a3}$ is a nitrogen atom;
(preferably a group represented by

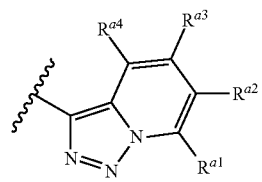
(a)

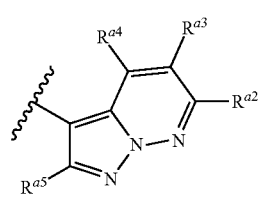
(b)

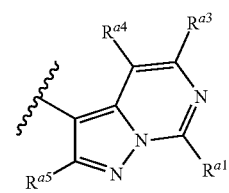
(c)

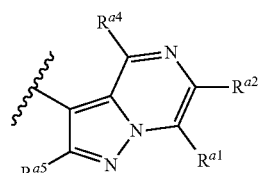
(d)

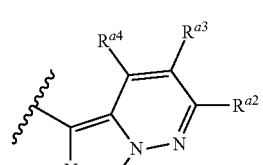
(e)

-continued

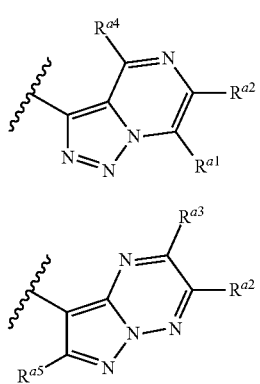

wherein
$R^{a1}$ is a hydrogen atom;
$R^{a2}$ is
(a) a hydrogen atom,
(b) a halogen atom (e.g., a fluorine atom), or
(c) a $C_{1-6}$ alkyl group (e.g., methyl);
$R^{a3}$ is
(a) a hydrogen atom, or
(b) a $C_{1-6}$ alkyl group (e.g., methyl);
$R^{a4}$ is
(a) a hydrogen atom, or
(b) a $C_{1-6}$ alkyl group (e.g., methyl); and
$R^{a5}$ is
(a) a hydrogen atom,
(b) a $C_{1-6}$ alkyl group (e.g., methyl, ethyl) optionally substituted by 1 to 3 (preferably 1 to 2) substituents selected from a halogen atom (e.g., a fluorine atom) and a $C_{1-6}$ alkoxy group (e.g., methoxy),
(c) a $C_{1-6}$ alkoxy group (e.g., ethoxy), or
(d) a $C_{3-10}$ cycloalkyl group (e.g., cyclopropyl);
$X^{b1}$ is CH or a nitrogen atom;
$X^{b2}$ is $CR^b$ wherein $R^b$ is
  (a) a hydrogen atom, or
  (b) a $C_{1-6}$ alkyl group (e.g., methyl);
$X^{b3}$ is a nitrogen atom optionally substituted by a $C_{1-6}$ alkyl group (e.g., methyl, ethyl) optionally substituted by 1 to 3 halogen atoms (e.g., a fluorine atom); and
$X^{b4}$ is $CR^b$ wherein $R^b$ is
  (a) a hydrogen atom, or
  (b) a $C_{1-6}$ alkyl group (e.g., methyl);
[preferably a group represented by

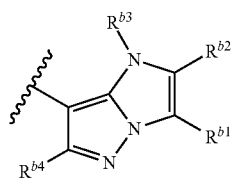

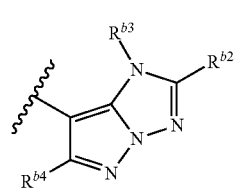

wherein
(f) $R^{b1}$ is a hydrogen atom;
$R^{b2}$ is a hydrogen atom or a $C_{1-6}$ alkyl group (e.g., methyl);
$R^{b3}$ is a hydrogen atom or a $C_{1-6}$ alkyl group (e.g., methyl, ethyl) optionally substituted by 1 to 3 halogen atoms (e.g., a fluorine atom); and
$R^{b4}$ is a hydrogen atom or a $C_{1-6}$ alkyl group (e.g., methyl)]
(g) $R^1$ and $R^2$ are both hydrogen atoms; and
$R^3$ is a group represented by

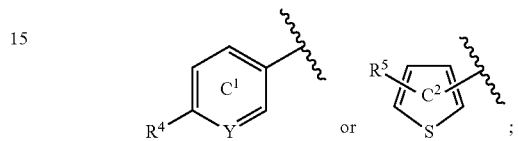

$R^4$ is
(1) a $C_{1-6}$ alkyl group (e.g., methyl) optionally substituted by 1 to 3 halogen atoms (e.g., a fluorine atom),
(2) a $C_{1-6}$ alkoxy group (e.g., methoxy) optionally substituted by 1 to 3 halogen atoms (e.g., a fluorine atom),
(3) a $C_{3-10}$ cycloalkyloxy group (e.g., cyclopropyloxy), or
(4) a halogen atom (e.g., a chlorine atom);
Y is a nitrogen atom or $CR^6$ wherein $R^6$ is a hydrogen atom or a halogen atom (e.g., a fluorine atom)); and
Ring $C^1$ is a benzene ring (i.e., Y is $CR^6$) or a pyridine ring (i.e., Y is N), each of which is optionally further substituted by one halogen atom (e.g., a fluorine atom, a chlorine atom);
$R^5$ is a $C_{1-6}$ alkyl group (e.g., methyl) optionally substituted by 1 to 3 halogen atoms (e.g., a fluorine atom); and
Ring $C^2$ is a thiophene ring substituted by only $R^5$.
[Compound C-2]
Compound (I) wherein
the group represented by

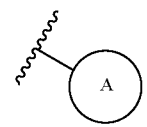

(h) is a group represented by

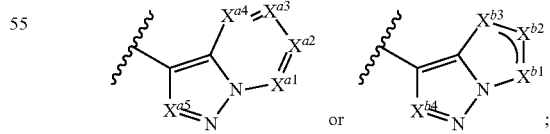

(i)
$X^{a1}$ is CH or a nitrogen atom;
$X^{a2}$ is CH;
$X^{a3}$ is CH or a nitrogen atom;
$X^{a4}$ is CH; and
$X^{a5}$ is CH or a nitrogen atom;

provided that when $X^{a5}$ is CH, then at least one of $X^{a1}$ and $X^{a3}$ is a nitrogen atom;
[preferably a group represented by

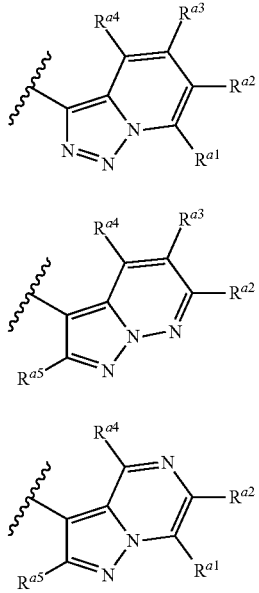

wherein $R^{a1}$, $R^{a2}$, $R^{a3}$, $R^{a4}$ and $R^{a5}$ are all hydrogen atoms]
$X^{b1}$ is CH;
$X^{b2}$ is CH;
$X^{b3}$ is a nitrogen atom optionally substituted by a $C_{1-6}$ alkyl group (e.g., methyl); and
$X^{b4}$ is CH;
[i.e., a group represented by

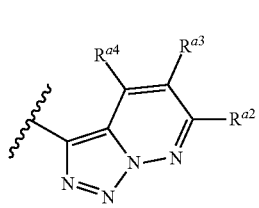

wherein
$R^{b1}$ is a hydrogen atom;
$R^{b2}$ is a hydrogen atom;
$R^{b3}$ is a hydrogen atom or a $C_{1-6}$ alkyl group (e.g., methyl); and
$R^{b4}$ is a hydrogen atom]
$R^1$ and $R^2$ are both hydrogen atoms; and
$R^3$ is a group represented by

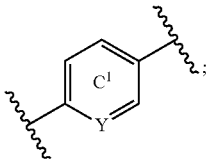

$R^4$ is a $C_{1-6}$ alkoxy group (e.g., methoxy) optionally substituted by 1 to 3 halogen atoms (e.g., a fluorine atom);
Y is a nitrogen atom or CH; and
Ring $C^1$ is a benzene ring (i.e., Y is CH) or a pyridine ring (i.e., Y is N), each of which is optionally further substituted by one halogen atom (e.g., a fluorine atom, a chlorine atom).
[Compound D-2]
Compound (I) wherein
the group represented by

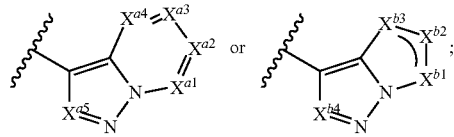

is a group represented by

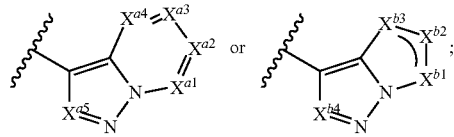

$X^{a1}$ is CH or a nitrogen atom;
$X^{a2}$ is CH;
$X^{a3}$ is CH;
$X^{a4}$ is CH; and
$X^{a5}$ is CH or a nitrogen atom;
provided that when $X^{a5}$ is CH, then $X^{a1}$ is a nitrogen atom;
[i.e., a group represented by

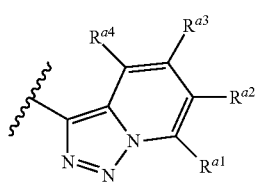

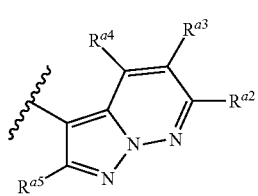

wherein $R^{a1}$, $R^{a2}$, $R^{a3}$, $R^{a4}$ and $R^{a5}$ are all hydrogen atoms]
$X^{b1}$ is CH;
$X^{b2}$ is CH;

$X^{b3}$ is a nitrogen atom optionally substituted by a $C_{1-6}$ alkyl group (e.g., methyl); and
$X^{b4}$ is CH;
[i.e., a group represented by

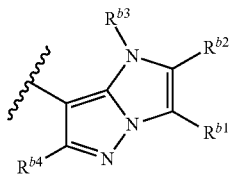

(h)

wherein
$R^{b1}$ is a hydrogen atom;
$R^{b2}$ is a hydrogen atom;
$R^{b3}$ is a hydrogen atom or a $C_{1-6}$ alkyl group (e.g., methyl); and
$R^{b4}$ is a hydrogen atom]
$R^1$ and $R^2$ are both hydrogen atoms; and
$R^3$ is a group represented by

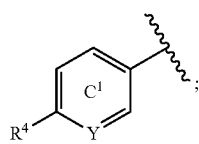

$R^4$ is a $C_{1-6}$ alkoxy group (e.g., methoxy) optionally substituted by 1 to 3 halogen atoms (e.g., a fluorine atom);
Y is a nitrogen atom or CH; and
Ring $C^1$ is a benzene ring (i.e., Y is CH) or a pyridine ring (i.e., Y is N), each of which is optionally further substituted by one halogen atom (e.g., a fluorine atom).
[Compound E-2]
Compound (I) wherein
the group represented by

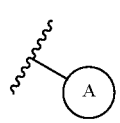

is a group represented by

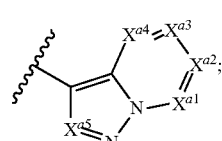

$X^{a1}$ is a nitrogen atom;
$X^{a2}$ is CH;
$X^{a3}$ is CH;

$X^{a4}$ is CH; and
$X^{a5}$ is CH;
[i.e., a group represented by

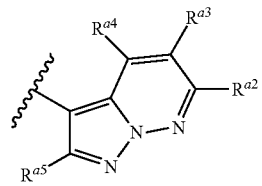

(b)

wherein $R^{a2}$, $R^{a3}$, $R^{a4}$ and $R^{a5}$ are all hydrogen atoms]
$R^1$ and $R^2$ are both hydrogen atoms; and
$R^3$ is a group represented by

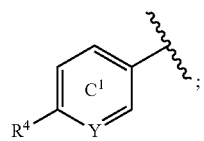

$R^4$ is a $C_{1-6}$ alkoxy group (e.g., methoxy) optionally substituted by 1 to 3 halogen atoms (e.g., a fluorine atom);
Y is a nitrogen atom; and
Ring $C^1$ is a pyridine ring (i.e., Y is N) optionally further substituted by one halogen atom (e.g., a fluorine atom).
[Compound F-2]
Compound (I) wherein
the group represented by

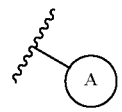

is a group represented by

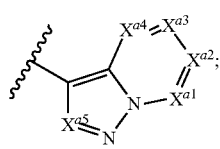

$X^{a1}$ is CH;
$X^{a2}$ is CH;
$X^{a3}$ is CH;
$X^{a4}$ is CH; and
$X^{a5}$ is a nitrogen atom;
[i.e., a group represented by

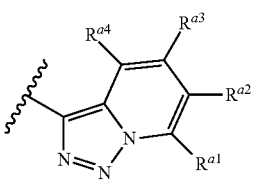

(a)

wherein $R^{a1}$, $R^{a2}$, $R^{a3}$ and $R^{a4}$ are all hydrogen atoms]

$R^1$ and $R^2$ are both hydrogen atoms; and $R^3$ is a group represented by

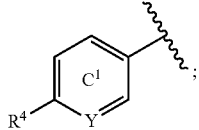

$R^4$ is a $C_{1-6}$ alkoxy group (e.g., methoxy) optionally substituted by 1 to 3 halogen atoms (e.g., a fluorine atom);

Y is CH; and

Ring $C^1$ is a benzene ring (i.e., Y is CH) optionally further substituted by one halogen atom (e.g., a fluorine atom).

[Compound G-2]

Compound (I) wherein the group represented by

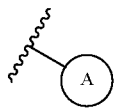

is a group represented by

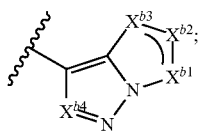

$X^{b1}$ is CH;

$X^{b2}$ is CH;

$X^{b3}$ is a nitrogen atom optionally substituted by a $C_{1-6}$ alkyl group (e.g., methyl); and $X^{b4}$ is CH;

[i.e., a group represented by

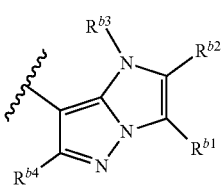

(h)

wherein $R^{b1}$ is a hydrogen atom;

$R^{b2}$ is a hydrogen atom;

$R^{b3}$ is a hydrogen atom or a $C_{1-6}$ alkyl group (e.g., methyl); and $R^{b4}$ is a hydrogen atom]

$R^1$ and $R^2$ are both hydrogen atoms; and $R^3$ is a group represented by

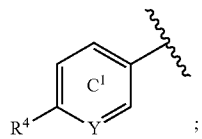

$R^4$ is a $C_{1-6}$ alkoxy group (e.g., methoxy) optionally substituted by 1 to 3 halogen atoms (e.g., a fluorine atom);

Y is a nitrogen atom; and

Ring $C^1$ is a pyridine ring (i.e., Y is N) optionally further substituted by one halogen atom (e.g., a fluorine atom).

[Compound H]

6-(difluoromethoxy)-5-fluoro-N-[(pyrazolo[1,5-b]pyridazin-3-yl)methyl]pyridine-3-carboxamide or a salt thereof. 3-fluoro-N-[([1,2,3]triazolo[1,5-a]pyridin-3-yl)methyl]-4-(trifluoromethoxy)benzamide or a salt thereof. 6-(difluoromethoxy)-5-fluoro-N-[1-methyl-1H-imidazo[1,2-b]pyrazol-7-yl)methyl]pyridine-3-carboxamide or a salt thereof.

Specific examples of compound (I) include the compounds of the below-mentioned Examples 1 to 85.

As a salt of a compound represented by the formula (I), a pharmacologically acceptable salt is preferable, and examples of such salt include a salt with inorganic base, a salt with organic base, a salt with inorganic acid, a salt with organic acid, and a salt with basic or acidic amino acid.

Preferable examples of the salt with inorganic base include alkali metal salts such as sodium salt, potassium salt and the like; alkaline earth metal salts such as calcium salt, magnesium salt and the like; aluminum salt; and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, and N,N-dibenzylethylenediamine.

Preferable examples of the salt with inorganic acid include salts with hydrogen chloride, hydrogen bromide, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

Compound (I) may be used as a prodrug.

The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, or t-butylation);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation);

a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like). Any of these compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, a prodrug may form a salt, and examples of as such salt include those exemplified as a salt of the compound represented by the aforementioned formula (I).

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and may be useful in the field of medical diagnosis and the like.

Furthermore, compound (I) may be a hydrate or a non-hydrate, or a non-solvate, or a solvate.

Compound (I) also encompasses a deuterium conversion form wherein $^1$H is converted to $^2$H(D).

Furthermore, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, and stability). The cocrystal and cocrystal salt can be produced by cocrystallization method known per se.

Compound (I) or a prodrug thereof (hereinafter sometimes to be simply abbreviated as the compound of the present invention) may be used as it is or in the form of a pharmaceutical composition (hereinafter sometimes to be abbreviated as the "medicament of the present invention") by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials may be used. These may be incorporated as excipient, lubricant, binder and disintegrant for solid preparations; or solvent, solubilizing agent, suspending agent, isotonicity agent, buffer and soothing agent for liquid preparations; and the like. Where necessary, preparation additives such as preservative, antioxidant, colorant, sweetening agent and the like may also be used.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the aforementioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the medicament of the present invention include oral preparations such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film); and parenteral preparations such as injection (e.g., subcutaneous injection, intravenous injection, intramuscular injection, intraperitoneal injection, drip infusion), external preparation (e.g. transdermal absorption type preparation, ointment, lotion, adhesive preparation), suppository (e.g., rectal suppository, vaginal suppository), pellet, nasal preparation, pulmonary preparation (inhalant), eye drop. The compound of the present invention and the medicament of the present invention may be administered orally or parenterally (e.g., intravenous, intraarterial, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be a release control preparation (e.g., sustained-release microcapsule) such as an immediate-release preparation, a sustained-release preparation and the like.

The medicament of the present invention may be produced according to a method conventionally used in the field of pharmaceutical formulation, for example, the method described in the Japanese Pharmacopoeia, and the like.

While the content of the compound of the present invention in the medicament of the present invention varies depending on the dosage form, dose of the compound of the present invention and the like, it may be, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, precipitated calcium carbonate, gelatin, gum arabic, pullulan, and carnauba wax may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, and red ferric oxide may also be used during coating.

The compound of the present invention has an antagonistic action on an NMDA receptor containing the NR2B subunit. Here, the antagonistic action on an NMDA receptor containing the NR2B subunit is confirmed, for example, by inhibitory effect on the receptor activation (e.g., glutamete-induced intracellular calcium ion ($Ca^{2+}$) influx).

The NMDA receptor containing the NR2B subunit is a receptor composed of total four subunits containing one NR2B subunit, and further containing 2 to 3 kinds of three subunits selected from NR1, NR2A, NR2B, NR2C, NR2D, NR3A and NR3B.

The NMDA receptor containing the NR2B subunit is preferably a receptor composed of four subunits consisting of heterodimer of NR1 and NR2B, and heterodimer of NR1 and one subunit selected from NR2A, NR2B, NR2C and NR2D.

The NMDA receptor containing the NR2B subunit is more preferably a receptor composed of four subunits consisting of two sets of heterodimers of NR1 and NR2B.

Since the compound of the present invention is expected to show low toxicity (e.g., acute toxicity, chronic toxicity, genetic toxicity, reproductive toxicity, pulmonary toxicity, carcinogenicity) and less side effects, it may be used as a prophylactic or therapeutic agent, or diagnostic agent for various diseases in mammals.

The compound of the present invention is expected to show low mutagenicity in Ames test, and low hERG (human Ether-a-go-go Related Gene) inhibitory action. Moreover, The compound of the present invention is expected to show low extracerebral excretion via BCRP (Breast Cancer Resistance Protein) transporter, and to be superior in stability to conjugation metabolism.

The compound of the present invention may be used as a prophylactic or therapeutic agent for central and peripheral diseases. For example, it may be useful as an agent for the prophylaxis or treatment of various diseases such as (1) psychiatric diseases [e.g., depression, major depression, minor depressive disorder, bipolar depression, dysthymic disorder, emotional disorder (seasonal affective disorder and the like), recurrent depression, postpartum depression, stress disorder, major depressive disorder concomitant with psychosis (including delusional disorders and schizophrenia), manic or mixed mood episode, hypomanic mood episode, depression episode with atypical features, depression episode with melancholic features, depressive episodes with tonic features, depression episode after stroke, delirium, behavioral and psychological symptoms of dementia (psychiatric symptom or behavior abnormalities), anxiety, generalized anxiety disorder, anxiety syndrome, mood disorder, cyclothymic disorder, premenstrual dysphoric disorder, panic disorder, phobia, social phobia, social anxiety disorder, obsessive disorder, post-traumatic stress syndrome, post-traumatic stress disorder, delusions or depression-type schizoaffective disorder, delusive personality disorder, Tourette syndrome, autism, fragile X syndrome, Rett syndrome, adjustment disorder, bipolar disorder (including type I bipolar disorder and type II bipolar disorder), neurosis, schizophrenia (e.g., positive symptom, negative symptom, memory disorders, delusional schizophrenia, disorganized schizophrenia, tension type schizophrenia, undifferentiated schizophrenia, remnant type schizophrenia), schizophreniform disorder, chronic fatigue syndrome, anxiety neurosis, compulsive neurosis, panic disorder, epilepsy, rare epilepsy (Dravet syndrome, Lennox-Gastaut syndrome, cyclin-dependent kinase-like (CDKL5) genetic mutation syndrome, 15q duplication syndrome, epileptic encephalopathy, etc.), anxiety, anxious mental state, emotional abnormality, cyclothymia, nervous erethism, faint, addiction, low sex drive, attention deficit hyperactivity disorder (ADHD), refractory major depression, treatment-resistant depression, psychotic disturbance (e.g., short-term psychotic disorder, shared psychotic disorder), psychosis induced by alcohol, amphetamine, cannabis, cocaine, hallucinogen, obesity, inhalation medicine, opioids or phencyclidine, delusional disorder, Noonan syndrome, Angelman syndrome, Prader-Willi syndrome, Beckwith-Wiedemann syndrome, Silver-Russell syndrome, tuberous sclerosis, Williams syndrome, Kallmann syndrome, Rubinstein-Taybi syndrome], movement disorder, mental retardation, paranoid tendency, (2) neurodegenerative diseases (e.g., Alzheimer's disease, Alzheimer-type senile dementia, Parkinson's disease, Huntington's disease, multi-infarct dementia, frontotemporal dementia, frontotemporal dementia Parkinson's Type, alcoholic dementia or other drug related dementia, dementia associated with intracranial tumor or brain trauma, Dementia associated with Huntington's disease or Parkinson's disease, neurodegeneration accompanying brain trauma, neurodegeneration accompanying stroke, neurodegeneration accompanying cerebral infarction, neurodegeneration associated with hypoglycemia, neurodegeneration accompanying epileptic seizures, neurodegeneration accompanying neurotoxicosis, multiple system atrophy, spinal cord injury, AIDS-related dementia, progressive supranuclear palsy, Pick's syndrome, Niemann-Pick syndrome, corticobasal degeneration, Down's syndrome, vascular dementia, post-encephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, neuromyopathy], (3) amnestic disorder, mild cognitive impairment, learning disability (e.g., reading disturbance, arithmetic disorder, dysgraphia), age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) pain [e.g., psychogenic pain (somatoform disorder, pain disorder, somatization disorder, hypochondriasis, conversion disorder, chronic pain accompanied by depression), inflammatory pain, peripheral neuropathic pain, central neuropathic pain, neuropathic pain, acute pain, intractable pain, cancerous continuous pain, cancerous breakthrough pain, cancer pain, continuous pain, physical pain, breakthrough pain, chronic pain, tenderness, generalized pain, dull pain, dermatological pain, radiation pain, pain, postoperative thoracotomy pain syndrome], (7) Hearing loss or deafness (e.g., kanamycin deafness, streptomycin deafness, toxic deafness, senile deafness, idiopathic bilateral sensorineural hearing loss, sudden deafness, acquired deaf mutism, genetic deafness, organic deafness, high-tone sensorineural hearing loss, occupational hearing loss, occupational deafness, low-tone sensorineural hearing loss], (8) traumatic brain injury, and disorder or complication associated therewith, post concussive syndrome, shaken baby syndrome, cerebral apoplexy, age-related macular degeneration, oculopalatal tremor, convulsions, phantom limb pain, radiation somnolence syndrome, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug abuse, drug dependence, drug withdrawal, migraine, stress headache, catatonic headache, diabetic neuropathy, obesity, diabetes, muscular convulsions, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, diarrhea, constipation, postoperative ileus, and the like.

Particularly, the compound of the present invention may be useful for the prophylaxis or treatment of major depression, bipolar disorder, migraine, pain or behavioral and psychological symptoms of dementia.

Both major depression and bipolar disorder are classified as mood disorder, and are diseases showing depression state or depression state and manic state for a long term. In recent years, it has been found that single intravenous administration of ketamine, an NMDA receptor antagonist, improves depression symptom accompanying major depression and bipolar disorder rapidly and in a sustained manner (Therapeutic Advances in Psychopharmacology, vol. 4, pp. 75-99, 2014). It has also been reported that continuous intravenous administration of CP-101,606, which is antagonist of NMDA receptor containing the NR2B subunit significantly improves treatment resistant-depression symptom (Journal of Clinical Psychopharmacology, vol. 28, pp. 631-637, 2008). Therefore, the compound the present invention is promising as a prophylactic or therapeutic drug for treatment resistant-depression disease.

Migraine is a chronic and paroxysmal primary headache. While the onset mechanism is unknown, it is considered to be developed along with abnormalities of central nervous system process, abnormalities of trigeminal nerve blood vessel system and the like. In pathophysiology study of migraine, particularly of aura, a cortical spreading depression phenomenon is attracting attention. It has been reported that CP-101,606 and Ro25-6981, which are antagonists of NMDA receptor containing the NR2B subunit, suppress the number of occurrence and the depth of cortical spreading depression in an experimental cortical spreading depression test using rodents (the Journal of Pharmacology and Experimental Therapeutics, vol. 321, pp. 564-572, 2007). Therefore, the compound the present invention is promising as a prophylactic or therapeutic drug for migraine.

Pain is classified into acute pain whose pain lasts for a comparatively short period of time, and chronic pain accompanying retention or recurrence for 3 months or longer, retention for not less than one month after recovery of acute tissue injury, or an unhealed lesion. An NMDA receptor containing the NR2B subunit is highly expressed in posterior horn of spinal cord which plays an important role in the acceptance of pain, and functional control thereof is suggested to enable pain control. In fact, a genetic modification that causes functional decline of NR2B subunit has been reported to elevate the pain threshold (European Journal of Neuroscience, vol. 32, pp. 798-810, 2010). Also, it has been reported that the increase in pain threshold by ifenprodil, which is an antagonist of an NMDA receptor containing the NR2B subunit (Pain, vol. 153, pp. 1022-1029, 2012). Therefore, the compound the present invention is promising as a prophylactic or therapeutic drug for pain.

Dementia refers to chronic, general, and generally irreversible decline of cognition. While the degradation of quality of life of patients due to the cognitive decline is remarkable, behavioral and psychological symptoms of dementia (psychological symptom or abnormal behavior) is also considered to be a factor markedly influencing the quality of life of patients and caregiver thereof. An effective therapeutic intervention method for behavioral and psychological symptoms of dementia has not been established; however, it has been reported that administration of memantine, which is an NMDA receptor antagonist, partially improves behavioral and psychological symptoms of dementia (Annals of Pharmacotherapy, vol. 42, pp. 32-38, 2007). While NMDA receptor containing the NR2B subunit is widely distributed in the brain except cerebellum, behavioral and psychological symptoms of dementia has been reported to be related to white matter abnormality of brain region except cerebellum (Journal of the Neurological Sciences, vol. 337, pp. 162-166, 2014). Therefore, the compound the present invention is promising as a prophylactic or therapeutic drug for behavioral and psychological symptoms of dementia.

While the dose of the compound of the present invention varies depending on the subject of administration, administration route, target disease, symptom and the like, for example; when the compound of the present invention is administered orally or parenterally to an adult patient, its dose may be, for example, about 0.01 to 100 mg/kg body weight per dose, preferably 0.1 to 50 mg/kg body weight per dose and more preferably 0.5 to 20 mg/kg body weight per dose. This amount may be desirably administered in one to 3 portions daily.

The compound of the present invention may be used in combination with other active ingredients (hereinafter to be abbreviated as concomitant drug).

Examples of the concomitant drug include the following. Acetylcholine esterase inhibitor (e.g., donepezil, rivastigmine, galanthamine, zanapezil), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, P amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), 1 amyloid vaccine, β amyloid-degrading enzyme and the like, brain function enhancer (e.g., aniracetam, nicergoline), other therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation/regeneration promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-HT$_{1A}$ agonist, (buspirone hydrochloride, tandospirone citrate, osemozotan hydrochloride etc.), 5-HT antagonist, 5-HT$_{2A}$ inverse agonist, 5-HT$_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin Vlb antagonist, vasopressin Vla antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), antiobesity drug, therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent, antibody medicament, nucleic acid or nucleic acid derivative, aptamer drug and the like.

Two or more kinds of the above-mentioned concomitant drugs may be used in combination at an appropriate ratio.

When the compound of the present invention is applied to each of the above-mentioned diseases, it can also be used in combination with biologics (e.g., antibody drug, nucleic acid or derivatives thereof, aptamer drug, vaccine preparation), or can be combined with a gene therapy method and the like and applied as a combination therapy, or can also be used in combination with a treatment in psychiatric field without using drugs.

Examples of the antibody drug and vaccine preparation include vaccine preparation against angiotensin II, vaccine preparation against CETP, CETP antibody, antibody against TNFα antibody and other cytokines, amyloid β vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to an enzyme or protein involved in blood lipid metabolism (e.g., a gene relating to metabolism, excretion and absorption of cholesterol or triglyceride or HDL-cholesterol or blood phospholipid), a treatment method using a gene relating to an enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention may also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

By combining the compound of the present invention and a concomitant drug, a superior effect such as
(1) the dose may be reduced as compared to single administration of the compound of the present invention or a concomitant drug,
(2) the drug to be combined with the compound of the present invention may be selected according to the condition of patients (mild case, severe case and the like),
(3) the period of treatment may be set longer by selecting a concomitant drug having different action and mechanism from the compound of the present invention,
(4) a sustained treatment effect may be designed by selecting a concomitant drug having different action and mechanism from the compound of the present invention,
(5) a synergistic effect may be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of the administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

When the compound of the present invention and a concomitant drug may be separately formulated into preparations, the contents thereof are similar to the above.

The production method of the compound of the present invention is explained below.

The raw material compound and reagent used and the compound obtained in each step in the following production method may be each in a form of a salt, and examples of such salt include those similar to the salts of the compound represented by the formula (I), and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known-per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acid catalyst is used for the reaction in each step, examples thereof include those described in Examples and the following acids and acid catalysts inorganic acids: hydrochloric acid, sulfuric acid, nitric acid, hydrobromic acid, phosphoric acid and the like; organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and a phosphine (e.g., triphenylphosphine, tributhylphosphine etc.) are used as a reagent.

When esterification reaction, amidation reaction or urea formation reaction is carried out in each step, examples of the reagent to be used include acyl halides such as acid chlorides, acid bromides and the like; activated carboxylic acids such as acid anhydrides, activated esters, sulfates and the like. Examples of the activating agent of the carboxylic acid include carbodiimide condensing agents such as N-(3-(dimethylamino)propyl)-N'-ethylcarbodiimide hydrochloride (WSC HCl) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced from compound (1) according to the following Production Step A.

[Production Step A]

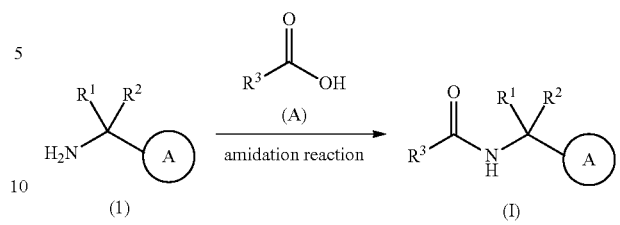

wherein each symbol is as defined above.

Compound (I) can be produced by subjecting compound (1) to an amidation reaction with compound (A).

Compound (1) can be produced, for example, according to the following Production Step B to H or a method analogous thereto. Compound (A) can be produced by a method known per se.

Among compound (1), compound (1-i) can be produced from compound (2) according to the following Production Step B.

[Production Step B]

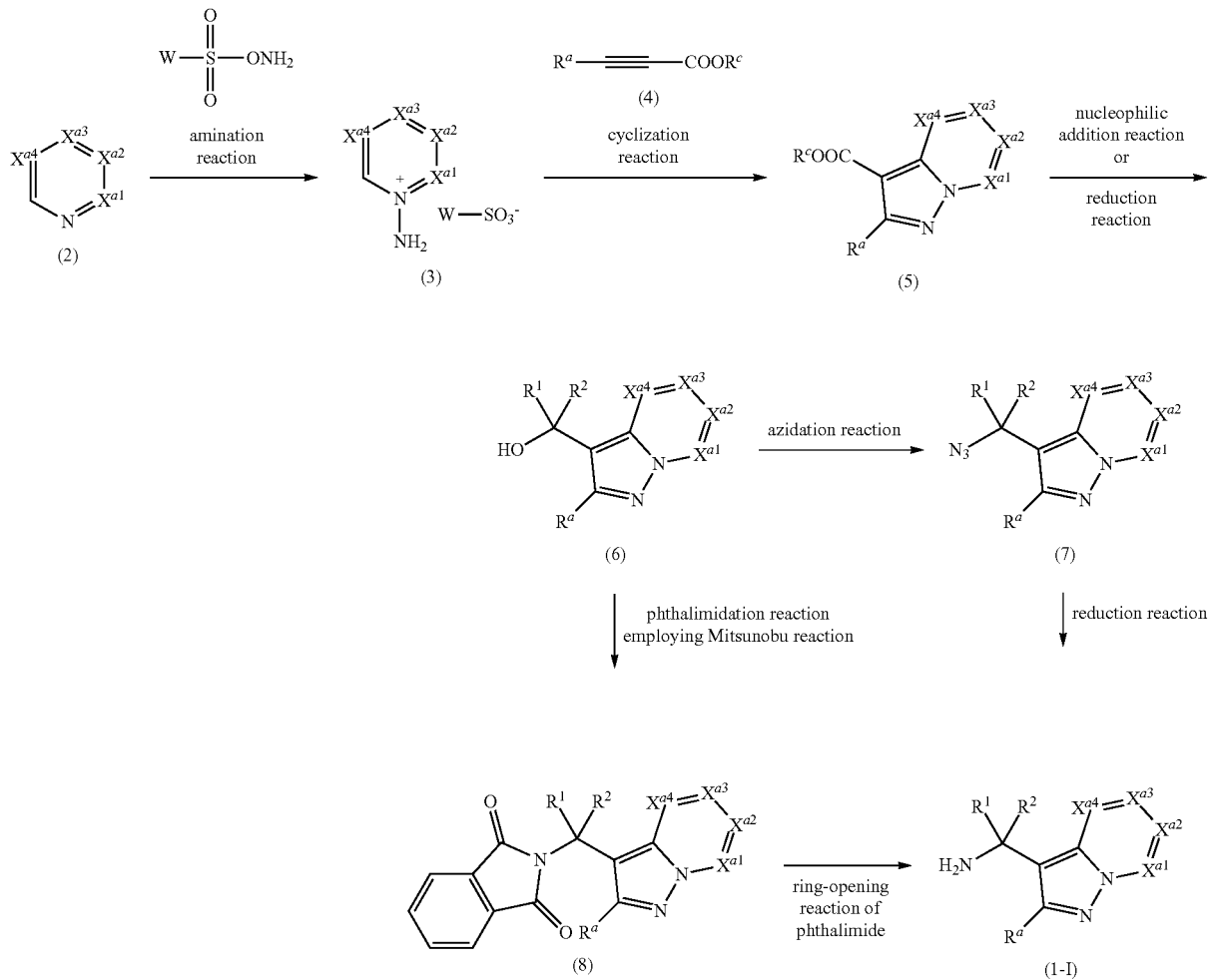

wherein $R^c$ is a $C_{1-6}$ alkyl group, W is a hydroxy group or a 2,4,6-trimethylphenyl group, and the other symbols are as defined above.

Compound (3) can be produced by subjecting compound (2) to an amination reaction. Examples of the reagent to be used include 0-(2,4,6-trimethylbenzenesulfonyl)hydroxylamine, hydroxylamine-O-sulfonic acid and the like. Compound (5) can be produced by subjecting compound (3) to a cyclization reaction with compound (4). Examples of the reagent to be used include potassium carbonate and the like. Compound (6) can be produced by subjecting compound (5) to a nucleophilic addition reaction or a reduction reaction (in the case that $R^1$ and $R^2$ are both hydrogen atoms). Alternatively, compound (6) can also be produced by converting the ester moiety of compound (5) to the corresponding anhydride (containing a mixed anhydride) or an acid halide, and subjecting the resulting compound to a nucleophilic addition reaction or a reduction reaction (in the case that $R^1$ and $R^2$ are both hydrogen atoms). Compound (7) can be produced by subjecting compound (6) to an azidation reaction. Compound (1-i) can be produced by subjecting compound (7) to a reduction reaction. Examples of the reagent to be used include triphenylphosphine and the like. Compound (8) can be produced by subjecting compound (6) to a phthalimidation reaction employing Mitsunobu reaction. Compound (1-i) can also be produced by subjecting compound (8) to a ring-opening reaction of the phthalimide. Examples of the reagent to be used include hydrazine monohydrate and the like.

Among compound (1), compound (1-ii) can be produced from compound (9) according to the following Production Step C.

[Production Step C]

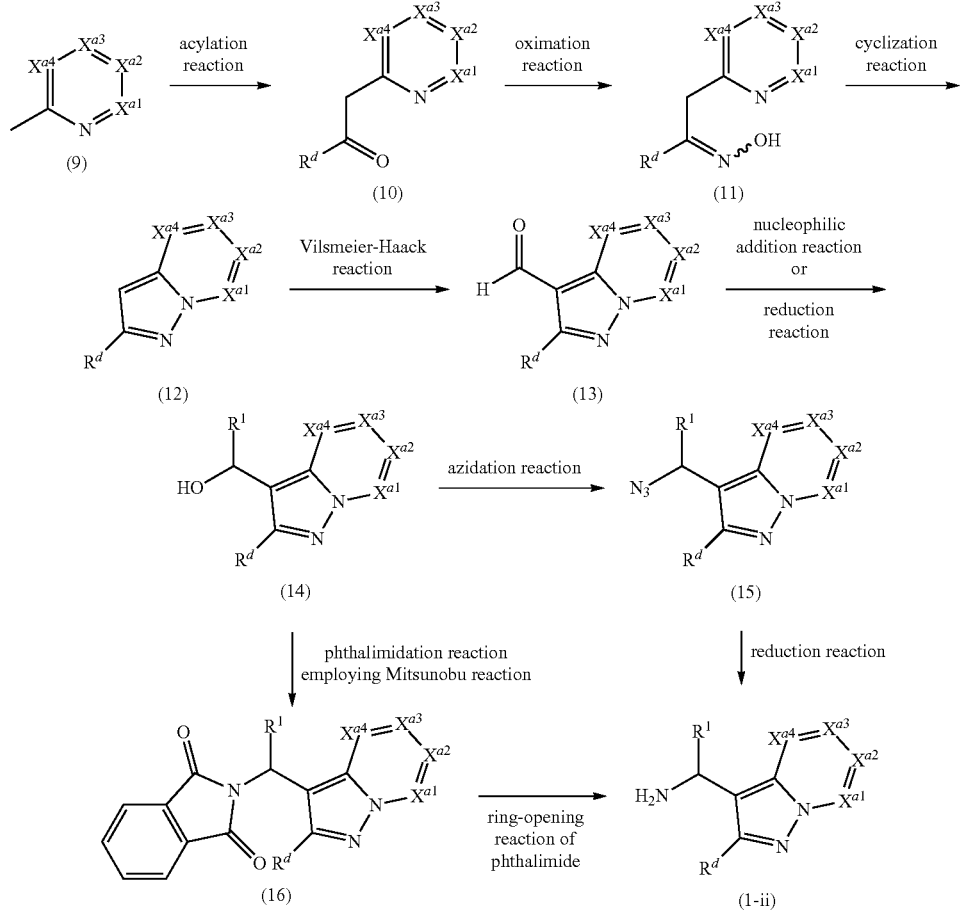

wherein $R^d$ is an optionally substituted $C_{1-6}$ alkyl group, and the other symbols are as defined above.

Compound (10) can be produced by subjecting compound (9) to an acylation reaction. Examples of the acylating reagent to be used include ethyl acetate and the like, and examples of the base to be used include lithium hexamethyldisilazide and the like. Compound (11) can be produced by subjecting compound (10) to an oximation reaction. Examples of the reagent to be used include hydroxylamine hydrochloride and the like. Compound (12) can be produced by subjecting compound (11) to a cyclization reaction. Examples of the reagent to be used include a combination of trifluoroacetic anhydride and iron chloride, and the like. Compound (13) can be produced by subjecting compound (12) to Vilsmeier-Haack reaction. Compound (14) can be produced by subjecting compound (13) to a nucleophilic addition reaction or a reduction reaction (in the case that $R^1$ is a hydrogen atom). Compound (15) can be produced by subjecting compound (14) to an azidation reaction. Compound (1-ii) can be produced by subjecting compound (15)

to a reduction reaction. Compound (16) can be produced by subjecting compound (14) to a phthalimidation reaction employing Mitsunobu reaction. Compound (1-ii) can also be produced by subjecting compound (16) to a ring-opening reaction of the phthalimide.

Among compound (1), compound (1-iii) can be produced from compound (17) according to the following Production Step D.

[Production Step D]

reaction. Compound (24) can be produced by subjecting compound (21) to a reductive amination reaction with compound (22), followed by an introduction reaction of a protecting group ($PG^2$). Compound (1-iii) can also be produced by subjecting compound (24) to an oxidation reaction, followed by a deprotection reaction. Examples of the oxidizing agent to be used in the oxidation reaction include manganese dioxide and the like.

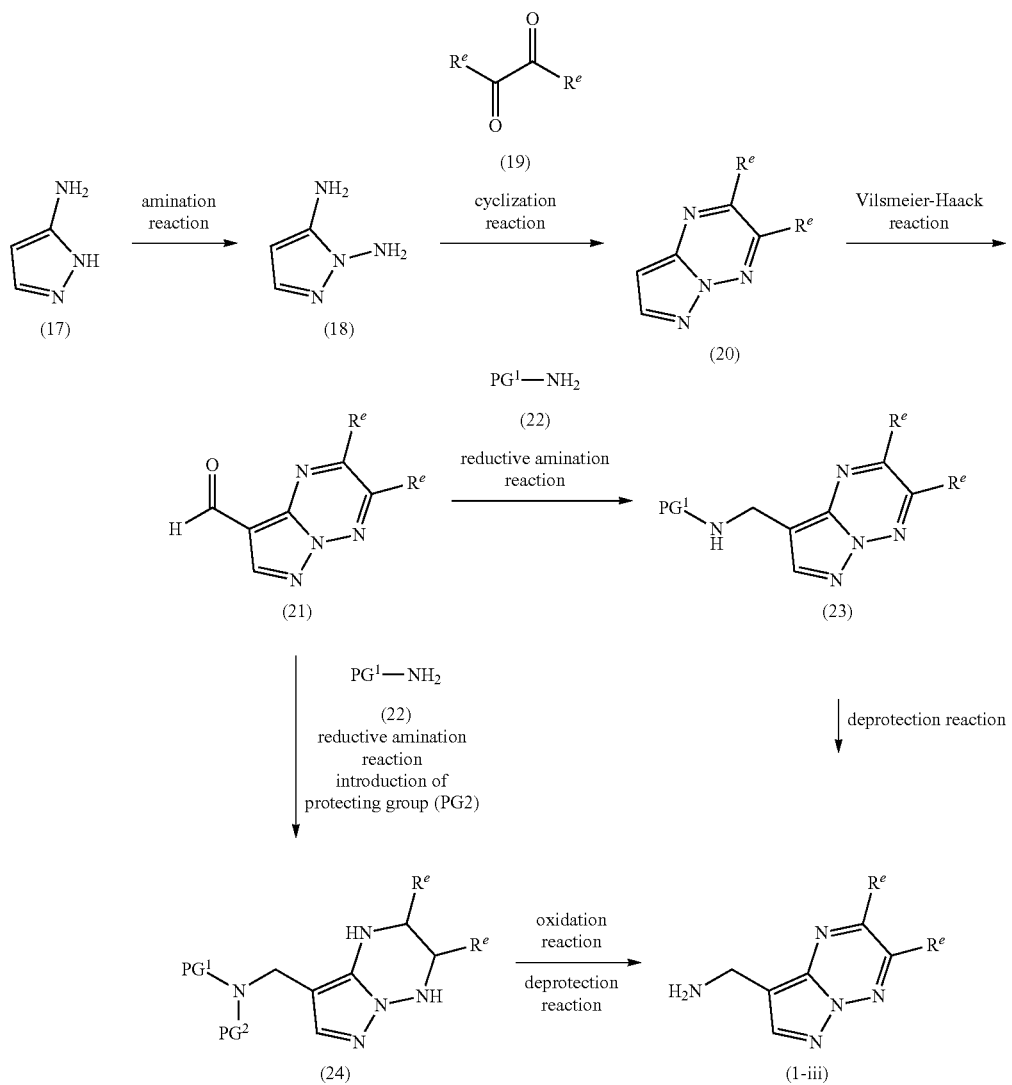

wherein $R^e$ is a hydrogen atom or an optionally substituted $C_{1-6}$ alkyl group, and $PG^1$ and $PG^2$ are each an amino-protecting group.

Compound (18) can be produced by subjecting compound (17) to an amination reaction. Examples of the reagent to be used include hydroxylamine-O-sulfonic acid and the like. Compound (20) can be produced by subjecting compound (18) to a cyclization reaction with compound (19). Compound (21) can be produced by subjecting compound (20) to Vilsmeier-Haack reaction. Compound (23) can be produced by subjecting compound (21) to a reductive amination reaction with compound (22). Compound (1-iii) can be produced by subjecting compound (23) to a deprotection reaction.

Among compound (1), compound (1-iv) can be produced from compound (25) according to the following Production Step E.

[Production Step E]

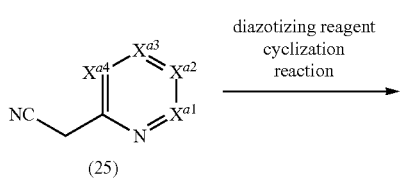

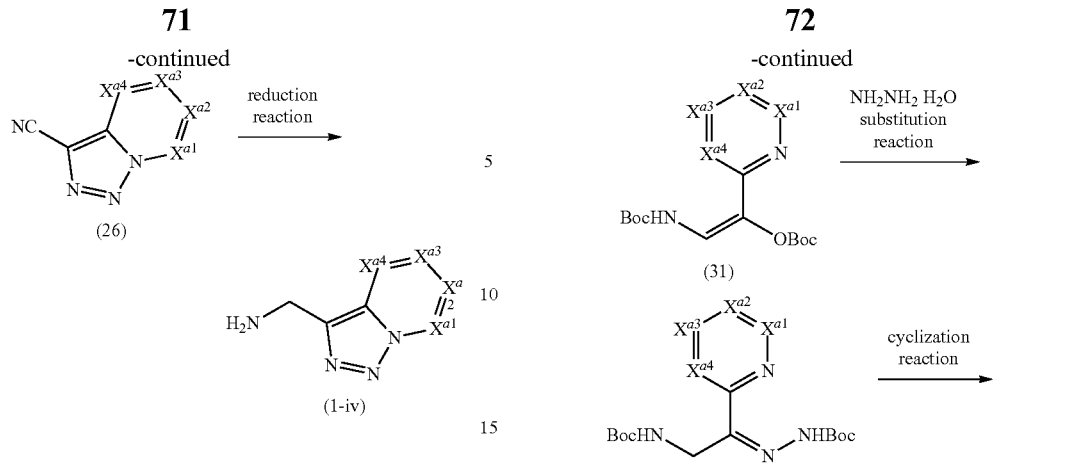

wherein each symbol is as defined above.

Compound (26) can be produced by subjecting compound (25) to a cyclization reaction using a diazotizing reagent. Examples of the diazotizing reagent to be used include 4-acetamidobenzenesulfonyl azide and the like. Compound (1-iv) can be produced by subjecting compound (26) to a reduction reaction. Examples of the reagent to be used include a combination of cobalt chloride and sodium borohydride, and the like.

Alternatively, compound (1-iv) can also be produced from compound (27) according to the following Production Step F.

[Production Step F]

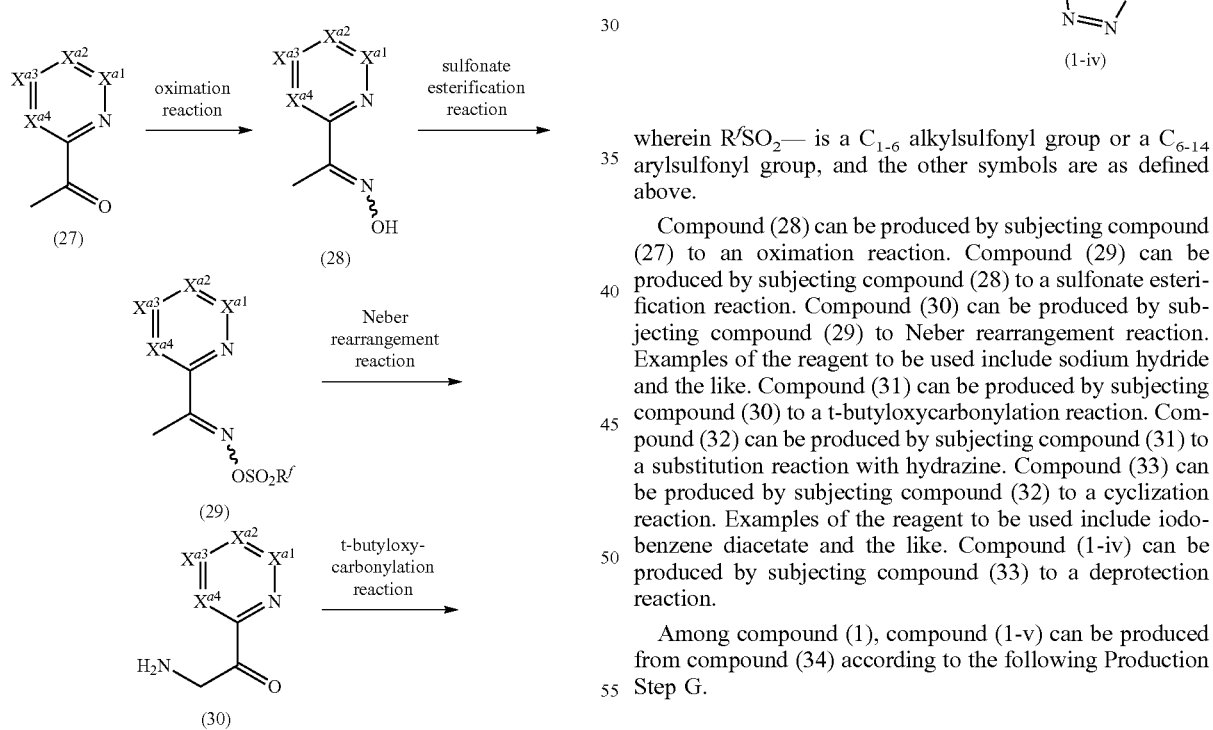

wherein $R^fSO_2$— is a $C_{1-6}$ alkylsulfonyl group or a $C_{6-14}$ arylsulfonyl group, and the other symbols are as defined above.

Compound (28) can be produced by subjecting compound (27) to an oximation reaction. Compound (29) can be produced by subjecting compound (28) to a sulfonate esterification reaction. Compound (30) can be produced by subjecting compound (29) to Neber rearrangement reaction. Examples of the reagent to be used include sodium hydride and the like. Compound (31) can be produced by subjecting compound (30) to a t-butyloxycarbonylation reaction. Compound (32) can be produced by subjecting compound (31) to a substitution reaction with hydrazine. Compound (33) can be produced by subjecting compound (32) to a cyclization reaction. Examples of the reagent to be used include iodobenzene diacetate and the like. Compound (1-iv) can be produced by subjecting compound (33) to a deprotection reaction.

Among compound (1), compound (1-v) can be produced from compound (34) according to the following Production Step G.

[Production Step G]

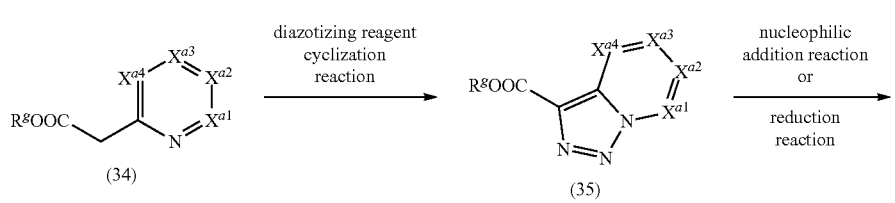

-continued

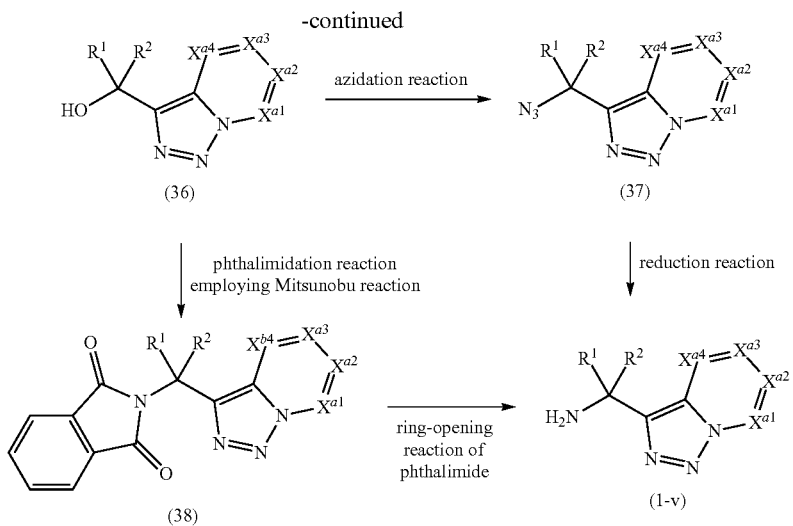

wherein $R^g$ is a $C_{1-6}$ alkyl group, and the other symbols are as defined above.

Compound (35) can be produced by subjecting compound (34) to a cyclization reaction using a diazotizing reagent. Compound (36) can be produced by subjecting compound (35) to a nucleophilic addition reaction or a reduction reaction (in the case that $R^1$ and $R^2$ are both hydrogen atoms). Compound (37) can be produced by subjecting compound (36) to an azidation reaction. Compound (1-v) can be produced by subjecting compound (37) to a reduction reaction. Compound (38) can be produced by subjecting compound (36) to a phthalimidation reaction employing Mitsunobu reaction. Compound (1-v) can also be produced by subjecting compound (38) to a ring-opening reaction of the phthalimide.

Compound (1-v) wherein $R^1$ and $R^2$ are both hydrogen atoms is the same as compound (1-iv).

Among compound (1), compound (1-vi) can be produced from compound (39) according to the following Production Step H.

[Production Step H]

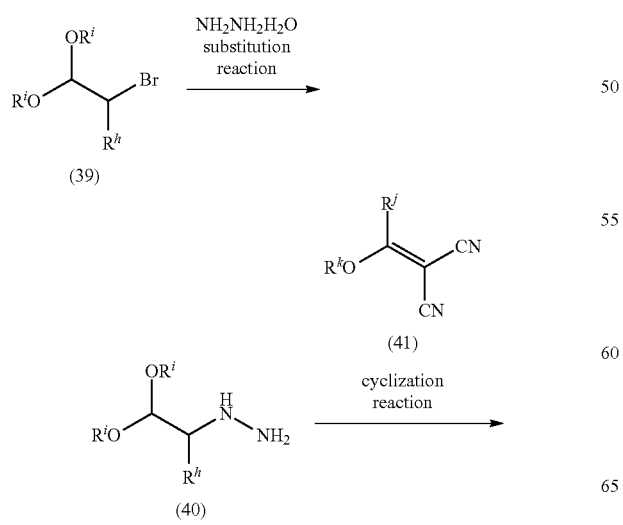

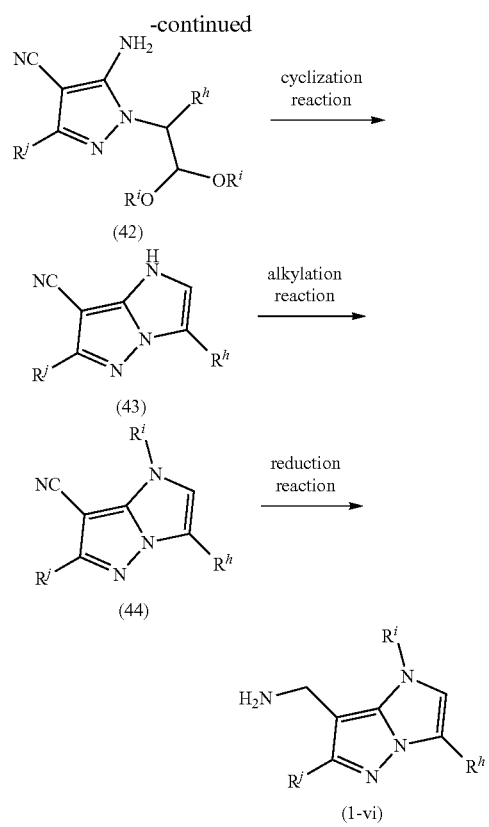

wherein $R^h$ and $R^j$ are each a hydrogen atom or an optionally substituted $C_{1-6}$ alkyl group, and $R^i$, $R^k$ and $R^l$ are each an optionally substituted $C_{1-6}$ alkyl group.

Compound (40) can be produced by subjecting compound (39) to substitution reaction with hydrazine. Compound (42) can be produced by subjecting compound (40) to a cyclization reaction to with compound (41). Compound (43) can be produced by subjecting compound (42) to a cyclization reaction. Examples of the reagent to be used include sulfuric acid and the like. Compound (44) can be produced by subjecting compound (43) to an alkylation reaction. Compound (1-vi) can be produced by subjecting compound (44)

to a reduction reaction. Examples of the reagent to be used include Raney nickel and the like.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production method can be isolated and purified by a known means, such as solvent extraction, pH conversion of liquid, phase transfer, crystallization, recrystallization and chromatography.

When compound (I) contains optical isomer, stereoisomer, regio isomer and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) may be a crystal.

A crystal of compound (I) (hereinafter sometimes to be abbreviated as the crystal of the present invention) can be produced by crystallizing compound (I), by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy expression), and is extremely useful as a medicament.

EXAMPLES

The present invention is explained in detail in the following by referring to Examples, Experimental Examples and Formulation Examples. However, the examples do not limit the present invention and the examples can be modified within the scope of the present invention.

The "room temperature" in the following Examples is generally about 10° C. to about 35° C. The ratio for mixed solvent is a volume mixing ratio unless otherwise specified, and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

Elemental analysis value (Anal.) is described as calculated value (Calcd) and actual measured value (Found).

Powder X-ray diffraction patterns were generated using a Rigaku Ultima IV (Rigaku, Tokyo, Japan) with Copper K-alpha radiation.

In the following Examples, the following abbreviations are used.

mp: melting point
MS: mass spectrum
M: mol concentration
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
HATU: O-(7-azabenzotriazol-1-yl)-N,N,N',N'-tetramethyluronium hexafluorophosphorate
DPPA: diphenylphosphoryl azide
TFA: trifluoroacetic acid
DIPEA: N-ethyl-N-isopropylpropan-2-amine
DMA: N,N-dimethylacetamide
DMF: N,N-dimethylformamide
HOBt: 1H-benzotriazol-1-ol
HOBt H$_2$O: 1H-benzotriazol-1-ol hydrate
THF: tetrahydrofuran
WSC HCl: N-(3-(dimethylamino)propyl)-N'-ethylcarbodiimide hydrochloride
Boc$_2$O: di-tert-butyl dicarbonate
DBU: 2,3,4,6,7,8,9,10-octahydropyrimido[1,2-a]azepine
TEA: triethylamine

Example 1

N-((6-fluoro[1,2,3]triazolo[1,5-a]pyridin-3-yl)methyl)-4-(trifluoromethoxy)benzamide A) 6-fluoro[1,2,3]triazolo[1,5-a]pyridine-3-carbonitrile To a mixture of 2-(5-fluoropyridin-2-yl)acetonitrile (681 mg), 4-acetamidobenzenesulfonyl azide (1441 mg) and acetonitrile (15 ml) was added DBU (0.897 ml) at 0° C. The mixture was stirred at room temperature for 3 hr. To the reaction solution was added ethyl acetate, and the mixture was washed with water. The aqueous layer was separated, and extracted with ethyl acetate. The combined organic layers were washed with saturated brine, dried over anhydrous magnesium sulfate, and concentrated under reduced pressure. The residue was purified by silica gel column chromatography (ethyl acetate/hexane) to give the title compound (683 mg).

$^1$H NMR (300 MHz, DMSO-d$_6$) δ 7.97 (1H, ddd, J=9.8, 7.9, 2.1 Hz), 8.35 (1H, ddd, J=9.7, 5.0, 0.8 Hz), 9.80 (1H, ddd, J=3.8, 2.1, 0.8 Hz).

B) N-((6-fluoro[1,2,3]triazolo[1,5-a]pyridin-3-yl)methyl)-4-(trifluoromethoxy)benzamide To a mixture of 6-fluoro[1,2,3]triazolo[1,5-a]pyridine-3-carbonitrile (200 mg), cobalt(II) chloride (240 mg) and methanol (5 ml) was added sodium borohydride (233 mg) by small portions at 0° C. The mixture was stirred overnight at room temperature. To the reaction solution was added 1 M hydrochloric acid at 0° C., and the mixture was concentrated under reduced pressure. The obtained residue was dissolved in DMA (5 ml), and to the reaction solution was added 4-(trifluoromethoxy)benzoyl chloride (0.292 ml) at 0° C. The mixture was stirred at room temperature for 1 hr, the reaction solution was poured into water, and the mixture was filtered. The filtrate was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (23 mg).

$^1$H NMR (300 MHz, DMSO-d$_6$) δ 4.85 (2H, d, J=5.7 Hz), 7.41-7.48 (2H, m), 7.53 (1H, ddd, J=9.8, 8.0, 1.9 Hz), 7.96-8.04 (2H, m), 8.08-8.16 (1H, m), 9.31 (1H, t, J=5.7 Hz), 9.35-9.40 (1H, m).

Example 2

N-((4-methyl[1,2,3]triazolo[1,5-a]pyridin-3-yl)methyl)-4-(trifluoromethoxy)benzamide A) ethyl 4-methyl[1,2,3]triazolo[1,5-a]pyridine-3-carboxylate To a mixture of ethyl (3-methylpyridin-2-yl)acetate (1.00 g), DBU (0.925 ml) and acetonitrile (20 ml) was added 4-acetamidobenzenesulfonyl azide (1.341 g) by small portions at 0° C. The mixture was stirred overnight at room temperature, the reaction solution was poured into water, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (800 mg).

MS: [M+H]$^+$ 206.2.

B) (4-methyl[1,2,3]triazolo[1,5-a]pyridin-3-yl)methanol

To a mixture of lithium aluminium hydride (185 mg) and THF (10 ml) was added a solution of ethyl 4-methyl[1,2,3]triazolo[1,5-a]pyridine-3-carboxylate (500 mg) in THF (10 ml) at 0° C. The mixture was stirred at room temperature for 1 hr, and to the reaction solution was added sodium sulfate decahydrate. The insoluble substance was removed by filtration, and the filtrate was concentrated under reduced pressure to give the title compound (398 mg).

MS: [M+H]$^+$ 164.1.

C) 2-((4-methyl[1,2,3]triazolo[1,5-a]pyridin-3-yl)methyl)-1H-isoindole-1,3(2H)-dione To a mixture of (4-methyl[1,2,3]triazolo[1,5-a]pyridin-3-yl)methanol (390 mg), tributylphosphine (580 mg), 1H-isoindole-1,3(2H)-dione (387 mg) and THF (10 ml) was added bis(2-methoxyethyl) azodicarboxylate (1120 mg) at 0° C. The mixture was stirred at room temperature for 2 hr, and the reaction solution was concentrated. The obtained solid was washed with ethyl acetate to give the title compound (406 mg).

MS: [M+H]$^+$ 293.1.

D) 1-(4-methyl[1,2,3]triazolo[1,5-a]pyridin-3-yl)methanamine

To a mixture of 2-((4-methyl[1,2,3]triazolo[1,5-a]pyridin-3-yl)methyl)-1H-isoindole-1,3 (2H)-dione (400 mg) and ethanol (2 ml) was added hydrazine monohydrate (2 ml) at room temperature. The mixture was refluxed for 1 hr, and the reaction solution was concentrated. The residue was purified by silica gel column chromatography (NH, methanol/ethyl acetate) to give the title compound (270 mg).

$^1$H NMR (300 MHz, DMSO-d$_6$) δ 2.68 (3H, s), 4.13 (2H, s), 6.97-7.05 (1H, m), 7.05-7.11 (1H, m), 8.80 (1H, dd, J=6.8, 0.8 Hz), 8.93 (2H, brs).

E) N-((4-methyl[1,2,3]triazolo[1,5-a]pyridin-3-yl)methyl)-4-(trifluoromethoxy)benzamide To a mixture of 1-(4-methyl[1,2,3]triazolo[1,5-a]pyridin-3-yl)methanamine (100 mg) and DMA (5 ml) was added 4-(trifluoromethoxy)benzoyl chloride (0.486 ml) at 0° C. The mixture was stirred at room temperature for 3 hr. To the mixture was added 1 M aqueous sodium hydroxide solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (84.3 mg).

$^1$H NMR (300 MHz, DMSO-d$_6$) δ 2.66 (3H, s), 4.94 (2H, d, J=4.9 Hz), 7.02-7.10 (1H, m), 7.11-7.18 (1H, m), 7.44 (2H, dd, J=8.9, 0.9 Hz), 7.96-8.05 (2H, m), 8.84-8.92 (1H, m), 9.10 (1H, t, J=4.9 Hz).

Example 6

6-(difluoromethoxy)-5-fluoro-N-(pyrazolo[1,5-b]pyridazin-3-ylmethyl)nicotinamide (this Compound is Also Named as 6-(difluoromethoxy)-5-fluoro-N-[(pyrazolo[1,5-b]pyridazin-3-yl)methyl]pyridine-3-carboxamide)

A) methyl pyrazolo[1,5-b]pyridazine-3-carboxylate

To a mixture of pyridazine (3.0 g) and dichloromethane (30 ml) was added a solution of O-(2,4,6-trimethylbenzenesulfonyl)hydroxylamine (8.06 g) in dichloromethane (30 ml) at 0° C. The mixture was stirred at 0° C. for 1 hr, and the reaction solution was concentrated. The obtained residue was dissolved in DMF (20 ml), and to the solution were added methyl propiolate (4.72 g) and potassium carbonate (15.5 g) at 20° C. The mixture was stirred at 20° C. for 12 hr, diluted with water, and extracted with ethyl acetate. The combined organic layers were washed with saturated brine, dried over anhydrous sodium sulfate, and concentrated under reduced pressure. The residue was purified by silica gel column chromatography (ethyl acetate/petroleum ether) to give the title compound (3.35 g).

MS: [M+H]$^+$ 178.

B) pyrazolo[1,5-b]pyridazin-3-ylmethanol

To a mixture of methyl pyrazolo[1,5-b]pyridazine-3-carboxylate (4.80 g) and dichloromethane (300 ml) was added dropwise diisobutylaluminium hydride (1 M toluene solution, 96.6 ml) under nitrogen atmosphere at −78° C. The mixture was stirred at −78° C. for 2 hr. To the reaction solution was added methanol (50 ml) at −78° C., and the resulting insoluble substance was removed by filtration, and washed with dichloromethane and methanol. The filtrate was washed with saturated brine, dried over anhydrous sodium sulfate, and concentrated under reduced pressure.

The residue was purified by silica gel column chromatography (ethyl acetate/petroleum ether) to give the title compound (1.75 g).
MS: [M+H]$^+$ 150.1.

C) 3-(azidomethyl)pyrazolo[1,5-b]pyridazine

A mixture of pyrazolo[1,5-b]pyridazin-3-ylmethanol (5.30 g), DPPA (11.7 g), DBU (7.03 g) and toluene (150 ml) was stirred under nitrogen atmosphere at 25° C. for 12 hr. The mixture was diluted with 1 M hydrochloric acid, and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (2.88 g).
MS: [M+H]$^+$ 175.1.

D) 1-(pyrazolo[1,5-b]pyridazin-3-yl)methanamine hydrochloride

A mixture of 3-(azidomethyl)pyrazolo[1,5-b]pyridazine (4.40 g), triphenylphosphine (13.3 g), THF (40 ml) and 25% aqueous ammonia (10 ml) was stirred at 70° C. for 3 hr. The reaction solution was concentrated, to the obtained residue was added 4 M hydrogen chloride/1,4-dioxane (80 ml), and the mixture was stirred at 25° C. for 1 hr. The reaction solution was concentrated under reduced pressure, and to the obtained residue was added ethyl acetate. The resulting precipitate was collected by filtration to give the title compound (4.63 g).
MS: [M+H]$^+$ 149.1.

E) 6-(difluoromethoxy)-5-fluoro-N-(pyrazolo[1,5-b]pyridazin-3-ylmethyl)nicotinamide To a mixture of 6-(difluoromethoxy)-5-fluoronicotinic acid (1.346 g) and DMF (40 ml) were added 1-(pyrazolo[1,5-b]pyridazin-3-yl)methanamine hydrochloride (1.00 g), TEA (2.265 ml), WSC HCl (1.246 g) and HOBt H$_2$O (1.244 g) at room temperature. The mixture was stirred overnight at room temperature. The reaction solution was diluted with water, and the mixture was extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane). The obtained solid was crystallized from ethyl acetate/hexane to give the title compound (1.22 g).
$^1$H NMR (300 MHz, DMSO-d$_6$) δ 4.65 (2H, d, J=5.3 Hz), 7.21 (1H, dd, J=9.0, 4.1 Hz), 7.52-8.03 (1H, m), 8.08 (1H, s), 8.28 (1H, dd, J=10.9, 1.9 Hz), 8.37 (1H, dd, J=9.0, 1.5 Hz), 8.42 (1H, dd, J=4.5, 1.9 Hz), 8.54 (1H, d, J=1.9 Hz), 9.21 (1H, t, J=5.1 Hz).
The obtained crystal was characterized by having specific peaks at the two theta (diffraction angle) of 7.8°±0.2°, 14.2°±0.2°, 14.6°±0.2°, 15.0°±0.2°, 15.6°±0.2°, 18.0°±0.2°, 19.4°±0.2°, 21.8°±0.2°, 22.4°±0.2°, 23.6°±0.2°, 26.8°±0.20, 28.3° 0.2 and 29.3°±0.2° degrees in a powder X-ray diffraction pattern.

Example 8

5-chloro-6-(difluoromethoxy)-N-(pyrazolo[1,5-b]pyridazin-3-ylmethyl)nicotinamide To a mixture of 5-chloro-6-(difluoromethoxy)nicotinic acid (1635 mg) and DMF (30 ml) were added 1-(pyrazolo[1,5-b]pyridazin-3-yl)methanamine hydrochloride (900 mg), TEA (2.038 ml), WSC HCl (1121 mg) and HOBt H$_2$O (896 mg) at room temperature. The mixture was stirred overnight at room temperature. The mixture was diluted with water, and extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane). The obtained solid was crystallized from ethyl acetate/hexane to give the title compound (1.21 g).
$^1$H NMR (300 MHz, DMSO-d$_6$) δ 4.65 (2H, d, J=5.7 Hz), 7.21 (1H, dd, J=9.0, 4.5 Hz), 7.53-8.05 (1H, m), 8.08 (1H, s), 8.33-8.45 (2H, m), 8.48 (1H, d, J=2.3 Hz), 8.65 (1H, d, J=1.9 Hz), 9.20 (1H, t, J=5.3 Hz).

Example 13

3-fluoro-N-([1,2,3]triazolo[1,5-a]pyridin-3-ylmethyl)-4-(trifluoromethoxy)benzamide (this Compound is Also Named as 3-fluoro-N-[([1,2,3]triazolo[1,5-a]pyridin-3-yl)methyl]-4-(trifluoromethoxy)benzamide)

A) 3-(azidomethyl) [1,2,3]triazolo[1,5-a]pyridine

To a mixture of methyl pyridin-2-ylacetate (5.43 g), 4-acetamidobenzenesulfonyl azide (10.36 g) and acetonitrile (100 ml) was added DBU (6.50 ml) at 0° C. The mixture was stirred overnight at room temperature. The reaction solution was poured into water, and the mixture was extracted with ethyl acetate. The organic layer was separated, washed with saturated aqueous ammonium chloride solution and saturated brine, dried over anhydrous magnesium sulfate, and concentrated under reduced pressure. The obtained residue was washed with ethyl acetate and hexane to give a crude product (7.70 g). To a mixture of lithium aluminium hydride (0.418 g) and THF (30 ml) was added a solution of a part (1.5 g) of the crude product in THF (30 ml) at 0° C. The mixture was stirred at 0° C. for 20 min, to the reaction solution was added sodium sulfate decahydrate, and the insoluble substance was removed by filtration. The filtrate was concentrated under reduced pressure to give a residue (879 mg). To a mixture of the obtained residue (878 mg) and THF (24 ml) were added DBU (1.863 ml) and DPPA (2.66 ml) at 0° C. The mixture was stirred overnight under nitrogen atmosphere at room temperature. To the mixture was added water at room temperature, and the mixture was extracted with ethyl acetate. The combined organic layers were washed with saturated brine, dried over anhydrous magnesium sulfate, and concentrated under reduced pressure. The residue was purified by silica gel column chromatography (ethyl acetate/hexane) to give the title compound (865.6 mg).
$^1$H NMR (300 MHz, DMSO-d$_6$) δ 4.90 (2H, s), 7.22 (1H, td, J=6.9, 0.9 Hz), 7.48 (1H, dd, J=8.7, 6.8 Hz), 8.10 (1H, d, J=8.7 Hz), 9.09 (1H, d, J=7.2 Hz).

B) 1-([1,2,3]triazolo[1,5-a]pyridin-3-yl)methanamine

A mixture of 3-(azidomethyl)[1,2,3]triazolo[1,5-a]pyridine (1.41 g), THF (18 ml), water (3.60 ml) and triphenylphosphine (2.55 g) was stirred overnight at room temperature, and the reaction solution was concentrated under reduced pressure. The obtained residue was purified by silica gel column chromatography (NH, methanol/ethyl acetate) to give the title compound (1.178 g).

$^1$H NMR (300 MHz, DMSO-d$_6$) δ 1.88 (2H, brs), 4.09 (2H, s), 7.11 (1H, td, J=6.9, 0.9 Hz), 7.32 (1H, dd, J=8.9, 6.6 Hz), 8.05 (1H, d, J=9.0 Hz), 8.97 (1H, d, J=7.2 Hz).

C) 3-fluoro-N-([1,2,3]triazolo[1,5-a]pyridin-3-ylmethyl)-4-(trifluoromethoxy)benzamide A mixture of 1-([1,2,3]triazolo[1,5-a]pyridin-3-yl)methanamine (1.20 g), DMA (35 ml), 3-fluoro-4-(trifluoromethoxy)benzoic acid (2.178 g), WSC HCl (1.863 g), HOBt (1.313 g) and TEA (4.52 ml) was stirred overnight at room temperature. To the mixture were added saturated aqueous sodium hydrogencarbonate solution and water, and the resulting precipitate was collected by filtration. The obtained solid was purified by silica gel column chromatography (ethyl acetate/hexane). The obtained solid was crystallized from ethyl acetate/hexane to give the title compound (2.18 g).

$^1$H NMR (300 MHz, DMSO-ds) δ 4.87 (2H, d, J=5.3 Hz), 7.17 (1H, td, J=6.8, 1.1 Hz), 7.40 (1H, dd, J=8.9, 6.6 Hz), 7.63-7.74 (1H, m), 7.84 (1H, d, J=8.7 Hz), 7.97 (1H, dd, J=11.3, 1.9 Hz), 8.03 (1H, d, J=9.0 Hz), 9.03 (1H, d, J=6.8 Hz), 9.38 (1H, t, J=5.3 Hz).

The obtained crystal was characterized by having specific peaks at the two theta of 13.9°±0.2°, 14.8°±0.2°, 15.1°±0.2°, 15.9°±0.2°, 17.6°±0.2°, 19.1°±0.2° and 23.6°±0.2° degrees in a powder X-ray diffraction pattern.

Example 16

3-fluoro-N-(pyrazolo[1,5-a]pyrazin-3-ylmethyl)-4-(trifluoromethoxy)benzamide

A) ethyl pyrazolo[1,5-a]pyrazine-3-carboxylate

To a mixture of hydroxylamine-O-sulfonic acid (33.9 g) and water (100 ml) was added sodium carbonate (17.20 g) at 0° C. until the mixture reached pH 6. To the reaction solution was added pyrazine (20.0 g) at 0° C., and the mixture was stirred at 50° C. for 30 min. The reaction solution was concentrated under reduced pressure, and subjected to azeotrope with toluene to give a residue. A mixture of the obtained residue (53.7 g), DMF (499 ml), ethyl propiolate (37.9 ml) and potassium carbonate (69.0 g) was stirred at room temperature for 16 hr. The mixture was diluted with ethyl acetate (200 ml), and the resulting precipitate was removed by filtration. The filtrate was concentrated, and the residue was partitioned between ethyl acetate-water, and the organic layer was washed with water and saturated brine, dried over anhydrous magnesium sulfate, and filtered through NH silica gel. The obtained filtrate was concentrated under reduced pressure, and the residue was purified by silica gel column chromatography (ethyl acetate/hexane) and silica gel column chromatography (NH, ethyl acetate/hexane) to give the title compound (1.91 g).

MS: [M+H]$^+$ 191.9.

B) pyrazolo[1,5-a]pyrazine-3-carboxylic acid

To a mixture of ethyl pyrazolo[1,5-a]pyrazine-3-carboxylate (1.30 g), THF (7.56 ml) and ethanol (3.78 ml) was added 1 M aqueous sodium hydroxide solution (8.16 ml) at room temperature. The mixture was stirred at room temperature for 16 hr, and to the reaction solution was added 1 M hydrochloric acid (8.2 ml) at 0° C. until the mixture reached pH 6. The resulting precipitate was collected by filtration, and the obtained solid was washed with water to give the title compound (1.06 g).

MS: [M+H]$^+$ 164.0.

C) 3-(azidomethyl)pyrazolo[1,5-a]pyrazine

To a mixture of pyrazolo[1,5-a]pyrazine-3-carboxylic acid (2.11 g) and THF (400 ml) were added 4-methylmorpholine (1.706 ml) and isobutyl chloroformate (2.013 ml) at 0° C. The mixture was stirred at room temperature for 30 min, the insoluble substance was removed by filtration, and the filtrate was added dropwise to a mixture of sodium borohydride (0.734 g) and ethanol (80 ml) at 0° C. The mixture was stirred at 0° C. for 1.5 hr, to the reaction solution was added 6 M hydrochloric acid, and the mixture was concentrated under reduced pressure. To a mixture of the obtained residue and THF (120 ml) were added DPPA (5.56 ml) and DBU (5.85 ml) at room temperature. The mixture was stirred at room temperature for 16 hr, and partitioned between ethyl acetate-water, and the organic layer was washed with water and saturated brine, dried over anhydrous magnesium sulfate, and concentrated under reduced pressure. The residue was purified by silica gel column chromatography (ethyl acetate/hexane) to give the title compound (954 mg).

MS: [M+H]$^+$ 175.0.

D) 1-(pyrazolo[1,5-a]pyrazin-3-yl)methanamine hydrochloride

To a mixture of 3-(azidomethyl)pyrazolo[1,5-a]pyrazine (945 mg), THF (10 ml) and water (2.0 ml) was added triphenylphosphine (1708 mg) at room temperature. The mixture was stirred at room temperature for three days. The reaction solution was concentrated, the residue was dissolved in ethyl acetate (20 ml), and to the solution was added 4 M hydrogen chloride/ethyl acetate (4.07 ml). The resulting solid was collected by filtration to give the title compound (629 mg).

MS: [M+H]$^+$ 149.0.

E) 3-fluoro-N-(pyrazolo[1,5-a]pyrazin-3-ylmethyl)-4-(trifluoromethoxy)benzamide To a mixture of 1-(pyrazolo[1,5-a]pyrazin-3-yl)methanamine hydrochloride (1.00 g) and DMF (30 ml) were added 3-fluoro-4-(trifluoromethoxy)benzoic acid (1.214 g), WSC HCl (1.557 g), HOBt (0.878 g) and TEA (2.265 ml) at room temperature. The mixture was stirred overnight at room temperature. The reaction solution was poured into water, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane). The obtained solid was crystallized from ethyl acetate/heptane to give the title compound (503 mg).

$^1$H NMR (300 MHz, DMSO-d$_6$) δ 4.73 (2H, d, J=5.7 Hz), 7.64-7.75 (1H, m), 7.79-7.86 (1H, m), 7.88 (1H, d, J=4.9 Hz), 7.95 (1H, dd, J=11.3, 1.9 Hz), 8.14 (1H, s), 8.73 (1H, dd, J=4.7, 0.9 Hz), 9.24 (1H, t, J=5.7 Hz), 9.32 (1H, d, J=1.1 Hz).

Example 18

3-fluoro-N-([1,2,3]triazolo[1,5-b]pyridazin-3-ylmethyl)-4-(trifluoromethoxy)benzamide

A) ethyl [1,2,3]triazolo[1,5-b]pyridazine-3-carboxylate

To a mixture of ethyl pyridazin-3-ylacetate (4.38 g), 4-acetamidobenzenesulfonyl azide (7.60 g) and acetonitrile (70 ml) was added dropwise DBU (4.82 g) at 0° C. using a syringe. The mixture was allowed to warm to 30° C., and stirred at the same temperature for 2 hr. To the mixture was added saturated aqueous ammonium chloride solution, and the mixture was extracted with ethyl acetate. The combined organic layers were dried over anhydrous sodium sulfate, and concentrated under reduced pressure. The residue was purified by silica gel column chromatography (dichloromethane/methanol) to give the title compound (4.53 g).
MS: [M+H]$^+$ 193.0.

B) [1,2,3]triazolo[1,5-b]pyridazin-3-ylmethanol

To a mixture of ethyl [1,2,3]triazolo[1,5-b]pyridazine-3-carboxylate (2.10 g) and THF (150 ml) was added dropwise diisobutylaluminium hydride (1 M toluene solution, 15.0 ml) under nitrogen atmosphere at −78° C. using a syringe. The mixture was stirred at −78° C. for 2 hr, allowed to warm to −20° C., and stirred at the same temperature for 1 hr. To the mixture was added methanol (30 ml), the insoluble substance was removed by filtration, and washed with THF, and the filtrate was concentrated under reduced pressure. The residue was purified by silica gel column chromatography (dichloromethane/methanol) to give the title compound (0.82 g).
MS: [M+H]$^+$ 151.0.

C) 3-(azidomethyl)[1,2,3]triazolo[1,5-b]pyridazine

A mixture of [1,2,3]triazolo[1,5-b]pyridazin-3-ylmethanol (1.38 g), DPPA (3.04 g), DBU (1.82 g) and THF (50 ml) was stirred under nitrogen atmosphere at 30° C. for 16 hr. The reaction solution was diluted with 1 M hydrochloric acid, and the mixture was extracted with ethyl acetate. The combined organic layers were washed with saturated aqueous sodium hydrogencarbonate solution and saturated brine, dried over anhydrous sodium sulfate, and concentrated under reduced pressure. The residue was purified by silica gel column chromatography (ethyl acetate/petroleum ether) to give the title compound (1.52 g).
$^1$H NMR (400 MHz, DMSO-d$_6$) δ 4.92 (2H, s), 7.41-7.47 (1H, m), 8.62-8.69 (1H, m), 8.73-8.79 (1H, m).

D) 1-([1,2,3]triazolo[1,5-b]pyridazin-3-yl)methanamine hydrochloride

A mixture of 3-(azidomethyl) [1,2,3]triazolo[1,5-b]pyridazine (1.52 g) and triphenylphosphine (4.55 g), THF (120 ml) and 25% aqueous ammonia (30 ml) was stirred under nitrogen atmosphere at 70° C. for 1 hr. The reaction solution was concentrated, and to the residue was added 4 M hydrogen chloride/1,4-dioxane (80 ml) at 30° C. The mixture was stirred at 30° C. for 1 hr, and the reaction solution was concentrated under reduced pressure. To the residue was added ethyl acetate (150 ml), and the resulting precipitate was collected by filtration, and dried to give the title compound (1.54 g).
MS: [M+Na]$^+$ 171.9.

E) 3-fluoro-N-([1,2,3]triazolo[1,5-b]pyridazin-3-ylmethyl)-4-(trifluoromethoxy)benzamide To a mixture of 3-fluoro-4-(trifluoromethoxy)benzoic acid (1304 mg) and DMA (30 ml) were added 1-([1,2,3]triazolo[1,5-b]pyridazin-3-yl)methanamine hydrochloride (900 mg), HOBt (786 mg), WSC HCl (1115 mg) and TEA (2.70 ml) at room temperature. The mixture was stirred overnight at room temperature. To the mixture were added saturated aqueous sodium hydrogencarbonate solution and water at room temperature, and the resulting precipitate was collected by filtration, and washed with water. The solid was purified by silica gel column chromatography (NH, ethyl acetate/hexane). The obtained solid was crystallized from ethyl acetate/hexane to give the title compound (1.318 g).
$^1$H NMR (300 MHz, DMSO-d$_6$) δ 4.86 (2H, d, J=5.3 Hz), 7.38 (1H, dd, J=9.0, 4.5 Hz), 7.64-7.75 (1H, m), 7.79-7.89 (1H, m), 7.96 (1H, dd, J=11.3, 1.9 Hz), 8.58 (1H, dd, J=9.2, 1.3 Hz), 8.71 (1H, dd, J=4.3, 1.7 Hz), 9.42 (1H, t, J=5.5 Hz).

Example 23

6-(difluoromethoxy)-5-fluoro-N-([1,2,3]triazolo[1,5-b]pyridazin-3-ylmethyl)nicotinamide To a mixture of 6-(difluoromethoxy)-5-fluoronicotinic acid (2.455 g) and DMA (60 ml) were added 1-([1,2,3]triazolo[1,5-b]pyridazin-3-yl)methanamine hydrochloride (2.0 g), HOBt (1.747 g), WSC HCl (2.479 g) and TEA (6.01 ml). The mixture was stirred overnight at room temperature. The mixture was diluted with saturated aqueous sodium hydrogencarbonate solution and water, and the resulting precipitate was collected by filtration, and washed with water. The obtained solid was crystallized from dimethyl sulfoxide/2-propanol/water to give the title compound (3.05 g).
$^1$H NMR (300 MHz, DMSO-d$_6$) δ 4.87 (2H, d, J=5.3 Hz), 7.38 (1H, dd, J=9.0, 4.5 Hz), 7.79 (1H, t, J=71.2 Hz), 8.29 (1H, dd, J=10.9, 1.9 Hz), 8.54-8.62 (2H, m), 8.71 (1H, dd, J=4.3, 1.7 Hz), 9.47 (1H, brs).

Example 40

3-chloro-N-([1,2,3]triazolo[1,5-b]pyridazin-3-ylmethyl)-4-(trifluoromethoxy)benzamide To a mixture of 3-chloro-4-(trifluoromethoxy)benzoic acid (1.555 g) and DMA (35 ml) were added 1-([1,2,3]triazolo[1,5-b]pyridazin-3-yl)methanamine hydrochloride (1.0 g), HOBt (0.874 g), WSC HCl (1.239 g) and TEA (3.00 ml) at room temperature. The mixture was stirred overnight at room temperature. To the mixture were added saturated aqueous sodium hydrogencarbonate solution and water, and the resulting precipitate was collected by filtration. The solid was purified by silica gel column chromatography (NH, ethyl acetate/hexane). The obtained solid was crystallized from ethyl acetate/hexane to give the title compound (1.76 g).
$^1$H NMR (300 MHz, DMSO-d$_6$) δ 4.86 (2H, d, J=5.7 Hz), 7.38 (1H, dd, J=9.0, 4.5 Hz), 7.69 (1H, dd, J=8.7, 1.1 Hz), 7.96 (1H, dd, J=8.5, 2.1 Hz), 8.15 (1H, d, J=2.3 Hz), 8.58 (1H, dd, J=9.0, 1.9 Hz), 8.71 (1H, dd, J=4.3, 1.7 Hz), 9.44 (1H, t, J=5.1 Hz).

Example 42

3-fluoro-N-([1,2,3]triazolo[1,5-a]pyrazin-3-ylmethyl)-4-(trifluoromethoxy)benzamide

A) (1E)-N-(((4-methylphenyl)sulfonyl)oxy)-1-(pyrazin-2-yl)ethanimine

To a mixture of 1-(pyrazin-2-yl)ethanone (2.90 g) and ethanol (40 ml) were added hydroxylamine hydrochloride (2.475 g) and TEA (5.30 ml) at room temperature. The mixture was stirred overnight at room temperature. The mixture was poured into water, and extracted with ethyl acetate. The organic layer was separated, washed with saturated brine, dried over anhydrous sodium sulfate, and concentrated under reduced pressure to give a residue (3.46 g). To a mixture of the obtained residue (3.46 g) and pyridine (40 ml) was added 4-methylbenzenesulfonyl chloride (5.29 g) at room temperature. The mixture was stirred overnight at room temperature, and the reaction solution was concentrated. To the obtained residue was added ethyl acetate, and the mixture was neutralized with 2 M aqueous sodium hydroxide solution, and extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (4.77 g).

MS: [M+H]$^+$ 292.1.

B) (E)-2-((tert-butoxycarbonyl)amino)-1-(pyrazin-2-yl)vinyl tert-butyl carbonate To ethanol (10 ml) was added sodium hydride (60%, 0.332 g) at 0° C., and the mixture was stirred at room temperature for 30 min. To the reaction solution was added a solution of (1E)-N-(((4-methylphenyl)sulfonyl)oxy)-1-(pyrazin-2-yl)ethanimine (2.20 g) in a mixed solvent of ethanol (8 ml) and THF (5 ml) at 0° C., and the mixture was stirred at room temperature for 1.5 hr. To the reaction solution was added diethyl ether (75 ml), and the insoluble substance was removed by filtration. The filtrate was extracted with 2 M hydrochloric acid, and the aqueous layer was concentrated under reduced pressure to give a residue (1.30 g). To a mixture of the obtained residue (1.30 g) and THF (10 ml) were added TEA (3.13 ml) and Boc$_2$O (2.61 ml). The mixture was stirred overnight at room temperature. The mixture was diluted with water, and extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (300 mg).

MS: [M+H]$^+$ 338.1.

C) tert-butyl ([1,2,3]triazolo[1,5-a]pyrazin-3-ylmethyl)carbamate

To a mixture of (E)-2-((tert-butoxycarbonyl)amino)-1-(pyrazin-2-yl)vinyl tert-butyl carbonate (300 mg) and ethanol (5 ml) was added hydrazine monohydrate (223 mg). The mixture was refluxed for 1 hr, and concentrated. The residue was purified by silica gel column chromatography (NH, ethyl acetate/hexane) to give a crude product (166 mg). To a mixture of the crude product (164 mg) and acetonitrile (6 ml) was added iodobenzene diacetate (158 mg). The mixture was stirred at room temperature for 5 hr, and the reaction solution was concentrated. The residue was purified by silica gel column chromatography (NH, ethyl acetate/hexane) to give the title compound (55.7 mg).

MS: [M+H]$^+$ 250.0.

D) 3-fluoro-N-([1,2,3]triazolo[1,5-a]pyrazin-3-ylmethyl)-4-(trifluoromethoxy)benzamide To a mixture of tert-butyl ([1,2,3]triazolo[1,5-a]pyrazin-3-ylmethyl)carbamate (54.0 mg) and ethanol (2 ml) was added dropwise 6 M hydrochloric acid (0.181 ml) at room temperature. The mixture was stirred at room temperature for 30 min, and the reaction solution was concentrated, and subjected to azeotrope with toluene to give a residue (40.2 mg). To a mixture of the obtained residue (40.0 mg) and DMF (2 ml) were added 3-fluoro-4-(trifluoromethoxy)benzoic acid (58.0 mg), TEA (0.090 ml), WSC HCl (49.6 mg) and HOBt H$_2$O (39.6 mg) at room temperature. The mixture was stirred overnight at room temperature. To the mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (57.3 mg).

$^1$H NMR (300 MHz, DMSO-d$_6$) δ 4.95 (2H, d, J=5.7 Hz), 7.65-7.76 (1H, m), 7.84 (1H, d, J=8.7 Hz), 7.96 (1H, dd, J=11.3, 1.9 Hz), 8.10 (1H, d, J=4.9 Hz), 9.12 (1H, dd, J=4.7, 1.3 Hz), 9.47 (1H, t, J=5.3 Hz), 9.57 (1H, d, J=1.5 Hz).

Example 47

3-fluoro-N-(pyrazolo[1,5-b][1,2,4]triazin-8-ylmethyl)-4-(trifluoromethoxy)benzamide

A) 1H-pyrazole-1,5-diamine

In an ice bath containing sodium chloride, to a mixture of 1H-pyrazol-5-amine (25 g) and DMF (300 ml) was added potassium hydroxide (120 g) by small portions, and then hydroxylamine-O-sulfonic acid (34.0 g) was added thereto by small portions at the same temperature. The mixture was stirred at room temperature for 2 hr, the reaction solution was filtered through Celite, and the filtrate was concentrated under reduced pressure. The residue was purified by silica gel column chromatography (methanol/ethyl acetate) to give the title compound (1.14 g).

$^1$H NMR (300 MHz, CDCl$_3$) δ 3.80-4.19 (2H, m), 4.83 (2H, brs), 5.38 (1H, dd, J=2.2, 0.8 Hz), 7.13 (1H, d, J=1.9 Hz).

B) pyrazolo[1,5-b][1,2,4]triazine-8-carbaldehyde

To a mixture of 1H-pyrazole-1,5-diamine (2.28 g) and ethanol (20 ml) was added glyoxal (40% aqueous solution, 1.33 ml). The reaction solution was stirred at 80° C. for 2 hr. To the mixture were added glyoxal (40% aqueous solution, 0.67 ml) and ethanol (20 ml), and the mixture was stirred at 80° C. for additional 2 hr. The reaction solution was concentrated under reduced pressure to give a residue (2.48 g). To phosphoryl chloride (16.5 g) was added DMF (1.52 g) at 0° C., and the mixture was stirred under nitrogen atmosphere at 0° C. for 30 min. To the reaction solution was added a part (500 mg) of the residue at 0° C., and the mixture was stirred at 80° C. for 2 hr. The mixture was cooled to 10° C., and the reaction solution was concentrated. To the residue was added 1 M aqueous sodium hydrogencarbonate solution until the mixture reached pH 9, and the mixture was extracted with ethyl acetate. The combined organic layers were washed with water and saturated brine, dried over anhydrous sodium sulfate, and concentrated under reduced pressure. The residue was purified by silica gel column chromatography (ethyl acetate/petroleum ether) to give the title compound (239 mg).

$^1$H NMR (400 MHz, CDCl$_3$) δ 8.53 (1H, d, J=1.6 Hz), 8.65-8.81 (2H, m), 10.33 (1H, s).

C) tert-butyl (2,4-dimethoxybenzyl) (pyrazolo[1,5-b][1,2,4]triazin-8-ylmethyl)carbamate To a mixture of 1-(2,4-dimethoxyphenyl)methanamine (324 mg) and ethanol (5 ml) was added pyrazolo[1,5-b][1,2,4]triazine-8-carbaldehyde (239 mg). The mixture was stirred at 78° C. for 1 hr. The reaction solution was cooled to 25° C., and sodium borohydride (73 mg) was added thereto by small portions at 0° C. The mixture was stirred at 25° C. for 16 hr, and the reaction solution was concentrated. The obtained residue was partitioned between ethyl acetate-water, and the aqueous layer was extracted with ethyl acetate. The combined organic layers were concentrated under reduced pressure to give a residue (386 mg). To a mixture of the obtained residue (386 mg) and THF (5 ml) were added DIPEA (329 mg) and Boc$_2$O (417 mg) at 25° C. The mixture was stirred at 25° C. for 30 min, the reaction solution was diluted with water, and the mixture was extracted with ethyl acetate. The combined organic layers were washed with saturated brine, dried over anhydrous sodium sulfate, and concentrated under reduced pressure to give a residue (516 mg). To a mixture of the obtained residue (466 mg) and dichloromethane (5 ml) was added manganese dioxide (502 mg) at 25° C. The mixture was stirred at 25° C. for 16 hr. The insoluble substance was removed by filtration, and washed with dichloromethane. The filtrate was concentrated under reduced pressure, and the residue was purified by silica gel column chromatography (ethyl acetate/petroleum ether) to give the title compound (168 mg).

MS: [M+Na]$^+$422.3.

D) 3-fluoro-N-(pyrazolo[1,5-b][1,2,4]triazin-8-ylmethyl)-4-(trifluoromethoxy)benzamide A mixture of tert-butyl (2,4-dimethoxybenzyl)(pyrazolo[1,5-b][1,2,4]triazin-8-ylmethyl)carbamate (168 mg), TFA (3 ml) and dichloromethane (3 ml) was stirred at 25° C. for 16 hr. The reaction solution was concentrated, and subjected to azeotrope three times with dichloromethane to give a residue (209 mg). To a mixture of a part (159 mg) of the obtained residue and DMF (5 ml) were added 3-fluoro-4-(trifluoromethoxy)benzoic acid (238 mg), HATU (566 mg) and DIPEA (687 mg) at 25° C. The mixture was stirred under nitrogen atmosphere at 25° C. for 16 hr. To the reaction solution was added ethyl acetate, and the organic layer was separated, washed with water and saturated brine, dried over anhydrous sodium sulfate, and concentrated under reduced pressure. The residue was purified by preparative HPLC (mobile phase: water/acetonitrile (containing 0.05% aqueous ammonia)). The obtained fraction was concentrated under reduced pressure, and freeze-dried to give the title compound (32 mg).

$^1$H NMR (400 MHz, DMSO-d$_6$) δ 4.69 (2H, d, J=5.6 Hz), 7.66-7.76 (1H, m), 7.84 (1H, dd, J=8.8 Hz, J=1.2 Hz), 7.97 (1H, dd, J=11.2 Hz, J=2.0 Hz), 8.35 (1H, s), 8.57-8.68 (2H, m), 9.19 (1H, t, J=5.2 Hz).

Example 48

3-fluoro-N-((2-methylpyrazolo[1,5-c]pyrimidin-3-yl)methyl)-4-(trifluoromethoxy)benzamide A) 1-(2-(methylsulfanyl)pyrimidin-4-yl)acetone To a mixture of 4-methyl-2-(methylsulfanyl)pyrimidine (11.5 g) and THF (300 ml) was added dropwise lithium hexamethyldisilazide (1 M THF solution, 164 ml) under nitrogen atmosphere at 0° C. The mixture was stirred at 0° C. for 30 min, and to the reaction solution was added dropwise ethyl acetate (14.5 g) at 0° C. The mixture was allowed to warm to 30° C., and stirred at the same temperature for 15.5 hr. The reaction solution was diluted with water, and the mixture was extracted with ethyl acetate. The combined organic layers were dried over anhydrous sodium sulfate, and concentrated under reduced pressure. The residue was purified by silica gel column chromatography (ethyl acetate/petroleum ether) to give the title compound (9.66 g).

MS: [M+H]$^+$ 183.0.

B) (2E)-N-hydroxy-1-(2-(methylsulfanyl)pyrimidin-4-yl)propan-2-imine

A mixture of at 1-(2-(methylsulfanyl)pyrimidin-4-yl)acetone (9.66 g), hydroxylamine hydrochloride (18.4 g), 3 M aqueous sodium hydroxide solution (88.3 ml) and methanol (150 ml) was stirred at 80° C. for 2 hr. The reaction solution was concentrated, to the obtained residue was added water, and the mixture was extracted with ethyl acetate. The combined organic layers were dried over anhydrous sodium sulfate, and concentrated under reduced pressure. The residue was purified by silica gel column chromatography (ethyl acetate/petroleum ether) to give the title compound (8.05 g).

MS: [M+H]$^+$ 198.0.

C) 2-methyl-7-(methylsulfanyl)pyrazolo[1,5-c]pyrimidine

To a mixture of (2E)-N-hydroxy-1-(2-(methylsulfanyl)pyrimidin-4-yl)propan-2-imine (8.05 g) and THF (100 ml) were added dropwise trifluoroacetic anhydride (8.57 g) and TEA (8.26 g) at 0° C. The mixture was stirred at 30° C. for 2 hr, and to the reaction solution was added iron(II) chloride (0.52 g) at 30° C. The mixture was stirred at 80° C. for 16 hr, and the reaction solution was concentrated. The residue was purified by silica gel column chromatography (ethyl acetate/petroleum ether) to give the title compound (4.20 g).

MS: [M+H]$^+$ 180.0.

D) 2-methyl-7-(methylsulfanyl)pyrazolo[1,5-c]pyrimidine-3-carbaldehyde

To a mixture of 2-methyl-7-(methylsulfanyl)pyrazolo[1,5-c]pyrimidine (4.20 g) and DMF (150 ml) was added dropwise phosphoryl chloride (7.19 g) at 25° C. The mixture was stirred at 25° C. for 16 hr. The mixture was poured into water, and the resulting solid was collected by filtration, and washed with water to give the title compound (4.33 g).

MS: [M+H]$^+$ 208.0.

E) 2-methylpyrazolo[1,5-c]pyrimidine-3-carbaldehyde

To a mixture of 2-methyl-7-(methylsulfanyl)pyrazolo[1,5-c]pyrimidine-3-carbaldehyde (4.75 g) and THF (250 ml)

was added Raney nickel (8.60 g) under nitrogen atmosphere at 25° C. The mixture was stirred under hydrogen atmosphere of 50 psi, at 60° C. for 48 hr. The catalyst was removed by filtration, and the filtrate was concentrated under reduced pressure. The residue was purified by silica gel column chromatography (ethyl acetate/petroleum ether) to give the title compound (1.85 g).

MS: [M+H]$^+$ 162.1.

F) (2-methylpyrazolo[1,5-c]pyrimidin-3-yl)methanol

To a mixture of 2-methylpyrazolo[1,5-c]pyrimidine-3-carbaldehyde (1.85 g), methanol (50 ml) and THF (50 ml) was added sodium borohydride (0.65 g) by small portions under nitrogen atmosphere at 0° C. The mixture was stirred at 0° C. for 1 hr. To the mixture was added water, and the mixture was concentrated under reduced pressure. The residue was purified by silica gel column chromatography (dichloromethane/methanol) to give the title compound (1.33 g).

MS: [M+H]$^+$ 164.1.

G) 3-(azidomethyl)-2-methylpyrazolo[1,5-c]pyrimidine

A mixture of (2-methylpyrazolo[1,5-c]pyrimidin-3-yl)methanol (1.33 g), DPPA (2.69 g), DBU (1.61 g) and THF (50 ml) was stirred under nitrogen atmosphere at 25° C. for 16 hr. To the reaction solution was added 1 M hydrochloric acid, and the mixture was extracted with ethyl acetate. The organic layer was separated, washed with saturated aqueous sodium hydrogencarbonate solution and saturated brine, dried over anhydrous sodium sulfate, and concentrated under reduced pressure. The residue was purified by silica gel column chromatography (ethyl acetate/petroleum ether) to give the title compound (1.07 g).

MS: [M+H]$^+$ 189.1.

H) 1-(2-methylpyrazolo[1,5-c]pyrimidin-3-yl)methanamine hydrochloride

A mixture of 3-(azidomethyl)-2-methylpyrazolo[1,5-c]pyrimidine (1.07 g), THF (20 ml), 25% aqueous ammonia (5 ml) and triphenylphosphine (2.70 g) was stirred under nitrogen atmosphere at 70° C. for 1 hr. The reaction solution was concentrated, and to the residue was added 4 M hydrogen chloride/ethyl acetate (20 ml) at 25° C. The mixture was stirred at 25° C. for 1 hr, and the reaction solution was concentrated. To the obtained residue was added ethyl acetate, and the resulting precipitate was collected by filtration to give the title compound (1.05 g).

MS: [M+H]$^+$ 163.1.

I) 3-fluoro-N-((2-methylpyrazolo[1,5-c]pyrimidin-3-yl)methyl)-4-(trifluoromethoxy)benzamide To a mixture of 1-(2-methylpyrazolo[1,5-c]pyrimidin-3-yl)methanamine hydrochloride (85 mg) and DMF (5 ml) were added 3-fluoro-4-(trifluoromethoxy)benzoic acid (85 mg), HOBt (76.9 mg), WSC HCl (109 mg) and TEA (182 mg). The mixture was stirred at 25° C. for 16 hr. The reaction solution was diluted with water, and the mixture was extracted with ethyl acetate. The combined organic layers were dried over anhydrous sodium sulfate, and concentrated under reduced pressure. The residue was purified by preparative HPLC (mobile phase: water/acetonitrile (containing 0.05% aqueous ammonia)) to give the title compound (51 mg).

$^1$H NMR (400 MHz, CDCl$_3$) δ 2.54 (3H, s), 4.73 (2H, d, J=5.2 Hz), 6.26 (1H, brs), 7.32-7.40 (1H, m), 7.46-7.50 (1H, m), 7.51-7.56 (1H, m), 7.62-7.69 (1H, m), 7.78-7.83 (1H, m), 9.09-9.15 (1H, m).

Example 58

6-(difluoromethoxy)-5-fluoro-N-((1-methyl-1H-imidazo[1,2-b]pyrazol-7-yl)methyl)nicotinamide (this Compound is Also Named as 6-(difluoromethoxy)-5-fluoro-N-[(1-methyl-1H-imidazo[1,2-b]pyrazol-7-yl)methyl]pyridine-3-carboxamide)

A) 5-amino-1-(2,2-diethoxyethyl)-1H-pyrazole-4-carbonitrile

To a mixture of hydrazine monohydrate (68.0 g) and ethanol (225 ml) was added 2-bromo-1,1-diethoxyethane (59.0 ml) at 100° C. The mixture was heated under reflux for 2 hr, and the reaction solution was concentrated under reduced pressure. To the obtained residue was added 1 M aqueous sodium hydroxide solution (94.0 ml) containing sodium chloride (11.25 g) at room temperature, and the mixture was extracted twice with diethyl ether. The organic layer was separated, dried over anhydrous sodium sulfate, and concentrated under reduced pressure to give a residue (28.1 g). To a mixture of the obtained residue (28.06 g) and ethanol (300 ml) was added a solution of (ethoxymethylene) malononitrile (23.12 g) in ethanol (100 ml) at room temperature. The mixture was stirred at room temperature for 16 hr, and concentrated under reduced pressure. The residue was purified by silica gel column chromatography (NH, ethyl acetate/hexane) to give the title compound (22.65 g).

MS: [M−H]$^-$ 223.0.

B) 1H-imidazo[1,2-b]pyrazole-7-carbonitrile

A solution of 5-amino-1-(2,2-diethoxyethyl)-1H-pyrazole-4-carbonitrile (22.65 g) in ethanol (36.0 ml) was added to a mixed solution of conc. sulfuric acid (36.0 ml) and water (146 ml) at 0° C. The mixture was heated under reflux for 30 min, allowed to cool to room temperature, and poured into ice. The mixture was neutralized with solid sodium hydrogencarbonate at 0° C., and extracted with ethyl acetate. The resulting precipitate was collected by filtration, and the obtained solid was washed with water and ethyl acetate to give the title compound (5.71 g).

MS: [M+H]$^+$ 133.1.

Then, the organic phase of the filtrate was separated, washed with water and saturated brine, dried over anhydrous sodium sulfate, and concentrated under reduced pressure. The residue was washed with ethyl acetate and diisopropyl ether to give the title compound (6.16 g).

C) 1-methyl-1H-imidazo[1,2-b]pyrazole-7-carbonitrile

To a mixture of sodium hydride (60%, 0.541 g) and DMF (10.0 ml) was added a solution of 1H-imidazo[1,2-b]pyrazole-7-carbonitrile (1.49 g) in DMF (10.0 ml) at 0° C. The mixture was stirred at room temperature for 10 min, to the reaction mixture was added a solution of iodomethane (0.846 ml) in DMF (10.0 ml) at 0° C. The mixture was stirred at room temperature for 5 hr. To the mixture was added saturated aqueous ammonium chloride solution at room temperature, and the mixture was extracted with ethyl acetate. The organic layer was separated, washed with water and saturated brine, dried over anhydrous sodium sulfate, and concentrated under reduced pressure. The residue was washed with diisopropyl ether to give the title compound (937 mg).

MS: [M+H]⁺ 147.2.

Then, the filtrate was concentrated under reduced pressure, and the residue was purified by silica gel column chromatography (ethyl acetate/hexane) to give the title compound (420.9 mg).

D) 1-(1-methyl-1H-imidazo[1,2-b]pyrazol-7-yl)methanamine

A mixture of l-methyl-1H-imidazo[1,2-b]pyrazole-7-carbonitrile (4.73 g), 7 M ammonia/methanol (40 ml) and Raney nickel (25% wt, 1.25 g) was stirred under hydrogen atmosphere of 5 MPa, at 90° C. for 5 hr. The insoluble substance (catalyst) was removed by filtration, and the filtrate was concentrated under reduced pressure to give the title compound (4.90 g).

MS: [M+H]⁺ 151.0.

E) 6-(difluoromethoxy)-5-fluoro-N-((1-methyl-1H-imidazo[1,2-b]pyrazol-7-yl)methyl)nicotinamide To a mixture of 6-(difluoromethoxy)-5-fluoronicotinic acid (4.14 g), DMF (60.0 ml), 1-(1-methyl-1H-imidazo[1,2-b]pyrazol-7-yl)methanamine (3.00 g), WSC HCl (4.60 g) and HOBt (3.24 g) was added TEA (6.96 ml) at 0° C. The mixture was stirred overnight (for 16 hr) at room temperature. To the reaction mixture was added water at room temperature, and the mixture was extracted with ethyl acetate. The organic layer was separated, washed with water and saturated brine, dried over anhydrous sodium sulfate, and concentrated under reduced pressure. The residue was washed with ethyl acetate to give a solid. The filtrate was concentrated under reduced pressure, and the residue was purified by silica gel column chromatography (NH, ethyl acetate/hexane). The obtained solids were crystallized from ethyl acetate/heptane to give the title compound (3.29 g). The solids separately obtained by a method analogous to the above were employed in Experimental Examples 1 and 2. The crystallization was performed as follows.

First, the above-mentioned collected solid was dissolved in ethyl acetate (550 ml) at 70° C., heptane (180 ml) was added thereto at 70° C., and the mixture was stirred at 70° C. for 30 min. Next, to the mixture was added heptane (20 ml) at 70° C., and the mixture was stirred at 70° C. for 30 min, allowed to cool gradually to room temperature, stirred overnight at room temperature, and then at 0° C. for 3 hr. The precipitated solid was collected by filtration, and washed with heptane to give the title compound as crystals.

¹H NMR (300 MHz, DMSO-de) δ 3.72 (3H, s), 4.50 (2H, d, J=4.9 Hz), 7.12 (1H, d, J=1.5 Hz), 7.48 (2H, dd, J=3.2, 1.7 Hz), 7.54-8.05 (1H, m), 8.30 (1H, dd, J=10.7, 2.1 Hz), 8.55 (1H, d, J=1.9 Hz), 8.97 (1H, t, J=5.1 Hz).

The obtained crystal was characterized by having specific peaks at the two theta of 7.5°±0.2°, 13.0°±0.2°, 14.9°±0.2°, 16.5°±0.2°, 17.3°±0.2°, 19.0°±0.2°, 22.4°±0.2°, 24.8°±0.2°, 25.4°±0.2° and 30.1°±0.2° degrees in a powder X-ray diffraction pattern.

F) 6-(difluoromethoxy)-5-fluoro-N-((1-methyl-1H-imidazo[1,2-b]pyrazol-7-yl)methyl)nicotinamide A mixture of (1-methyl-1H-imidazo[1,2-b]pyrazol-7-yl)methanamine (8.70 g, 57.93 mmol), 6-(difluoromethoxy)-5-fluoronicotinic acid (12.00 g, 57.93 mmol), WSC HCl (16.66 g, 86.90 mmol), HOBt (9.39 g, 69.52 mmol), TEA (24.22 ml, 173.79 mmol), and DMF (200 ml) was stirred at room temperature overnight. Water (300 mL) was added to the mixture and the resulting solid was collected. The solid was dissolved in acetone (170 mL) and water (10 mL) at reflux. Then water (160 mL) was added dropwise at 60° C. over 15 min. The mixture was stirred at room temperature overnight and the resulting solid was collected to give the title compound (11.10 g) as crystals. This compound was employed in Experimental Example 3.

¹H NMR (300 MHz, DMSO-ds) δ 3.72 (3H, s), 4.50 (2H, d, J=4.9 Hz), 7.12 (1H, dd, J=2.3, 1.5 Hz), 7.45-7.50 (2H, m), 7.52-8.05 (1H, m), 8.30 (1H, dd, J=10.9, 1.9 Hz), 8.55 (1H, d, J=1.9 Hz), 8.97 (1H, t, J=4.9 Hz).

The obtained crystal was characterized by having specific peaks at the two theta of 7.5° 0.2°, 15.1°±0.2°, 16.8° 00.20, 22.7°±0.2°, 25.4°±0.2° and 30.4°±0.2° degrees in a powder X-ray diffraction pattern.

The compounds of Examples are shown in the following Table 1. MS in the tables means actual measured value. The compounds of Examples 3 to 5, 7, 9 to 12, 14, 15, 17, 19 to 22, 24 to 39, 41, 43 to 46, 49 to 57 and 59 to 85 in the following tables were synthesized according to the methods shown in the above-mentioned Examples or a method analogous thereto.

TABLE 1

| EXAMPLE | IUPAC NAME | Structure | ADDITIVE | MS |
|---|---|---|---|---|
| 1 | N-((6-fluoro[1,2,3]triazolo[1,5-a]pyridin-3-yl)methyl)-4-(trifluoromethoxy)benzamide | 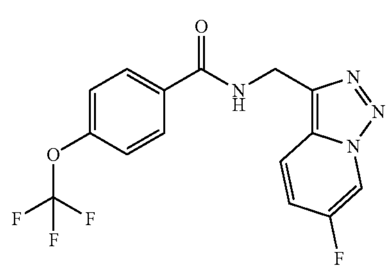 [SMILES: O=C(NCc1nnn2cc(F)ccc12)c1ccc(OC(F)(F)F)cc1] | | 352.9 |

TABLE 1-continued

| EXAMPLE | IUPAC NAME | Structure | ADDITIVE | MS |
|---|---|---|---|---|
| 2 | N-((4-methyl[1,2,3]triazolo[1,5-a]pyridin-3-yl)methyl)-4-(trifluoromethoxy)benzamide | 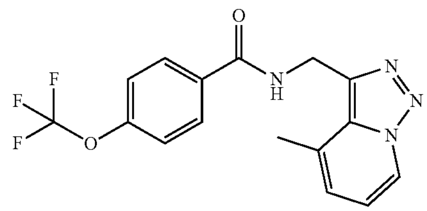 [SMILES: Cc1cccn2nnc(CNC(=O)c3ccc(OC(F)(F)F)cc3)c12] | | 351.1 |
| 3 | 3-chloro-4-(difluoromethoxy)-N-((4-methyl[1,2,3]triazolo[1,5-a]pyridin-3-yl)methyl)benzamide | 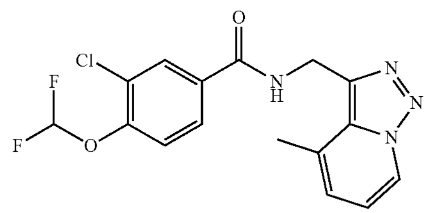 [SMILES: Cc1cccn2nnc(CNC(=O)c3ccc(OC(F)F)c(Cl)c3)c12] | | 367.1 |
| 4 | 5-fluoro-6-methoxy-N-(pyrazolo[1,5-b]pyridazin-3-ylmethyl)nicotinamide | 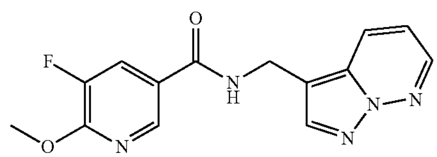 | | 302.1 |
| 5 | 3-fluoro-N-(pyrazolo[1,5-b]pyridazin-3-ylmethyl)-4-(trifluoromethoxy)benzamide | 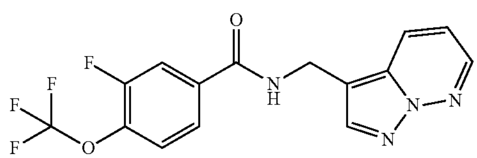 [SMILES: O=C(NCc1cnn2ncccc12)c1ccc(OC(F)(F)F)c(F)c1] | | 355.1 |
| 6 | 6-(difluoromethoxy)-5-fluoro-N-(pyrazolo[1,5-b]pyridazin-3-ylmethyl)nicotinamide | 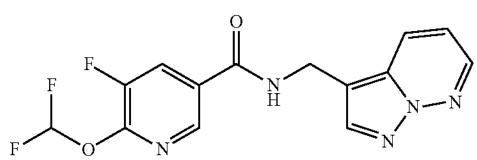 [SMILES: O=C(NCc1cnn2ncccc12)c1cnc(OC(F)F)c(F)c1] | | 336.0 |
| 7 | 3-chloro-4-(difluoromethoxy)-N-(pyrazolo[1,5-b]pyridazin-3-ylmethyl)benzamide | 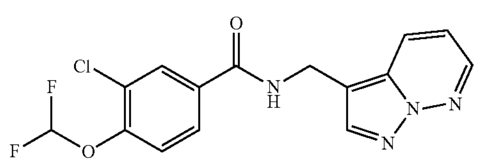 [SMILES: O=C(NCc1cnn2ncccc12)c1ccc(OC(F)F)c(Cl)c1] | | 350.9 |
| 8 | 5-chloro-6-(difluoromethoxy)-N-(pyrazolo[1,5-b]pyridazin-3-ylmethyl)nicotinamide | 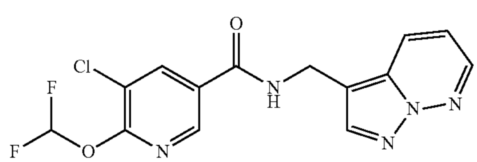 [SMILES: O=C(NCc1cnn2ncccc12)c1cnc(OC(F)F)c(Cl)c1] | | 351.9 |
| 9 | 5-chloro-6-methoxy-N-(pyrazolo[1,5-b]pyridazin-3-ylmethyl)nicotinamide | 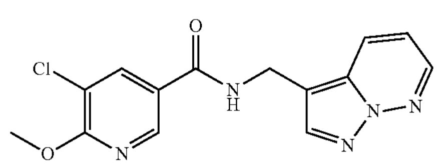 [SMILES: COc1ncc(C(=O)NCc2cnn3ncccc23)cc1Cl] | | 318.2 |
| 10 | 3-fluoro-N-((2-methylpyrazolo[1,5-b]pyridazin-3-yl)methyl)-4-(trifluoromethoxy)benzamide | 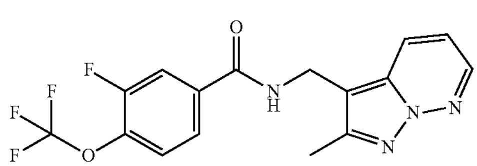 [SMILES: Cc1nn2ncccc2c1CNC(=O)c1ccc(OC(F)(F)F)c(F)c1] | | 369.1 |

TABLE 1-continued

| EXAMPLE | IUPAC NAME | Structure | ADDITIVE | MS |
|---|---|---|---|---|
| 11 | 3-fluoro-N-((6-methylpyrazolo[1,5-b]pyridazin-3-yl)methyl)-4-(trifluoromethoxy)benzamide | 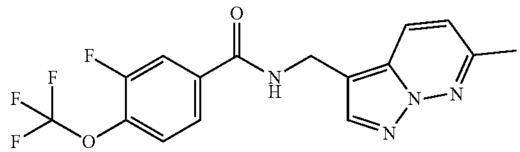 [SMILES: Cc1ccc2c(CNC(=O)c3ccc(OC(F)(F)F)c(F)c3)cnn2n1] | | 369.1 |
| 12 | 3,5-difluoro-4-methoxy-N-(pyrazolo[1,5-b]pyridazin-3-ylmethyl)benzamide | 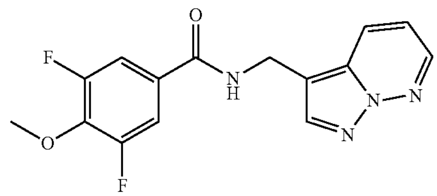 [SMILES: COc1c(F)cc(C(=O)NCc2cnn3ncccc23)cc1F] | | 319.2 |
| 13 | 3-fluoro-N-([1,2,3]triazolo[1,5-a]pyridin-3-ylmethyl)-4-(trifluoromethoxy)benzamide | 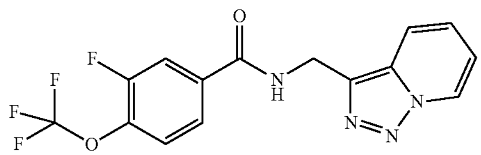 [SMILES: O=C(NCc1nnn2ccccc12)c1ccc(OC(F)(F)F)c(F)c1] | | 355.1 |
| 14 | 6-(difluoromethoxy)-5-fluoro-N-([1,2,3]triazolo[1,5-a]pyridin-3-ylmethyl)nicotinamide | 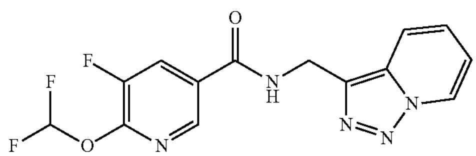 [SMILES: O=C(NCc1nnn2ccccc12)c1cnc(OC(F)F)c(F)c1] | | 338.2 |
| 15 | 4-(difluoromethoxy)-3-fluoro-N-(pyrazolo[1,5-b]pyridazin-3-ylmethyl)benzamide | 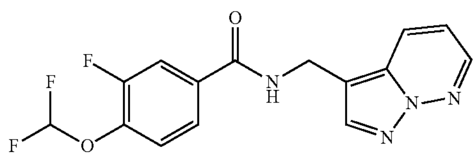 | | 337.1 |
| 16 | 3-fluoro-N-(pyrazolo[1,5-a]pyrazin-3-ylmethyl)-4-(trifluoromethoxy)benzamide | 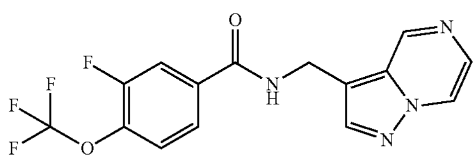 | | 355.1 |
| 17 | 6-(difluoromethoxy)-5-fluoro-N-((2-methylpyrazolo[1,5-b]pyridazin-3-yl)methyl)nicotinamide | 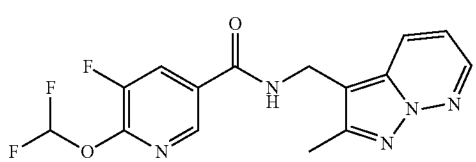 [SMILES: Cc1nn2ncccc2c1CNC(=O)c1cnc(OC(F)F)c(F)c1] | | 350.0 |
| 18 | 3-fluoro-N-([1,2,3]triazolo[1,5-b]pyridazin-3-ylmethyl)-4-(trifluoromethoxy)benzamide | 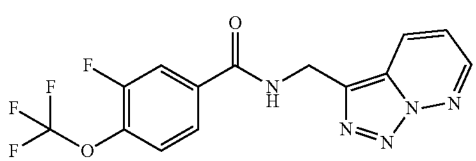 | | 353.9 |
| 19 | N-([1,2,3]triazolo[1,5-b]pyridazin-3-ylmethyl)-4-(trifluoromethoxy)benzamide | 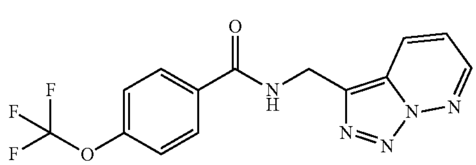 [SMILES: O=C(NCc1nnn2ncccc12)c1ccc(OC(F)(F)F)cc1] | | 336.0 |

TABLE 1-continued

| EXAMPLE | IUPAC NAME | Structure | ADDITIVE | MS |
|---|---|---|---|---|
| 20 | 3-fluoro-N-((4-methylpyrazolo[1,5-b]pyridazin-3-yl)methyl)-4-(trifluoromethoxy)benzamide | 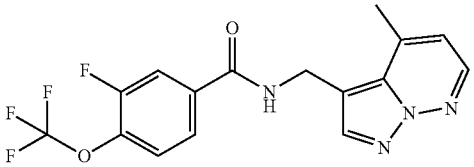 [SMILES: Cc1ccnn2ncc(CNC(=O)c3ccc(OC(F)(F)F)c(F)c3)c12] | | 369.1 |
| 21 | 3-fluoro-N-((5-methylpyrazolo[1,5-b]pyridazin-3-yl)methyl)-4-(trifluoromethoxy)benzamide | 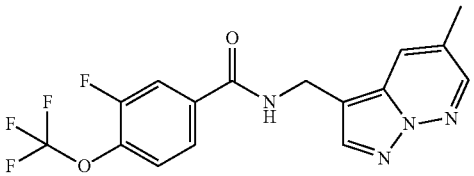 [SMILES: Cc1cnn2ncc(CNC(=O)c3ccc(OC(F)(F)F)c(F)c3)c2c1] | | 369.1 |
| 22 | 5-chloro-6-(difluoromethoxy)-N-([1,2,3]triazolo[1,5-b]pyridazin-3-ylmethyl)nicotinamide | 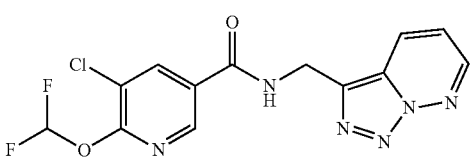 | | 352.9 |
| 23 | 6-(difluoromethoxy)-5-fluoro-N-([1,2,3]triazolo[1,5-b]pyridazin-3-ylmethyl)nicotinamide | 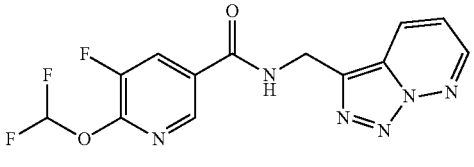 [SMILES: O=C(NCc1nnn2ncccc12)c1cnc(OC(F)F)c(Cl)c1] | | 336.9 |
| 24 | 6-(difluoromethoxy)-N-((2-ethoxypyrazolo[1,5-b]pyridazin-3-yl)methyl)-5-fluoronicotinamide | 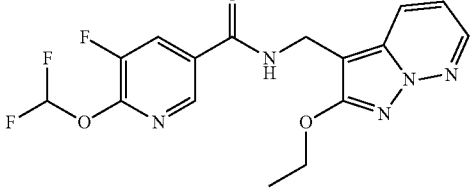 | | 380.1 |
| 25 | 4-(difluoromethoxy)-N-((2-ethoxypyrazolo[1,5-b]pyridazin-3-yl)methyl)-3-fluorobenzamide | 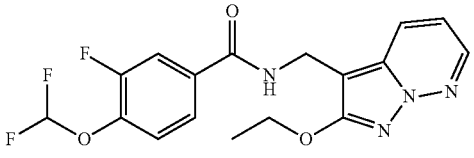 [SMILES: CCOc1nn2ncccc2c1CNC(=O)c1ccc(OC(F)F)c(F)c1] | | 379.1 |
| 26 | 6-(difluoromethoxy)-N-((2-ethylpyrazolo[1,5-b]pyridazin-3-yl)methyl)-5-fluoronicotinamide | 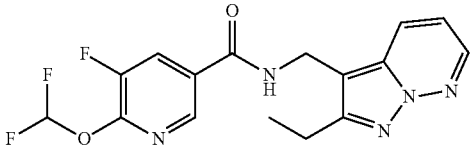 [SMILES: CCc1nn2ncccc2c1CNC(=O)c1cnc(OC(F)F)c(F)c1] | | 364.0 |
| 27 | 4-(difluoromethoxy)-N-((2-ethylpyrazolo[1,5-b]pyridazin-3-yl)methyl)-3-fluorobenzamide | 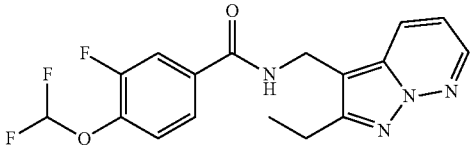 [SMILES: CCc1nn2ncccc2c1CNC(=O)c1ccc(OC(F)F)c(F)c1] | | 365.2 |
| 28 | N-((2-cyclopropylpyrazolo[1,5-b]pyridazin-3-yl)methyl)-6-(difluoromethoxy)-5-fluoronicotinamide | 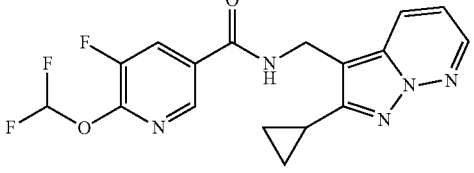 | | 376.0 |

TABLE 1-continued

| EXAMPLE | IUPAC NAME | Structure | ADDITIVE | MS |
|---|---|---|---|---|
| 29 | N-((2-cyclopropylpyrazolo[1,5-b]pyridazin-3-yl)methyl)-4-(difluoromethoxy)-3-fluorobenzamide | 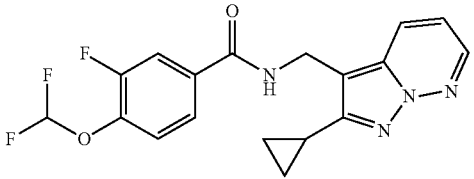 [SMILES: O=C(NCc1c(C2CC2)nn2ncccc12)c1ccc(OC(F)F)c(F)c1] | | 377.2 |
| 30 | 3-chloro-4-(difluoromethoxy)-N-([1,2,3]triazolo[1,5-b]pyridazin-3-ylmethyl)benzamide | 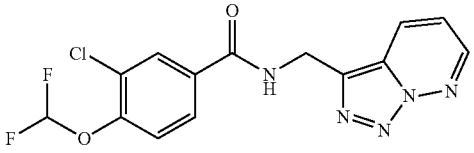 [SMILES: O=C(NCc1nnn2ncccc12)c1ccc(OC(F)F)c(Cl)c1] | | 351.8 |
| 31 | 6-(difluoromethoxy)-5-fluoro-N-((2-(methoxymethyl)pyrazolo[1,5-b]pyridazin-3-yl)methyl)nicotinamide | 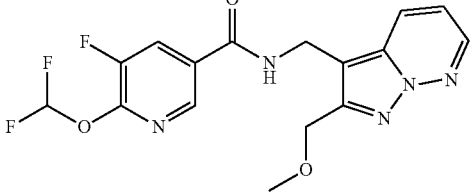 | | 380.1 |
| 32 | 3-fluoro-N-((2-(methoxymethyl)pyrazolo[1,5-b]pyridazin-3-yl)methyl)-4-(trifluoromethoxy)benzamide | 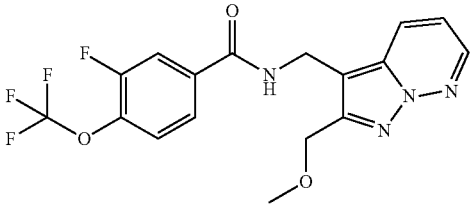 [SMILES: COCc1nn2ncccc2c1CNC(=O)c1ccc(OC(F)(F)F)c(F)c1] | | 397.0 |
| 33 | 4-(difluoromethoxy)-3-fluoro-N-([1,2,3]triazolo[1,5-b]pyridazin-3-ylmethyl)benzamide | 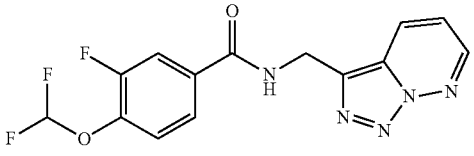 [SMILES: O=C(NCc1nnn2ncccc12)c1ccc(OC(F)F)c(F)c1] | | 338.2 |
| 34 | 3-chloro-4-(difluoromethoxy)-N-([1,2,3]triazolo[1,5-a]pyridin-3-ylmethyl)benzamide | 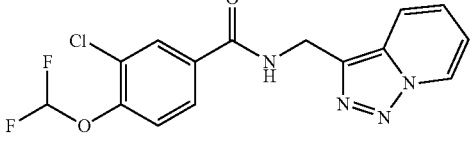 | | 353.1 |
| 35 | 4-(difluoromethoxy)-3-fluoro-N-([1,2,3]triazolo[1,5-a]pyridin-3-ylmethyl)benzamide | 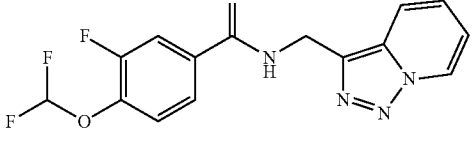 | | 337.1 |
| 36 | 4-(difluoromethoxy)-3-fluoro-N-((4-methylpyrazolo[1,5-b]pyridazin-3-yl)methyl)benzamide | 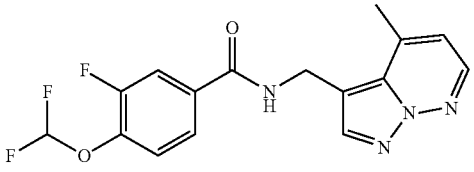 [SMILES: Cc1ccnn2ncc(CNC(=O)c3ccc(OC(F)F)c(F)c3)c12] | | 351.1 |

TABLE 1-continued

| EXAMPLE | IUPAC NAME | Structure | ADDITIVE | MS |
|---------|-----------|-----------|----------|-----|
| 37 | 6-(difluoromethoxy)-5-fluoro-N-((4-methylpyrazolo[1,5-b]pyridazin-3-yl)methyl)nicotinamide | 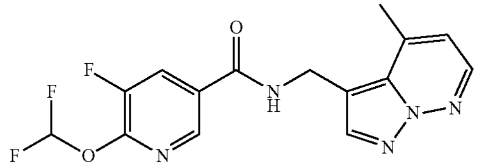 [SMILES: Cc1ccnn2ncc(CNC(=O)c3cnc(OC(F)F)c(F)c3)c12] | | 350.0 |
| 38 | 4-(difluoromethoxy)-3-fluoro-N-((5-methylpyrazolo[1,5-b]pyridazin-3-yl)methyl)benzamide | 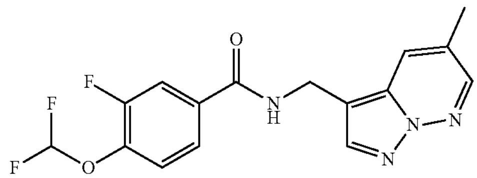 [SMILES: Cc1cnn2ncc(CNC(=O)c3ccc(OC(F)F)c(F)c3)c2c1] | | 351.1 |
| 39 | 6-(difluoromethoxy)-5-fluoro-N-((5-methylpyrazolo[1,5-b]pyridazin-3-yl)methyl)nicotinamide | 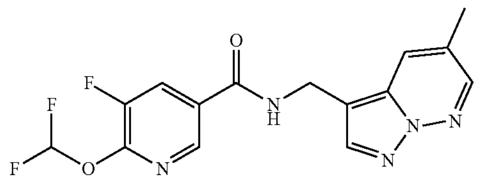 [SMILES: Cc1cnn2ncc(CNC(=O)c3cnc(OC(F)F)c(F)c3)c2c1] | | 352.2 |
| 40 | 3-chloro-N-([1,2,3]triazolo[1,5-b]pyridazin-3-ylmethyl)-4-(trifluoromethoxy)benzamide | 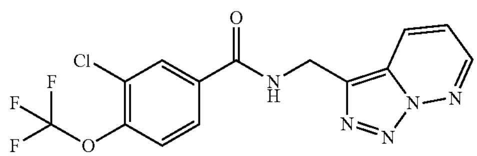 [SMILES: O=C(NCc1nnn2ncccc12)c1ccc(OC(F)(F)F)c(Cl)c1] | | 369.9 |
| 41 | 3,5-difluoro-4-methoxy-N-([1,2,3]triazolo[1,5-a]pyridin-3-ylmethyl)benzamide | 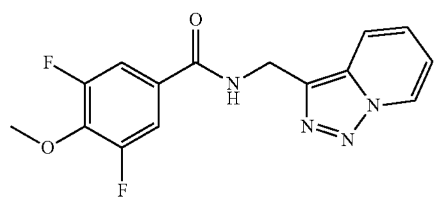 [SMILES: COc1c(F)cc(C(=O)NCc2nnn3ccccc23)cc1F] | | 319.1 |
| 42 | 3-fluoro-N-([1,2,3]triazolo[1,5-a]pyrazin-3-ylmethyl)-4-(trifluoromethoxy)benzamide | 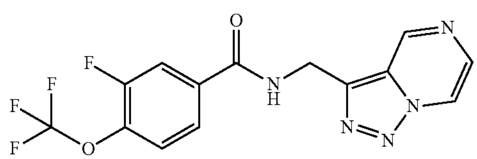 [SMILES: O=C(NCc1nnn2ccncc12)c1ccc(OC(F)(F)F)c(F)c1] | | 354.0 |
| 43 | 6-(difluoromethoxy)-N-((2-(difluoromethyl)pyrazolo[1,5-b]pyridazin-3-yl)methyl)-5-fluoronicotinamide | 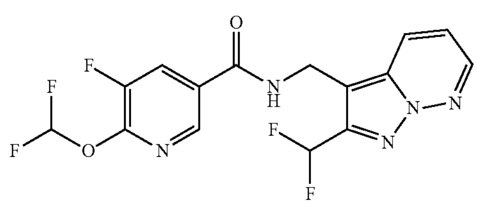 [SMILES: O=C(NCc1c(C(F)F)nn2ncccc12)c1cnc(OC(F)F)c(F)c1] | | 386.0 |
| 44 | 4-(difluoromethoxy)-3-fluoro-N-(pyrazolo[1,5-a]pyrazin-3-ylmethyl)benzamide | 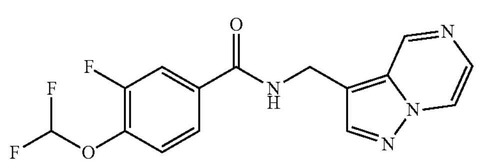 [SMILES: O=C(NCc1cnn2ccncc12)c1ccc(OC(F)F)c(F)c1] | | 337.1 |
| 45 | 6-(difluoromethoxy)-5-fluoro-N-(pyrazolo[1,5-a]pyrazin-3-ylmethyl)nicotinamide | 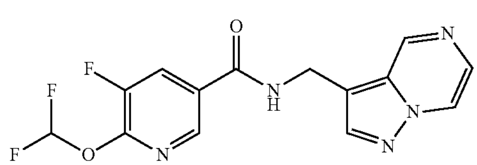 | | 338.1 |

TABLE 1-continued

| EXAMPLE | IUPAC NAME | Structure | ADDITIVE | MS |
|---|---|---|---|---|
| 46 | 5-chloro-6-(difluoromethoxy)-N-((2-methylpyrazolo[1,5-b]pyridazin-3-yl)methyl)nicotinamide | 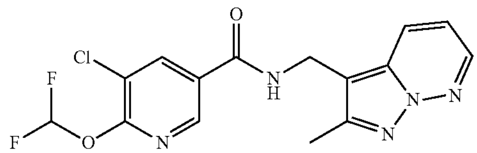 [SMILES: Cc1nn2ncccc2c1CNC(=O)c1cnc(OC(F)F)c(Cl)c1] | | 368.1 |
| 47 | 3-fluoro-N-(pyrazolo[1,5-b][1,2,4]triazin-8-ylmethyl)-4-(trifluoromethoxy)benzamide | 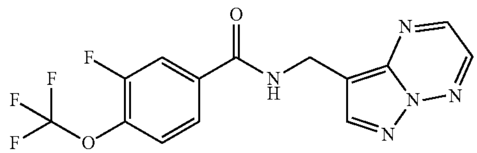 [SMILES: O=C(NCc1cnn2nccnc12)c1ccc(OC(F)(F)F)c(F)c1] | | 354.0 |
| 48 | 3-fluoro-N-((2-methylpyrazolo[1,5-c]pyrimidin-3-yl)methyl)-4-(trifluoromethoxy)benzamide | 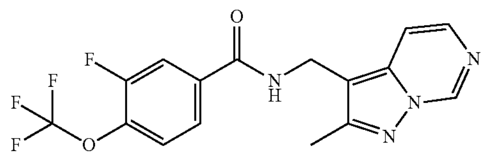 [SMILES: Cc1nn2cnccc2c1CNC(=O)c1ccc(OC(F)(F)F)c(F)c1] | | 366.9 |
| 49 | 3-fluoro-N-((5-methyl[1,2,3]triazolo[1,5-b]pyridazin-3-yl)methyl)-4-(trifluoromethoxy)benzamide | 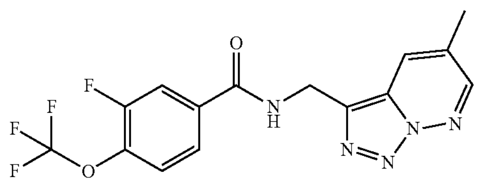 [SMILES: Cc1cnn2nnc(CNC(=O)c3ccc(OC(F)(F)F)c(F)c3)c2c1] | | 370.1 |
| 50 | 6-(difluoromethoxy)-5-fluoro-N-((5-methyl[1,2,3]triazolo[1,5-b]pyridazin-3-yl)methyl)nicotinamide | 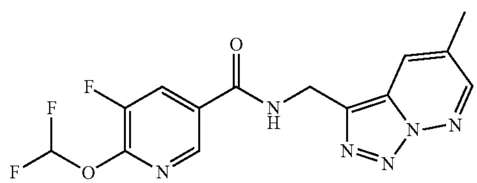 | | 350.9 |
| 51 | 5-chloro-6-(difluoromethoxy)-N-((5-methyl[1,2,3]triazolo[1,5-b]pyridazin-3-yl)methyl)nicotinamide | 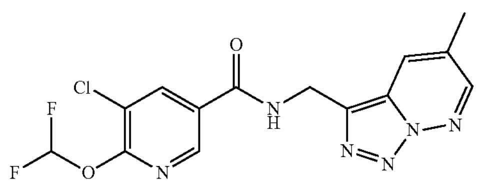 [SMILES: Cc1cnn2nnc(CNC(=O)c3cnc(OC(F)F)c(Cl)c3)c2c1] | | 367.0 |
| 52 | 3-fluoro-N-((4-methyl[1,2,3]triazolo[1,5-b]pyridazin-3-yl)methyl)-4-(trifluoromethoxy)benzamide | 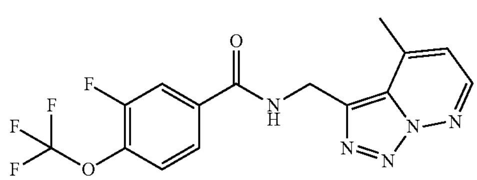 [SMILES: Cc1ccnn2nnc(CNC(=O)c3ccc(OC(F)(F)F)c(F)c3)c12] | | 370.2 |
| 53 | 6-(difluoromethoxy)-5-fluoro-N-((4-methyl[1,2,3]triazolo[1,5-b]pyridazin-3-yl)methyl)nicotinamide | 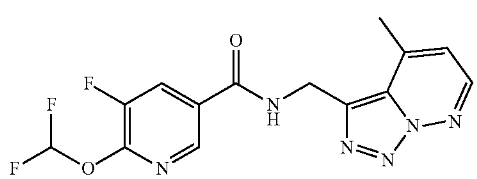 | | 353.1 |
| 54 | 5-chloro-6-(difluoromethoxy)-N-((4-methyl[1,2,3]triazolo[1,5-b]pyridazin-3-yl)methyl)nicotinamide | 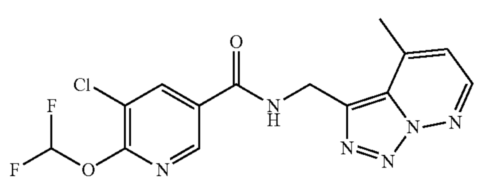 [SMILES: Cc1ccnn2nnc(CNC(=O)c3cnc(OC(F)F)c(Cl)c3)c12] | | 367.0 |

TABLE 1-continued

| EXAMPLE | IUPAC NAME | Structure | ADDITIVE | MS |
|---|---|---|---|---|
| 55 | 6-(difluoromethoxy)-5-fluoro-N-((2-methylpyrazolo[1,5-c]pyrimidin-3-yl)methyl)nicotinamide | 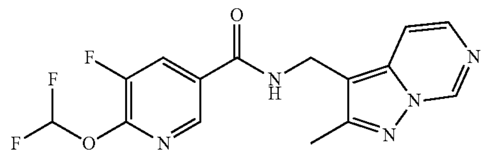 | | 350.0 |
| 56 | 5-chloro-6-(difluoromethoxy)-N-((2-methylpyrazolo[1,5-c]pyrimidin-3-yl)methyl)nicotinamide | 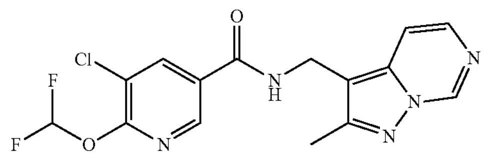 [SMILES: Cc1nn2cnccc2c1CNC(=O)c1cnc(OC(F)F)c(F)c1] | | 366.0 |
| 57 | 3-fluoro-N-((1-methyl-1H-imidazo[1,2-b]pyrazol-7-yl)methyl)-4-(trifluoromethoxy)benzamide | 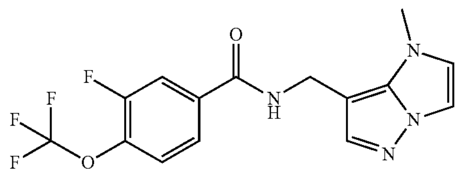 [SMILES: Cn1ccn2ncc(CNC(=O)c3ccc(OC(F)(F)F)c(F)c3)c12] | | 357.1 |
| 58 | 6-(difluoromethoxy)-5-fluoro-N-((1-methyl-1H-imidazo[1,2-b]pyrazol-7-yl)methyl)nicotinamide | 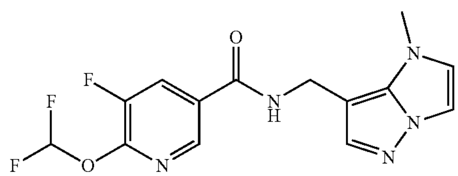 [SMILES: Cn1ccn2ncc(CNC(=O)c3cnc(OC(F)F)c(F)c3)c12] | | 340.1 |
| 59 | 5-chloro-6-(difluoromethoxy)-N-((1-methyl-1H-imidazo[1,2-b]pyrazol-7-yl)methyl)nicotinamide | 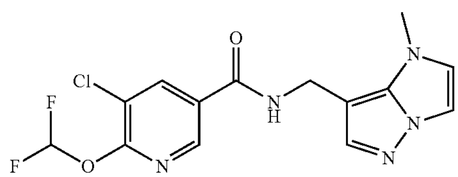 [SMILES: Cn1ccn2ncc(CNC(=O)c3cnc(OC(F)F)c(Cl)c3)c12] | | 356.1 |
| 60 | 4-(cyclopropyloxy)-N-((1-methyl-1H-imidazo[1,2-b]pyrazol-7-yl)methyl)benzamide | 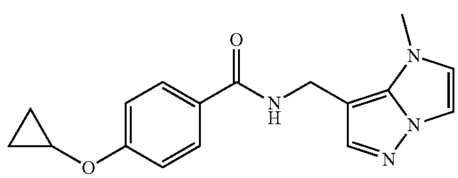 [SMILES: Cn1ccn2ncc(CNC(=O)c3ccc(OC4CC4)cc3)c12] | | 311.2 |
| 61 | 5-fluoro-6-methoxy-N-((1-methyl-1H-imidazo[1,2-b]pyrazol-7-yl)methyl)nicotinamide | 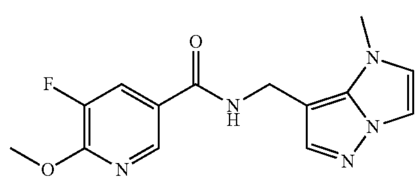 [SMILES: COc1ncc(C(=O)NCc2cnn3ccn(C)c23)cc1F] | | 304.1 |
| 62 | 3,5-difluoro-4-methoxy-N-((1-methyl-1H-imidazo[1,2-b]pyrazol-7-yl)methyl)benzamide | 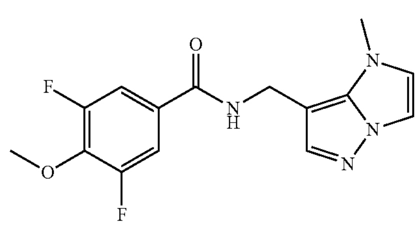 [SMILES: COc1c(F)cc(C(=O)NCc2cnn3ccn(C)c23)cc1F] | | 321.2 |

TABLE 1-continued

| EXAMPLE | IUPAC NAME | Structure | ADDITIVE | MS |
|---|---|---|---|---|
| 63 | 4-chloro-3-fluoro-N-((1-methyl-1H-imidazo[1,2-b]pyrazol-7-yl)methyl)benzamide | 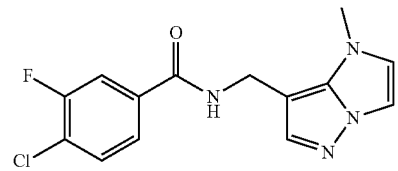 [SMILES: Cn1ccn2ncc(CNC(=O)c3ccc(Cl)c(F)c3)c12] | | 308.0 |
| 64 | N-((1-methyl-1H-imidazo[1,2-b]pyrazol-7-yl)methyl)-6-(trifluoromethoxy)nicotinamide | 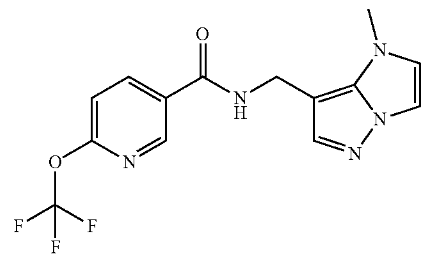 [SMILES: Cn1ccn2ncc(CNC(=O)c3ccc(OC(F)(F)F)nc3)c12] | | 340.1 |
| 65 | N-((1-methyl-1H-imidazo[1,2-b]pyrazol-7-yl)methyl)-5-(trifluoromethyl)thiophene-2-carboxamide | 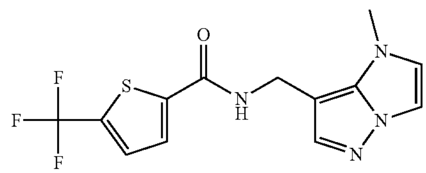 [SMILES: Cn1ccn2ncc(CNC(=O)c3ccc(C(F)(F)F)s3)c12] | | 329.1 |
| 66 | N-((1-methyl-1H-imidazo[1,2-b]pyrazol-7-yl)methyl)-4-(trifluoromethoxy)benzamide | 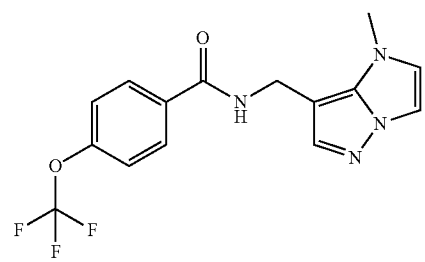 [SMILES: Cn1ccn2ncc(CNC(=O)c3ccc(OC(F)(F)F)cc3)c12] | | 339.1 |
| 67 | 3-fluoro-N-((1-methyl-1H-imidazo[1,2-b]pyrazol-7-yl)methyl)-4-(trifluoromethyl)benzamide | 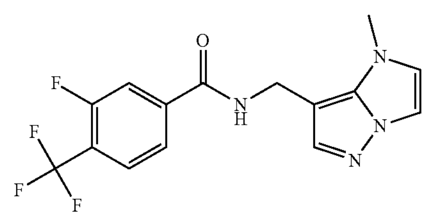 [SMILES: Cn1ccn2ncc(CNC(=O)c3ccc(C(F)(F)F)c(F)c3)c12] | | 341.1 |
| 68 | 3-fluoro-N-([1,2,3]triazolo[1,5-a]pyridin-3-ylmethyl)-4-(trifluoromethyl)benzamide | 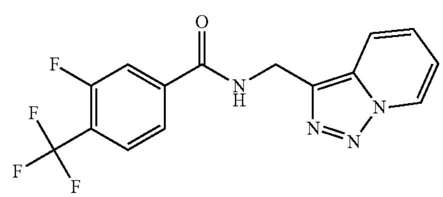 [SMILES: O=C(NCc1nnn2ccccc12)c1ccc(C(F)(F)F)c(F)c1] | | 339.1 |
| 69 | N-([1,2,3]triazolo[1,5-a]pyridin-3-ylmethyl)-4-(trifluoromethoxy)benzamide | 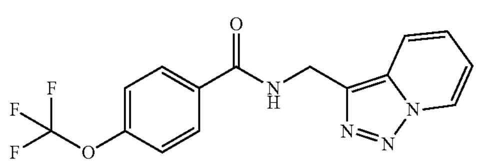 [SMILES: O=C(NCc1nnn2ccccc12)c1ccc(OC(F)(F)F)cc1] | | 337.1 |

TABLE 1-continued

| EXAMPLE | IUPAC NAME | Structure | ADDITIVE | MS |
|---|---|---|---|---|
| 70 | 6-(difluoromethoxy)-N-[(1,2-dimethyl-1H-pyrazolo[1,5-b][1,2,4]triazol-7-yl)methyl]-5-fluoropyridine-3-carboxamide | 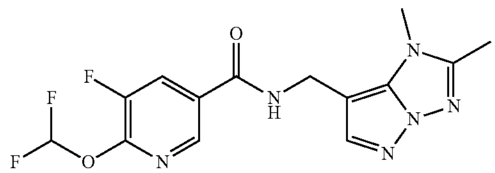 | | 355.2 |
| 71 | N-[(1,2-dimethyl-1H-pyrazolo[1,5-b][1,2,4]triazol-7-yl)methyl]-3-fluoro-4-(trifluoromethoxy)benzamide | 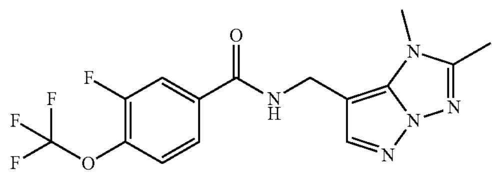 [SMILES: Cc1nn2ncc(CNC(=O)c3ccc(OC(F)(F)F)c(F)c3)c2n1C] | | 372.1 |
| 72 | 5-chloro-6-(difluoromethoxy)-N-[(1,2-dimethyl-1H-pyrazolo[1,5-b][1,2,4]triazol-7-yl)methyl]pyridine-3-carboxamide | 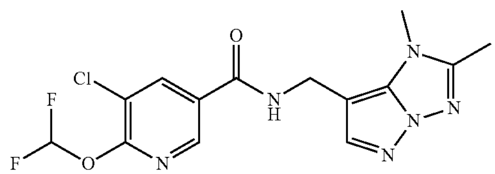 [SMILES: Cc1nn2ncc(CNC(=O)c3cnc(OC(F)F)c(Cl)c3)c2n1C] | | 371.1 |
| 73 | 6-(difluoromethoxy)-N-[(1,6-dimethyl-1H-imidazo[1,2-b]pyrazol-7-yl)methyl]-5-fluoropyridine-3-carboxamide | 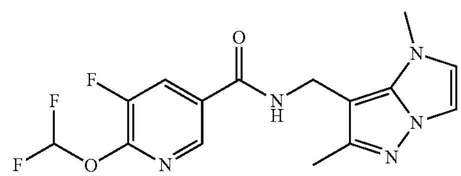 [SMILES: Cc1nn2ccn(C)c2c1CNC(=O)c1cnc(OC(F)F)c(F)c1] | | 354.2 |
| 74 | 6-(difluoromethoxy)-N-{[1-(difluoromethyl)-2-methyl-1H-pyrazolo[1,5-b][1,2,4]triazol-7-yl]methyl}-5-fluoropyridine-3-carboxamide | 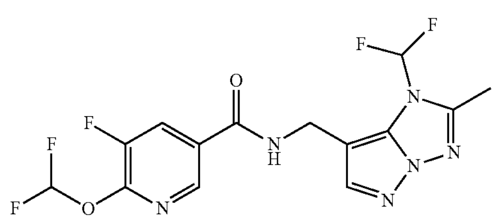 [SMILES: Cc1nn2ncc(CNC(=O)c3cnc(OC(F)F)c(F)c3)c2n1C(F)F] | | 389.2 |
| 75 | 5-chloro-6-(difluoromethoxy)-N-{[1-(difluoromethyl)-2-methyl-1H-pyrazolo[1,5-b][1,2,4]triazol-7-yl]methyl}pyridine-3-carboxamide | 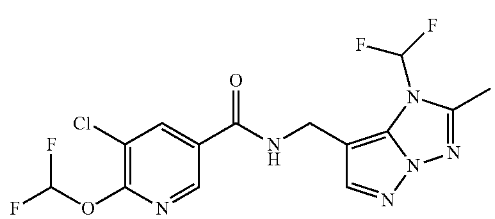 [SMILES: Cc1nn2ncc(CNC(=O)c3cnc(OC(F)F)c(Cl)c3)c2n1C(F)F] | | 405.1 |
| 76 | 6-(difluoromethoxy)-N-{[1-(difluoromethyl)-1H-imidazo[1,2-b]pyrazol-7-yl]methyl}-5-fluoropyridine-3-carboxamide | 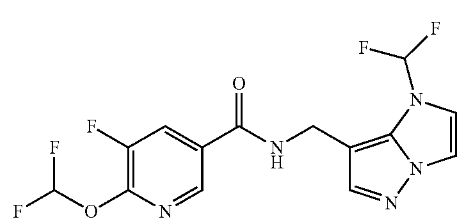 [SMILES: O=C(NCc1cnn2ccn(C(F)F)c12)c1cnc(OC(F)F)c(F)c1] | | 376.1 |

TABLE 1-continued

| EXAMPLE | IUPAC NAME | Structure | ADDITIVE | MS |
|---|---|---|---|---|
| 77 | 5-chloro-N-{[1-(2,2-difluoroethyl)-2-methyl-1H-pyrazolo[1,5-b][1,2,4]triazol-7-yl]methyl}-6-(difluoromethoxy)pyridine-3-carboxamide | 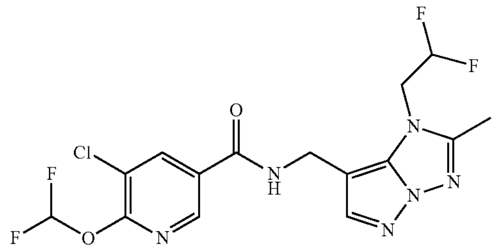 [SMILES: Cc1nn2ncc(CNC(=O)c3cnc(OC(F)F)c(Cl)c3)c2n1CC(F)F] | | 421.1 |
| 78 | N-{[1-(2,2-difluoroethyl)-2-methyl-1H-pyrazolo[1,5-b][1,2,4]triazol-7-yl]methyl}-3-fluoro-4-(trifluoromethoxy)benzamide | 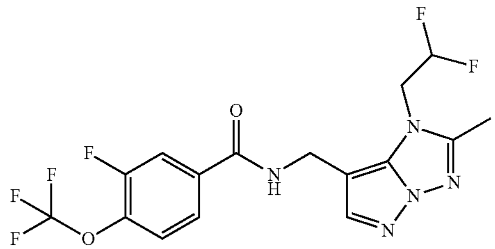 [SMILES: Cc1nn2ncc(CNC(=O)c3ccc(OC(F)(F)F)c(F)c3)c2n1CC(F)F] | | 422.2 |
| 79 | N-{[1-(2,2-difluoroethyl)-1H-imidazo[1,2-b]pyrazol-7-yl]methyl}-6-(difluoromethoxy)-5-fluoropyridine-3-carboxamide | 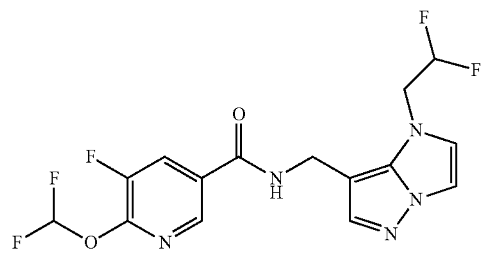 [SMILES: O=C(NCc1cnn2ccn(CC(F)F)c12)c1cnc(OC(F)F)c(F)c1] | | 390.1 |
| 80 | 5-chloro-N-{[1-(2,2-difluoroethyl)-1H-imidazo[1,2-b]pyrazol-7-yl]methyl}-6-(difluoromethoxy)pyridine-3-carboxamide | 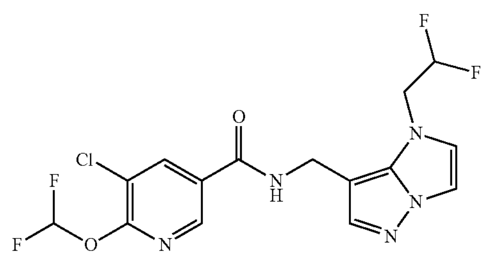 [SMILES: O=C(NCc1cnn2ccn(CC(F)F)c12)c1cnc(OC(F)F)c(Cl)c1] | | 406.1 |
| 81 | N-{[1-(2,2-difluoroethyl)-1H-imidazo[1,2-b]pyrazol-7-yl]methyl}-3-fluoro-4-(trifluoromethoxy)benzamide | 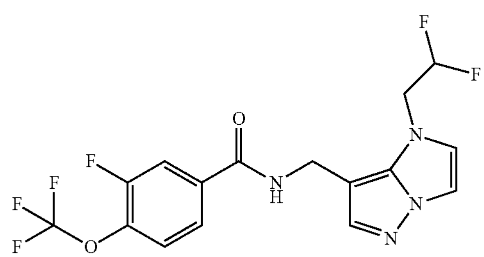 [SMILES: O=C(NCc1cnn2ccn(CC(F)F)c12)c1ccc(OC(F)(F)F)c(F)c1] | | 407.1 |
| 82 | 6-(difluoromethoxy)-5-fluoro-N-{[1-(2,2,2-trifluoroethyl)-1H-imidazo[1,2-b]pyrazol-7-yl]methyl}pyridine-3-carboxamide | 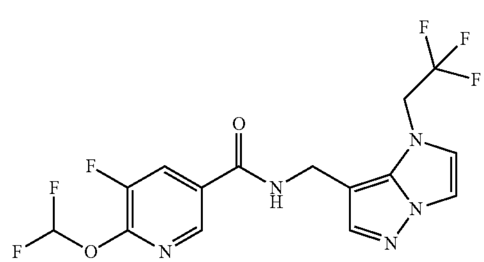 [SMILES: O=C(NCc1cnn2ccn(CC(F)(F)F)c12)c1cnc(OC(F)F)c(F)c1] | | 408.1 |

TABLE 1-continued

| EXAMPLE | IUPAC NAME | Structure | ADDITIVE | MS |
|---|---|---|---|---|
| 83 | 6-(difluoromethoxy)-N-[(1-ethyl-1H-imidazo[1,2-b]pyrazol-7-yl)methyl]-5-fluoropyridine-3-carboxamide | 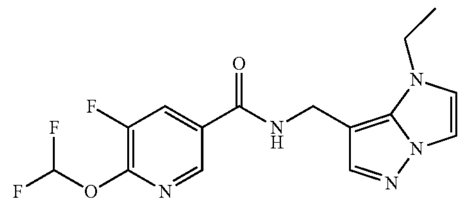 [SMILES: CCn1ccn2ncc(CNC(=O)c3cnc(OC(F)F)c(F)c3)c12] | | 354.2 |
| 84 | 5-chloro-6-(difluoromethoxy)-N-[(1-ethyl-1H-imidazo[1,2-b]pyrazol-7-yl)methyl]pyridine-3-carboxamide | 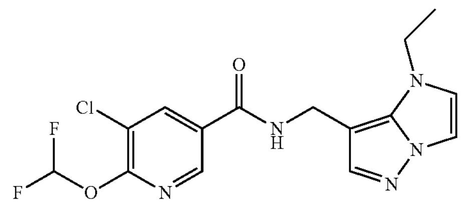 [SMILES: CCn1ccn2ncc(CNC(=O)c3cnc(OC(F)F)c(Cl)c3)c12] | | 370.2 |
| 85 | 6-(difluoromethoxy)-N-[(1,2-dimethyl-1H-imidazo[1,2-b]pyrazol-7-yl)methyl]-5-fluoropyridine-3-carboxamide | 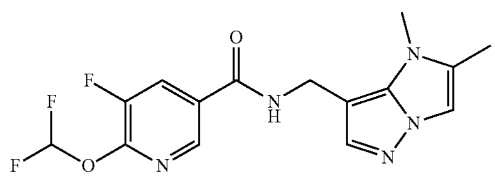 [SMILES: Cc1cn2ncc(CNC(=O)c3cnc(OC(F)F)c(F)c3)c2n1C] | | 354.2 |

Experimental Example 1

NR2B $Ca^{2+}$ Influx Assay

In order to confirm an "antagonistic action on an NMDA receptor containing the NR2B subunit" which the compound of the present invention has, inhibitory effect on the NMDA receptor activation was evaluated using "NMDA receptor composed of four subunits consisting of two sets of heterodimers of NR1 and NR2B"-expressing human fetal renal cells, specifically human glutamate ionotropic receptor NMDA type subunit 1 (GRIN1) and human glutamate ionotropic receptor NMDA type subunit 2B (GRIN2B)-expressing HEK293 cells.

As an index of the NMDA receptor activation, intracellular calcium ion ($Ca^{2+}$) influx caused by bonding of glycine and glutamate to NR1 and NR2B respectively was used. HEK293 cells were purchased from ChanTest. The cells were cultured in a DMEM/F-12 (COSMO BIO, 10-092-CM) medium containing 10% FBS (fetal bovine serum, AusGene), 100 units/mL penicillin, 100 μg/mL streptomycin, 500 μg/mL neomycin, 100 μg/mL Zeocin and 5 μg/mL Blasticidin at 37° C., 5% $CO_2$. The cells were detached from flask with trypsin the day before the assay, suspended in a seeding medium (DMEM (Invitrogen, 31053) containing 10% FBS, 100 units/mL penicillin and 100 μg/mL streptomycin) at 8×10$^5$ cells/mL, seeded by 25 μL per well in a 384-well plate (Falcon, 356663) at 20000 cells/well, and cultured overnight in an incubator. On the day of the assay, tetracycline (Wako Pure Chemical Industries, 209-16561) was diluted with the seeding medium at 2 μg/mL, and the dilution was added at 25 μL/well to the plate seeded with the cells, and the cells were cultured for 2 hr in an incubator. Thereafter, the medium was removed, and the cells were washed with 50 μL/well of assay buffer (137 mM NaCl, 4 mM KCl, 1.8 mM $CaCl_2$, 10 mM HEPES (pH 7.2), 10 mM Glucose, and 0.1% BSA). Then, a loading buffer (assay buffer containing 2.5 μM Fluo-4AM, 2 mM Amaranth and 1 mM Tartrazine) was added thereto at 25 μL/well, and loading was performed in the incubator for 30 min, and then at room temperature for 15 min. The test compound was diluted with the above-mentioned assay buffer so as to adjust the concentration to 30 μM, the obtained solution (25 μL) was added thereto (the final concentration 10 μM), and the cells were stood for 15 min at room temperature. Using FLIPR (Molecular Devices), 25 μL of an assay buffer containing 30 μM glutamic acid and 30 μM glycine was added thereto, and the fluorescence signal was measured every 3 seconds for 5 min. The relative activity value (inhibitory rate) was calculated when the cumulative total value of the fluorescence value of a well added with a buffer free of glutamic acid and glycine, relative to the cumulative total value of the fluorescence value of each well are regarded as 100% inhibition. The obtained value was evaluated as an inhibitory activity. The results are shown in the following Table 2.

TABLE 2

| Example No. | inhibitory rate (10 μM compound concentration) |
|---|---|
| 1 | 94 |
| 2 | 54 |
| 3 | 76 |
| 4 | 85 |
| 5 | 99 |
| 6 | 97 |
| 7 | 98 |
| 8 | 97 |
| 9 | 87 |
| 10 | 97 |
| 11 | 98 |
| 12 | 97 |
| 13 | 96 |
| 14 | 94 |
| 15 | 98 |
| 16 | 97 |
| 17 | 94 |
| 18 | 98 |

TABLE 2-continued

| Example No. | inhibitory rate (10 μM compound concentration) |
|---|---|
| 19 | 96 |
| 20 | 97 |
| 21 | 97 |
| 22 | 98 |
| 23 | 95 |
| 24 | 70 |
| 25 | 78 |
| 26 | 90 |
| 27 | 92 |
| 28 | 85 |
| 29 | 89 |
| 30 | 97 |
| 31 | 84 |
| 32 | 93 |
| 33 | 97 |
| 34 | 96 |
| 35 | 94 |
| 36 | 97 |
| 37 | 96 |
| 38 | 98 |
| 39 | 97 |
| 40 | 98 |
| 41 | 86 |
| 42 | 94 |
| 43 | 95 |
| 44 | 94 |
| 45 | 92 |
| 46 | 96 |
| 47 | 93 |
| 48 | 90 |
| 49 | 98 |
| 50 | 97 |
| 51 | 97 |
| 52 | 95 |
| 53 | 84 |
| 54 | 79 |
| 55 | 84 |
| 56 | 85 |
| 57 | 97 |
| 58 | 97 |
| 59 | 97 |
| 60 | 88 |
| 61 | 88 |
| 62 | 95 |
| 63 | 96 |
| 64 | 96 |
| 65 | 96 |
| 66 | 98 |
| 67 | 98 |
| 68 | 83 |
| 69 | 92 |
| 70 | 100 |
| 71 | 97 |
| 72 | 95 |
| 73 | 93 |
| 74 | 90 |
| 75 | 91 |
| 76 | 87 |
| 77 | 54 |
| 78 | 81 |
| 79 | 87 |
| 80 | 91 |
| 81 | 96 |
| 82 | 72 |
| 83 | 94 |
| 84 | 95 |
| 85 | 97 |

As shown in the above-mentioned Table 2, the compound of the present invention inhibited intracellular calcium ion ($Ca^{2+}$) influx in the NMDA receptor containing the NR2B subunit. That is, the compound of the present invention was confirmed to have an antagonistic action on an NMDA receptor containing the NR2B subunit.

Experimental Example 2 hERG Manual Patch-Clamp Assay

In order to confirm "hERG channel inhibitory activity" which the compound of the present invention has, the hERG channel inhibitory activity was evaluated using human Ether-a-go-go-Related Gene (hERG)-expressing human embryonic kidney 293 (HEK293) cells.

hERG-stably expressing HEK293 cells were purchased from University of Wisconsin-Madison Dept. Medicine. The cells were cultured in a medium prepared by adding 10% FBS (fetal bovine serum, Life Technologies Corporation), sodium pyruvate (1 mmol/L; Life Technologies Corporation), MEM Non-Essential Amino Acid (lx; Life Technologies Corporation), 100 units/mL penicillin, 100 μg/mL streptomycin (Life Technologies Corporation) and 400 μg/mL G 418 (Geneticin, Sigma-Aldrich Co. LLC.) to Minimum Essential Medium (Sigma-Aldrich Co. LLC.) at 37° C., 5% $CO_2$. The cultured cells were detached, suspended in a medium, and seeded on a cover glass, cultured, and used in a patch-clamp assay. The extracellular fluid was composed of NaCl: 137 mmol/L, KCl: 4 mmol/L, $CaCl_2$): 1.8 mmol/L, $MgCl_2$: 1 mmol/L, D(+)-Glucose: 10 mmol/L, and HEPES: 10 mmol/L (pH 7.4 adjusted with 1 mol/L NaOH), and the solution inside electrode was composed of KCl: 130 mmol/L, $MgCl_2$: 1 mmol/L, EGTA: 5 mmol/L, MgATP: 5 mmol/L, and HEPES: 10 mmol/L (pH 7.2 adjusted with 1 mol/L KOH). Glass fine tube (G-1.5, NARISHIGE) was processed into a glass electrode using glass electrode making apparatus (P-97, Sutter Instrument Company), and the glass electrode having an ohmic value within the range of 2 to 5 MΩ of when filled with the solution inside electrode was used for measurement. DMSO solution (3.33 mmol/L) of the example compound was diluted with the extracellular fluid by 333-fold to prepare a 10 μmol/L test solution.

The hERG current passing through whole cell membranes under voltage-clamp was recorded by whole-cell patch-clamp method. The hERG current through the cells was induced by the following depolarizing pulse. The cell membrane potential was held at −80 mV, and then depolarizing pulse at −50 mV, 110 msec and 20 mV, 4 sec, followed by repolarizing pulse at −50 mV, 2 sec were given every 15 min. After the generated current became stable, application of 10 μmol/L test solution was started, and the pulse was continuously given during the application. The sampling frequency was set at 5 kHz, and Lowpass Filter was set at 2 kHz. During measurement, the extracellular fluid temperature in the chamber was set at 20 to 25° C., and the hERG current was measured using patch-clamp amplifier (Axopatch-200B, Molecular Devices, LLC). The obtained electrical signal was recorded on a computer via patch-clamp record and analysis software (pCLAMP 10, Molecular Devices, LLC). The absolute value of the hERG current value (peak tail current) was calculated based on the current value when depolarizing pulse at −50 mV, 110 msec was given, and the change (inhibitory rate) in the hERG current value (peak tail current) 3 to 5 min after the application of the 10 μmol/L test solution relative to before the application was calculated. The results are shown in Table 3.

TABLE 3

| Example No. | inhibitory rate (10 μM compound concentration) |
|---|---|
| 6 | 16.5 |
| 13 | 33.2 |
| 58 | 13.6 |

As shown in the above-mentioned Table 3, the compound of the present invention did not show strong current inhibition against hERG channel at 10 μmol/L. That is, the compound of the present invention is expected to be less concerned about lethal arrhythmia (Torsade de pointes) due to QT prolongation.

Experimental Example 3

[³H]MK-801 Binding Test In Vivo

In order to confirm "functional antagonistic action on an NMDA receptor containing the NR2B subunit in vivo" which the compound of the present invention has, binding test was performed using tritium-labeled form of MK-801 ((5R,10S)-5-methyl-10,11-dihydro-5H-5,10-epiminodibenzo[a,d][7]annulene) ([³H]MK-801), which is a compound capable of binding to the opening site of the NMDA receptor.

The example compound (3 mg/kg/2 mL, 0.5% MC water) or vehicle (kg/2 mL, 0.5% MC water) was orally administered (p.o.) to Sprague Dawley rats (body weight 180-260 g). After a certain time (around after time-to maximum blood concentration), [³H]MK-801 (20 μCi/kg/mL, Muromachi Kikai) was intravenously administered. After 10 min, the rats were euthanized by decapitation, and subjected to craniotomy, and the hippocampus was collected. The collected hippocampus was homogenized in 30 volumes (30 mL per 1 g tissue) ice-cooled 20 mM Hepes (pH7.5, Hampton Research) using a homogenizer (T10 basic Ultra-Turrax) for 10 sec. Then, 600 μL of the homogenate was immediately filtered through GF/B Whatman glass filter (GE Health Care), which were presoaked in 0.5% polyethyleneimine (FUJIFILM Wako Pure Chemical Corporation) and set on Manifold Filtration System (Millipore) by suction. The filter was washed four times with ice-cooled saline (5 mL, Otsuka Pharmaceutical), put into a scintillation vial, and then 10 mL of liquid scintillator A (FUJIFILM Wako Pure Chemical Corporation) was added thereto, and the residual radioactivity was counted using liquid scintillation counter (ALOKA LSC-6100). Separately, the residual radioactivity in 100 μL of the homogenate before the filtration was counted in the same way. The value of [the residual radioactivity in the filter/the residual radioactivity in the 100 μL of the homogenate] was calculated as a [³H]MK-801 binding rate to the NMDA receptor expressing in each individual hippocampus tissue. Then, the [³H]MK-801 binding rate in the vehicle control group was regarded as 100%, and the [³H]MK-801 binding rate in the group subcutaneously administered with excess amount of MK-801 maleate (2 mg/kg/2 mL, 0.5% MC water) was regarded as 0%. The difference between the percentage of [³H]MK-801 binding rate in the group orally administered with the example compound and that in the vehicle control group (100%) was analyzed as [³H]MK-801 binding inhibitory rate by the example compound. The results are shown in Table 4.

TABLE 4

| Example No. | inhibitory rate (3 mg/kg, p.o.) |
|---|---|
| 6 | 33% |
| 13 | 23% |
| 58 | 27% |

As shown in the above-mentioned Table 4, the compound of the present invention inhibited the binding of [³H]MK-801 which is a compound capable of binding to the opening site of the NMDA receptor containing the NR2B subunit. That is, the compound of the present invention was confirmed to have a functional antagonistic action on an NMDA receptor containing the NR2B subunit in vivo.

Formulation Example 1 (Production of Capsule)

| | |
|---|---|
| 1) compound of Example 1 | 30 mg |
| 2) fine powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablet)

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an antagonistic action on an NMDA receptor containing the NR2B subunit, and is expected to be useful as an agent for the prophylaxis or treatment of major depression, bipolar disorder, migraine, pain, behavioral and psychological symptoms of dementia and the like.

This application is based on patent application No. 2018-062939 filed on Mar. 28, 2018 in Japan, the contents of which are encompassed in full herein.

The invention claimed is:

1. A compound represented by the formula (I):

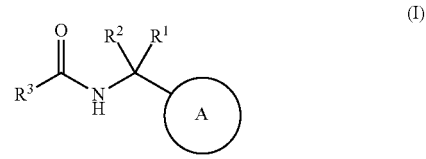

(I)

wherein
the group represented by

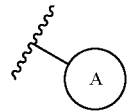

is a group represented by

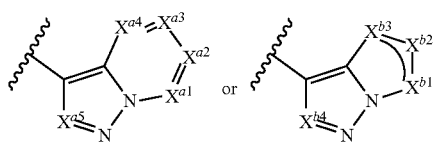

$X^{a1}$ is CH or a nitrogen atom;
$X^{a2}$ is
(1) $CR^a$ wherein $R^a$ is
  (a) a hydrogen atom,
  (b) a halogen atom, or
  (c) a $C_{1-6}$ alkyl group, or
(2) a nitrogen atom;
$X^{a3}$ is
(1) $CR^a$ wherein $R^a$ is
  (a) a hydrogen atom, or
  (b) a $C_{1-6}$ alkyl group, or
(2) a nitrogen atom;
$X^{a4}$ is
(1) $CR^a$ wherein $R^a$ is
  (a) a hydrogen atom, or
  (b) a C1-6 alkyl group, or
(2) a nitrogen atom; and
$X^{a5}$ is
(1) $CR^a$ wherein $R^a$ is
  (a) a hydrogen atom,
  (b) a $C_{1-6}$ alkyl group optionally substituted by 1 to 3 substituents selected from a halogen atom and a $C_{1-6}$ alkoxy group,
  (c) a $C_{1-6}$ alkoxy group, or
  (d) a $C_{3-10}$ cycloalkyl group, or
(2) a nitrogen atom;
provided that when $X^{a5}$ is $CR^a$, then at least one of $X^{a1}$, $X^{a2}$ and $X^{a3}$ is a nitrogen atom;
$X^{b1}$ is CH or a nitrogen atom;
$X^{b2}$ is $CR^b$ wherein $R^b$ is
  (a) a hydrogen atom, or
  (b) a $C_{1-6}$ alkyl group;
$X^{b3}$ is a nitrogen atom optionally substituted by a $C_{1-6}$ alkyl group optionally substituted by 1 to 3 halogen atoms; and
$X^{b4}$ is $CR^b$ wherein $R^b$ is
  (a) a hydrogen atom, or
  (b) a $C_{1-6}$ alkyl group;
$R^1$ and $R^2$ are each a hydrogen atom; and
$R^3$ is a group represented by

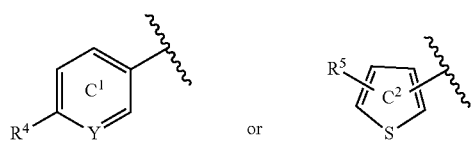

$R^4$ is
(1) a $C_{1-6}$ alkyl group optionally substituted by 1 to 3 halogen atoms,
(2) a $C_{1-6}$ alkoxy group optionally substituted by 1 to 3 halogen atoms,
(3) a $C_{3-10}$ cycloalkyloxy group, or
(4) a halogen atom;

Y is a nitrogen atom or $CR^6$ wherein $R^6$ is a hydrogen atom or a halogen atom; and
Ring $C^1$ is a benzene ring (i.e., Y is $CR^6$) or a pyridine ring (i.e., Y is N), each of which is optionally further substituted by one halogen atom;
$R^5$ is a $C_{1-6}$ alkyl group optionally substituted by 1 to 3 halogen atoms; and
Ring $C^2$ is a thiophene ring substituted by only $R^5$,
or a salt thereof.

2. The compound or salt according to claim 1, wherein the group represented by

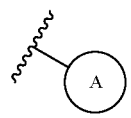

is a group represented by

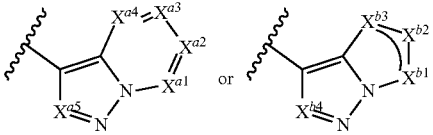

$X^{a1}$ is CH or a nitrogen atom;
$X^{a2}$ is CH;
$X^{a3}$ is CH or a nitrogen atom;
$X^{a4}$ is CH; and
$X^{a5}$ is CH or a nitrogen atom;
provided that when $X^{a5}$ is CH, then at least one of $X^{a1}$ and $X^{a3}$ is a nitrogen atom;
$X^{b1}$ is CH;
$X^{b2}$ is CH;
$X^{b3}$ is a nitrogen atom optionally substituted by a $C_{1-6}$ alkyl group; and
$X^{b4}$ is CH;
$R^1$ and $R^2$ are both hydrogen atoms; and
$R^3$ is a group represented by

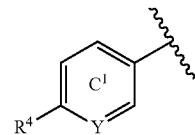

$R^4$ is a $C_{1-6}$ alkoxy group optionally substituted by 1 to 3 halogen atoms;
Y is a nitrogen atom or CH; and
Ring $C^1$ is a benzene ring (i.e., Y is CH) or a pyridine ring (i.e., Y is N), each of which is optionally further substituted by one halogen atom.

3. The compound or salt according to claim 1, wherein the group represented by

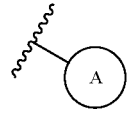

is a group represented by

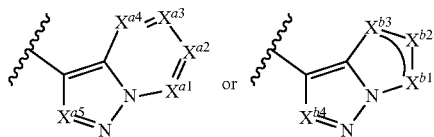

$X^{a1}$ is CH or a nitrogen atom;
$X^{a2}$ is CH;
$X^{a3}$ is CH;
$X^{a4}$ is CH; and
$X^{a5}$ is CH or a nitrogen atom;
provided that when $X^{a5}$ is CH, then $X^{a1}$ is a nitrogen atom;
$X^{b1}$ is CH;
$X^{b2}$ is CH;
$X^{b3}$ is a nitrogen atom optionally substituted by a $C_{1-6}$ alkyl group; and
$X^{b4}$ is CH;
$R^1$ and $R^2$ are both hydrogen atoms; and
$R^3$ is a group represented by

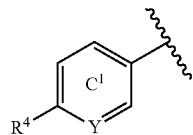

$R^4$ is a $C_{1-6}$ alkoxy group optionally substituted by 1 to 3 halogen atoms;

Y is a nitrogen atom or CH; and

Ring $C^1$ is a benzene ring (i.e., Y is CH) or a pyridine ring (i.e., Y is N), each of which is optionally further substituted by one halogen atom.

4. 6-(Difluoromethoxy)-5-fluoro-N-[(pyrazolo[1,5-b]pyridazin-3-yl)methyl]pyridine-3-carboxamide or a salt thereof.

5. 3-Fluoro-N-[([1,2,3]triazolo[1,5-a]pyridin-3-yl)methyl]-4-(trifluoromethoxy)benzamide or a salt thereof.

6. 6-(Difluoromethoxy)-5-fluoro-N-[(1-methyl-1H-imidazo[1,2-b]pyrazol-7-yl)methyl]pyridine-3-carboxamide or a salt thereof.

7. A pharmaceutical composition comprising the compound or salt according to claim 1, and a pharmacologically acceptable carrier.

8. A method for the treatment of major depression, bipolar disorder, migraine, pain, or behavioral and psychological symptoms of dementia in a mammal, which comprises administering an effective amount of the compound or salt according to claim 1 to the mammal.

\* \* \* \* \*